United States Patent
Smith

(10) Patent No.: US 12,018,331 B2
(45) Date of Patent: Jun. 25, 2024

(54) METHODS OF DIAGNOSING CANCER USING CANCER TESTIS ANTIGENS

(71) Applicant: YISSUM RESEARCH DEVELOPMENT COMPANY OF THE HEBREW UNIVERSITY OF JERUSALEM LTD., Jerusalem (IL)

(72) Inventor: Yoav Smith, Jerusalem (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 0 days.

(21) Appl. No.: 16/304,150

(22) PCT Filed: May 23, 2017

(86) PCT No.: PCT/IL2017/050575
§ 371 (c)(1),
(2) Date: Nov. 22, 2018

(87) PCT Pub. No.: WO2017/203526
PCT Pub. Date: Nov. 30, 2017

(65) Prior Publication Data
US 2019/0292601 A1    Sep. 26, 2019

Related U.S. Application Data

(60) Provisional application No. 62/445,286, filed on Jan. 12, 2017, provisional application No. 62/340,449, filed on May 23, 2016.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57423* (2013.01); *G01N 33/5743* (2013.01); *G01N 33/57434* (2013.01); *G01N 33/57438* (2013.01); *G01N 33/57449* (2013.01); *G01N 33/57488* (2013.01); *C12Q 2600/112* (2013.01); *C12Q 2600/118* (2013.01); *C12Q 2600/158* (2013.01); *G01N 33/57415* (2013.01); *G01N 2800/52* (2013.01); *G01N 2800/56* (2013.01)

(58) Field of Classification Search
None
See application file for complete search history.

(56) References Cited

FOREIGN PATENT DOCUMENTS

| WO | 2010065944 A1 | 6/2010 | |
|----|---|---|---|
| WO | 2011094233 A1 | 8/2011 | |
| WO | 2012178128 A1 | 12/2012 | |
| WO | 2013131050 A1 | 9/2013 | |
| WO | 2015120382 A1 | 8/2015 | |
| WO | WO-2017203526 A1 * | 11/2017 | ....... G01N 33/57423 |

OTHER PUBLICATIONS

Benner et al (Trends in Genetics (2001) vol. 17, pp. 414-418).*
Cheung et al (Nature Genetics, 2003, vol. 33, pp. 422-425).*
Saito-Hisaminato et al. (DNA research (2002) vol. 9, pp. 35-45).*
Gillespie (British journal of cancer (1998) vol. 78, pp. 816-821).*
Greenbaum et al (Genome Biology 2003, vol. 4, article 117, pp. 1-8).*
Li (Oncotarget (2014) vol. 5, pp. 587-598).*
Rivera (Oncology Letters (2014) vol. 8, pp. 7-11).*
Muller-Ricther (Head & Face Medicine (BMC central (2009) vol. 5:10, pp. 1-9).*
Ambatipudi (Genes, Chromosomes & cancer (2012) vol. 51, pp. 161-173).*
Pereira (oncology reports (2012) vol. 27, pp. 1843-1848).*
Krishan and Feldman (Annual Review Pharmacology Toxicology (2011) vol. 51, pp. 311-336).*
Feller (Journal of Cancer Therapy (2012) vol. 3, pp. 263-268).*
Daley et al J Can Dent Assoc. 2003. 69(9): 577-582 (Year: 2003).*
The Human Protein Atlas for LY6K, available via URL: <proteinatlas.org/ENSG00000160886-LY6K/pathology>, printed on Aug. 1, 2023 (Year: 2023).*
Chen et al. Molecular & Cellular Proteomics. 2002. 1:304-313 (Year: 2002).*
Zhang et al Nature. Sep. 18, 2014. 513(7518): 382-387 (Year: 2014).*
Takumi Shiraishi et al., "Cancer/Testis antigens as potential predictors of biochemical recurrence of prostate cancer following radical prostatectomy", Journal of Translational Medicine, (Jan. 1, 2011), vol. 9, No. 1, p. 153, XP055067012 ISSN 1479-5876, DOI.
Suri Anil, "Cancer Testis Antigens—Their Importance in Immunotherapy and in the Early Detection of Cancer", Expert Opinion on Biological The, Informa Healthcare, Ashley, London; GB, (Apr. 1, 2006) vol. 6, No. 4 pp. 379-389, XP009074181.
J. Yao et al, "Tumor Subtype-Specific Cancer-Testis Antigens as Potential Biomarkers and Immunotherapeutic Targets for Cancers", Cancer Immunology Research, US, (Nov. 25, 2013) vol. 2, No. 4 pp. 371-379, XP055340855 ISSN 2326-6066, DOI.

\* cited by examiner

*Primary Examiner* — Carla J Myers
(74) *Attorney, Agent, or Firm* — The Roy Gross Law Firm, LLC; Roy Gross

(57) ABSTRACT

Methods and kits for the diagnosis of cancer based on specific expression profiles of Cancer Testis Antigens (CTA) are provided.

9 Claims, 21 Drawing Sheets
(1 of 21 Drawing Sheet(s) Filed in Color)

FIG. 17A
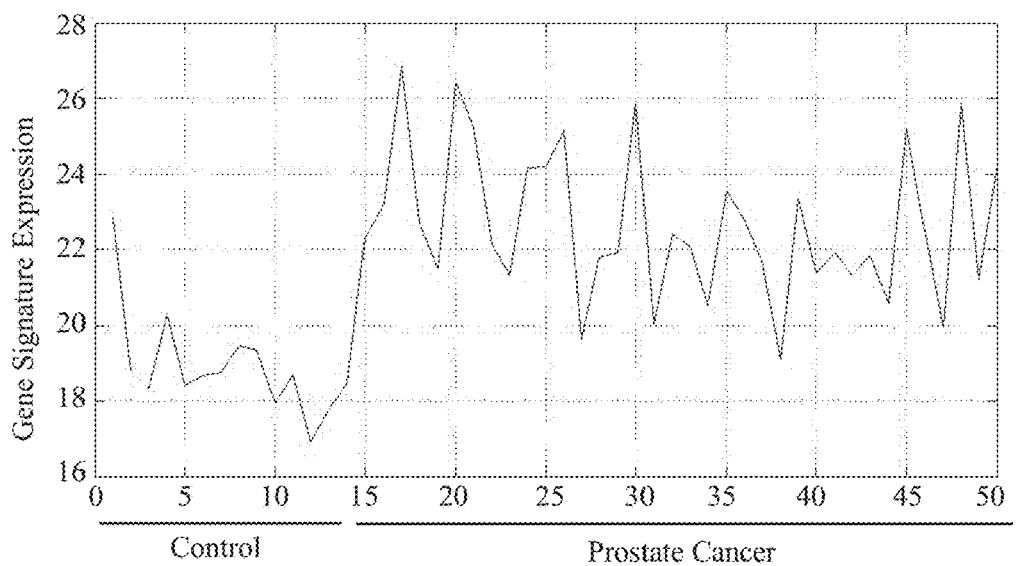
FIG. 17B
FIG. 18A
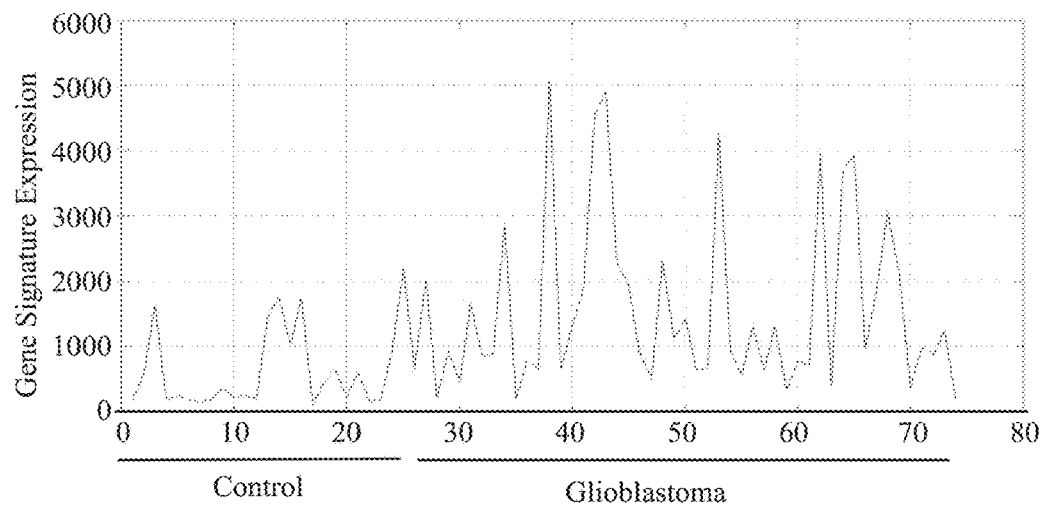

METHODS OF DIAGNOSING CANCER USING CANCER TESTIS ANTIGENS

CROSS REFERENCE TO RELATED APPLICATIONS

This application is a national phase of PCT Patent Application No. PCT/IL2017/050575, filed May 23, 2017, which claims the benefit of priority of U.S. Provisional Patent Application No. 62/340,449, filed May 23, 2016, and U.S. Provisional Patent Application No. 62/445,286, filed Jan. 12, 2017, the contents of which are all incorporated herein by reference in their entirety.

FIELD OF INVENTION

The present invention is directed to, inter alia, methods and kits for gene expression profiling for the diagnosis, prognosis, monitoring, and screening of cancer and/or for identifying subjects suitable for specific treatment.

BACKGROUND OF THE INVENTION

Many disease states are characterized by differences in the expression levels of various genes, either through changes in the copy number of the genetic DNA or through changes in levels of transcription of particular genes (e.g., through control of initiation, provision of RNA precursors, RNA processing, etc.). Cancer testis antigens (CTA) are a large family of tumor-associated antigens expressed in human tumors of different histological origin, but not in normal tissues except for testis and placenta. At the present time, however, there are few reliable diagnostic markers in clinical use for the diagnosing or determining the severity of various types of tumors or cancers.

SUMMARY OF THE INVENTION

According to some embodiments, there is provided a method and a kit for determining a cancer testis antigen (CTA) signature in a non-testis biological sample. In one embodiment, said CTA signature is indicative of a proliferation state of a cell such as cancerous state. In another embodiment, said CTA signature is indicative of a pluripotency state of a cell.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A-J are graphs showing the expression signature for each of the 10 CTAs in 449 non-cancerous samples (NC) and 2155 cancerous samples (Cancer). FIG. 1K is a graph showing the sum expression signature of the 10 CTAs in 449 non-cancerous samples (presented on the x axis by the nos. 1-449) and 2155 cancerous samples (presented on the x axis by the nos. 1 450-2655). FIG. 1L is a ROC curve based on the sum folds increase of the 10 selected CTAs.

FIG. 3A is a bar graph comparing the sum of the expression of the 3 genes MAGEB4, TTK and SLCO6A1 in 4 normal liver (control) samples and in 45 liver cancer samples. FIG. 3B is a ROC curve based on the sum of fold increases of the selected CTAs (MAGEB4, TTK and SLCO6A1). FIG. 3C is a ROC curve based on the sum of fold increases in expression of: TTK, PBK, CEP55, ZNF165, ATAD2, SPAG1, MAGEA6, and GAGE12D.

FIG. 6A is a graph showing the sum of expression of the 4 genes: RBM46, CT47A1/A2/A3/A4/A5/A6/A8/A9/A10/A7/7A11, PBK, and DDX53 in 2 normal samples (Control) followed by 353 breast cancer samples. FIG. 6B is a ROC curve based on the sum of fold increases in expression of the four CTA genes.

FIG. 7A is a graph showing the sum of expression of: CEP55, GAGE8/12F, SPAG4, LOC653786/OTOA and CTNNA2 in 9 normal samples (control) followed by 281 kidney cancer samples. FIG. 7B is a ROC curve based on the sum of fold increases in expression of the CTA genes CEP55, GAGE8/12F, SPAG4, LOC653786/OTOA and CTNNA2.

FIG. 8A is a graph showing the sum expression of: PBK, MORC1, XAGE1B/1E, BAGE2/3/5/KMT2C and IL13RA2, in 3 normal samples (control) followed by 129 lung cancer samples. FIG. 8B is a ROC curve based on the sum folds increase in expression of the CTA genes PBK, MORC1, XAGE1B/1E, BAGE2/3/5/KMT2C and IL13RA2.

FIG. 9A is a graph showing the sum expression of: ZNF165, PRAME, GAGE1 and GAGE12F/12G/12I/7/5 in 5 normal samples (control) followed by 204 ovarian cancer samples. FIG. 9B is a ROC curve based on the sum folds increase in expression of the CTA genes. ZNF165, PRAME, GAGE1 and GAGE12F/12G/12I/7/5.

FIG. 10B is a ROC curve based on the sum folds increase in expression of the CTA genes MAGEA12, SPAG4 and ELOVL4. FIG. 10C is a bar graph demonstrating correlation between increase in a value of the sum fold increase of PBK, MAGEA12, SPAG4 and ELOVL4 and adrenal cancer stage/severity. The bars represent: normal individuals (Control), adenocarcinoma (AD) and lower grade adenoid cystic carcinoma (LG-ACC) followed by high grade adenoid cystic carcinoma (HG-ACC).

FIG. 14A is a graph showing sum expression of FAM133A, MORC1, TEX14, ANKRD45, MAGEB2, MAGEC1 and ELOVL4 in 5 normal (control) followed by 41 multiple myeloma patients. FIG. 14B is a ROC curve based on the sum of fold increases in expression of the CTA genes: FAM133A, MORC1, TEX14, ANKRD45, MAGEB2, MAGEC1 and ELOVL4. FIG. 14C is a bar graph demonstrating correlation between the sum of expression of FAM133A, MORC1, TEX14, ANKRD45, MAGEB2, MAGEC1 and ELOVL4 and multiple myeloma stage/severity. The bars represent: normal individuals (control), monoclonal gammopathy of undetermined significance (MGUS), smoldering multiple myeloma (SMM) and multiple myeloma (MM).

FIG. 15A is a graph showing sum expression of: PRAME and CTNNA2 in 16 normal samples (control) followed by 46 melanoma samples. FIG. 15B is a ROC curve based on the sum of fold increases in expression of the CTA genes PRAME and CTNNA2. FIG. 15C is a graph showing sum expression of: DDX43, SSX1, ATAD2 and CEP55 in 18 normal samples (control) followed by 11 uveal melanoma samples.

FIGS. 17A-17B: FIG. 17A is a graph showing sum expression of: TDRD1, POTED, DCAF12 and TSGA10, in 14 non-cancerous samples followed by 36 prostate cancer samples. FIG. 17B is a ROC curve based on the sum folds increase in expression of the CTA genes: TDRD1, POTED, DCAF12 and TSGA10.

FIGS. 18A-18C: FIG. 18A is a graph showing sum expression of: IL13RA2, ZNF165, CEP55, CTAG2, SPAG4, MORC1 and SPAG8 in 24 non-cancerous samples (Control) followed by 50 glioblastoma samples. FIG. 18B is a ROC curve based on the sum of fold increases in expression of the CTA genes IL13RA2, ZNF165, CEP55, CTAG2, SPAG4, MORC1 and SPAG8. FIG. 18C is a bar graph demonstrating correlation between increase in a value of the sum folds increase of IL13RA2, ZNF165, CEP55, CTAG2, SPAG4, MORC1 and SPAG8 and glioblastoma stage/severity. The bars represent: Glioblastoma grade III (GBM III), Glioblastoma grade IV-uncharacterized (GBM-IV), Glioblastoma grade IV-without necrosis (GBM-IV-WN), Glioblastoma grade IV-with necrosis (GBM-IV-N).

DETAILED DESCRIPTION OF THE INVENTION

Figure 1A:
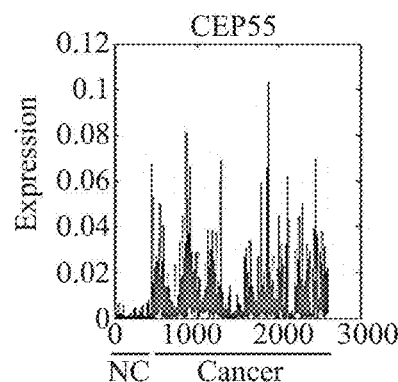
FIGS. 1A-1L.
Figure 1E:
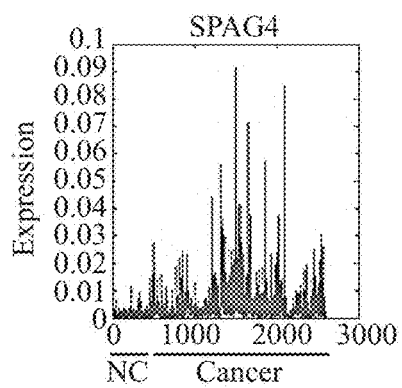
Figure 1B:
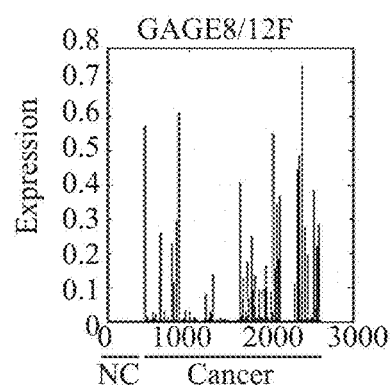
Figure 1F:
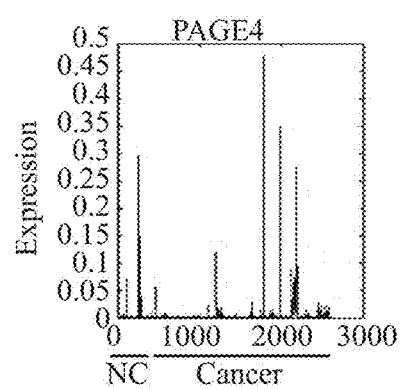
Figure 1C:
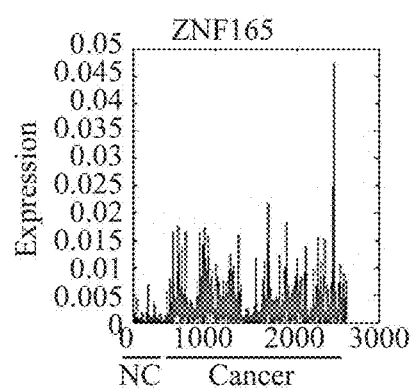
Figure 1G:
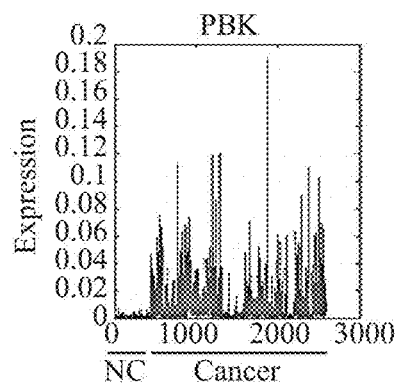
Figure 1D:
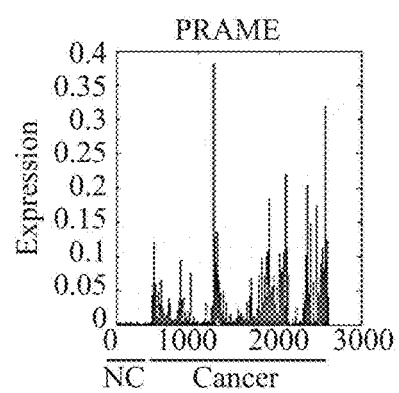
Figure 1H:
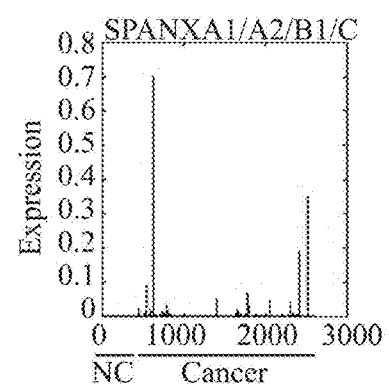
Figure 1I:
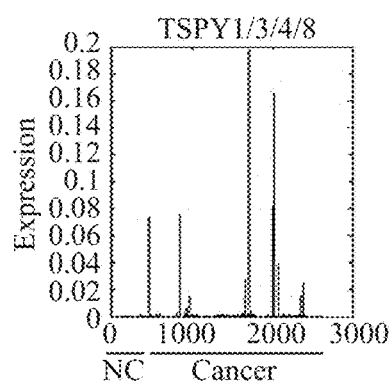
Figure 1J:
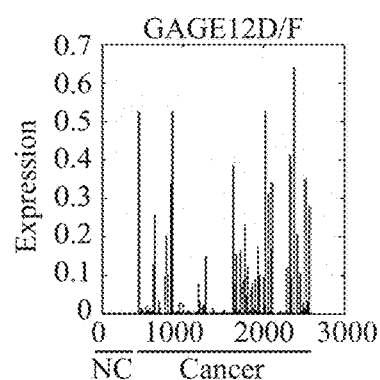

The present invention, in some embodiments, provides a method and a kit for the diagnosis and treatment evaluation of cancer, based on specific expression profiles of Cancer Testis Antigens (CTA).

The invention provides methods and kits for utilizing the expression profile of a set of CTA genes for determining the proliferation state of a cell, in high accuracy. In some embodiments, the methods and kits of the present invention enable discriminating cancer patients from normal controls as well as enabling cancer staging and monitoring with high accuracy, sensitivity and specificity.

The present invention is based, in part, on the finding that a large variety of cancers (over 150 types of cancer) exhibit increased expression of a particular set of antigens comprising: CEP55, GAGE8/12F, ZNF165, PRAME, SPAG4, PAGE4, PBK, SPANXA2/B1/C/A1, TSPY8/4/3/1, and GAGE12D/12F (termed herein: "cell proliferation signature"). As exemplified hereinbelow, increased expression of a plurality of genes selected from the cell proliferation signature of the invention, compared to a reference value, enables discrimination of cancer patients from normal controls (e.g., non-cancerous individuals) with high accuracy, sensitivity and specificity.

According to one aspect, there is provided a method for determining a cancer testis antigen (CTA) signature in a non-testis biological sample, the method comprises the steps of:

(a) determining an expression profile of a plurality of antigens selected from the group consisting of: CEP55, GAGE8/GAGE12F, ZNF165, PRAME, SPAG4, PAGE4, PBK, SPANXA2/SPANXB1/SPANXC/SPANXA1, TSPY8/TSPY4/TSPY3/TSPY1, and GAGE12D/GAGE12F, in the non-testis biological sample obtained from a subject; and (b) comparing the expression profile to a reference expression profile, thereby determining the CTA signature in the non-testis biological sample.

In one embodiment, the CTA signature is indicative of a proliferation state of a cell, wherein an increase in expression of the expression profile compared to the reference expression profile is indicative of an increased cell proliferation state. In one embodiment, the increased cell proliferation state is a cancerous state.

In another embodiment, the CTA signature is indicative of a pluripotency state in a cell, wherein an increase in expression of the expression profile compared to the reference expression profile is indicative of an increased cell pluripotency state.

As exemplified hereinbelow, (i) an elevation of a plurality of antigens selected from: RBM46, CT47A1/2/3/4/5/6/7/8/9/10/11, PBK, and DDX53, as compared to reference values, is indicative of breast cancer, (ii) an elevation of a plurality of antigens selected from: SLCO6A1 and CEP55, or MAGEB4, TTK, and SLCO6A1, as compared to reference values, is indicative of liver cancer, (iii) an elevation of a plurality of antigens selected from: FAM133A, MORC1, TEX14, ANKRD45, MAGEB2, MAGEC1 and ELOVL4, as compared to reference values, is indicative of multiple myeloma, (iv) an elevation of a plurality of antigens selected from: IL13RA2, ZNF165, CEP55, CTAG2, SPAG4, MORC1 and SPAG8, as compared to reference values, is indicative of glioblastoma, (v) an elevation of a plurality of antigens selected from: MAGEA11, ODF2, IL13RA2, MAGEA6, DDX43, CEP55, MAGEA1, MAGEB3, SPANXB1, BAGE and TSGA10, as compared to reference values is indicative of colon cancer, (vi) an elevation of a plurality of antigens selected from: TDRD1, POTED, DCAF12 and TSGA10, as compared to reference values, is indicative of prostate cancer, (vii) an elevation of a plurality of antigens selected from: PRAME and CTNNA2, and optionally MAGEA3, MAGEA6, MAGEA5, MAGEA12, MAGEA1, HORMAD1, IGSF11, CASC5, ELVO4, MAGEA4, MAGEA11, ATAD2, OIP5, TTK, NOL4, LY6K, LEMD1, CABYR, PBK, CEP55, TMEFF1 and CTNNA2, as compared to reference values, is indicative of melanoma cancer, (viii) an elevation of a plurality of antigens selected from: ZNF165, PRAME, GAGE1 and GAGE12F/12G/12I/7/5, as compared to reference values, is indicative of ovarian cancer, (ix) an elevation of a plurality of antigens selected from: PBK, MAGEA12, SPAG4, ELOVL4, CEP55, TTK, ATAD2, OIP5, FAM133A, FATE1, IL13RA2, PRAME, MAGEA6, CTNNA2, MAGEA3, and PLAC1 as compared to reference values is indicative of adrenal cancer, (x) an elevation of a plurality of antigens selected from: CEP55, GAGE8/12F, SPAG4, LOC653786/OTOA, CTNNA2, TPTE, ATAD2, GAGE8/12F/2A/2D/12J/12G/2B/2E/12I/7/6/5/4/3/2C/1, MAGEA6, MORC1, TTK, PBK, RGS22, TMEFF1, ARX, MAGEB4, PRAME, GAGE12D/2F/2A/12H/12E/12C/12G/12I/7/6/5/4/2C, TEX14, POTED, DMRT1, CTCFL, GPAT2, GAGE12F/12G/2I/E7/E5, GAGE3, SPANXA2/C/A1, DDX43, and GAGE1, as compared to reference values, is indicative of kidney cancer, (xi) an elevation of a plurality of antigens selected from: DDX43, SSX1, ATAD2 and CEP55, as compared to reference values, is indicative of uveal melanoma cancer, and (xii) an elevation of a plurality of antigens selected from: LY6K, MAGEA6, PLAC1, LEMD1, MAGEA1, MAGEA11l, MAGEA4, MAGEA12, and CEP55, as compared to reference values, is indicative of oral squamous cell carcinoma.

It will be understood by one skilled in the art that when determining expression of a plurality of CTAs, any CTA described herein can be replaced with a correlated CTA (a CTA whose expression is correlated in a specific cancer) as described in Table 5. It will also be appreciated by a skilled artisan that various CTA genes belong to a multigene family (e.g., on one contiguous genomic sequence). CTAs belonging to a multigene family are referred to throughout the text with separating slashes "/". It will be appreciated that CTAs separated by slashes are interchangeable for the specific use (may be considered as clusters) wherein a single probe may recognize one or multiple potential target sequences.

The present invention is also based, in part, on the finding that various cancers as well as specific cancer stages or sub-groups, exhibit a characteristic expression profile of specific sets of CTAs. As exemplified hereinbelow, differences of expression levels of a specific expression profile set of the invention, compared to a reference value, enables diagnosis of a cancer type, with higher accuracy, specificity, and sensitivity as compared to a single CTA or other sets of CTAs. Table 2 lists non-limiting CTA signatures for various cancers.

TABLE 2

| Tissue | CTA signature (NCBI Gene ID) |
| --- | --- |
| Cell proliferation signature | CEP55, (55165) |
| | GAGE8/GAGE12F, (100101629/100008586) |
| | ZNF165, (7718) |
| | PRAME, (23532) |
| | SPAG4, (6676) |
| | PAGE4, (9506) |
| | PBK, (55872) |
| | SPANXA2/SPANXB1/SPANXC/SPANXA1, (728712/728695/64663/30014) |
| | TSPY8/TSPY4/TSPY3/TSPY1, (728403/728395/728137/7258) |
| | GAGE12D/GAGE12F (100132399/100008586) |
| Breast cancer | RBM46, (166863) |
| | CT47A1/CT47A2/CT47A3/CT47A4/CT47A5/CT47A6/CT47A7/CT47A8/CT47A9/CT47A10/CT47A11, (728096/728090/728082/728075/728072/728062/653282/728049/728042/728036/25513) |
| | PBK, (55872) |
| | DDX53, (168400) |
| | MAGEB3, (4114) |
| | LOC653786/OTOA, (653786/146183) |
| | DMRT1, (1761) |
| | LDHC, (3948) |
| | CCDC83, (220047) |
| | ANKRD45, (339416) |
| | DDX53, (168400) |
| | BAGE, (574) |
| | TDRD1, (56165) |
| | CEP55, (55165) |
| | PRM1, (5619) |

TABLE 2-continued

| Tissue | CTA signature (NCBI Gene ID) |
|---|---|
| | SSX2B/SSX2, (727837/6757) |
| | SEMG1, (6406) |
| | TPTE (7179) |
| Liver cancer | MAGEB4, (4115) |
| | SLCO6A1, (133482) |
| | PBK, (55872) |
| | SPA17, (53340) |
| | ATAD2, (29028) |
| | FAM133A, (286499) |
| | TTK, (7272) |
| | MAGEA1, (4100) |
| | OIP5, (11339) |
| | CABYR, (26256) |
| | SSX1, (6756) |
| | MAGEA3, (4102) |
| | SSX2B/SSX2, (727837/6757) |
| | MAGEA6, (4105) |
| | MAGEA12, (4111) |
| | CTNNA2, (1496) |
| | TPTE, (7179) |
| | SSX4B/SSX4, (548313/6759) |
| | XAGE1B/XAGE1E, (653220/653067) |
| | MAGEC1, (9947) |
| | GAGE8/GAGE12F/GAGE2A/GAGE2D/GAGE12J/GAGE12G/GAGE2B/GAGE2E/ |
| | GAGE12I/GAGE7/GAGE6/GAGE5/GAGE4/GAGE3/GAGE2C/GAGE1, |
| | (100101629/100008586/729447/729408/729396/645073/645037/26749/26748/2579/4578/ |
| | 2577/2576/2575/2574/2543)/ |
| | GAGE12D/GAGE12F/GAGE2A/GAGE12H/GAGE12E/GAGE12C/GAGE12G/ |
| | GAGE12I/GAGE7/GAGE6/GAGE5/GAGE4/GAGE2C, |
| | (100132399/100008586/729447/729442/729431/729442/645073/26748/2579/4578/2577/ |
| | 2576/2575/2574) |
| Multiple myeloma | FAM133A, (286499) |
| | MORC1, (27136) |
| | TEX14, (56166) |
| | ANKRD45, (339416) |
| | MAGEB2, (4113) |
| | MAGEC1 (9947 |
| | ELOVL4 (6785) |
| Glioblastoma | IL13RA2, (3598) |
| | ZNF165, (7718) |
| | CEP55, (55165) |
| | CTAG2, (30848) |
| | SPAG4, (6676) |
| | MORC1 (27136) |
| | SPAG8 (26206) |
| Colon cancer | MAGEA11, (4110) |
| | ODF2, (4957) |
| | IL13RA2, (3498) |
| | MAGEA6, (4105) |
| | DDX43, (55510) |
| | CEP55, (55165) |
| | MAGEA1, (4100) |
| | MAGEB3, (4114) |
| | SPANXB1, (728695) |
| | BAGE, (574) |
| | TSGA10, (80705) |
| | MAGEA3, (4102) |
| | MAGEA12, (4111) |
| | IL13RA2 (3598) |
| Adrenal cancer | CEP55, (55165) |
| | TTK, (7272) |
| | ATAD2, (29028) |
| | OIP5, (11339) |
| | FAM133A, (286499) |
| | FATE1, (89885) |
| | IL13RA2, (3598) |
| | PRAME, (23532) |
| | MAGEA6, (4105) |
| | CTNNA2, (1496) |
| | MAGEA3, (4102) |
| | PLAC1, (10761) |
| | PBK, (55872) |
| | MAGEA12, (4111) |
| | SPAG4 (6676) |
| | ELOVL4 (6785) |

TABLE 2-continued

| Tissue | CTA signature (NCBI Gene ID) |
|---|---|
| Melanoma | PRAME, (23532)<br>CTNNA2, (1496)<br>MAGEA2B/MAGEA2, (266740/4101)<br>TMEFF1, (8577)<br>IGSF11, (152404)<br>MAGEA3, (4102)<br>SSX1, (6756)<br>MAGEA6, (4105)<br>MAGEA12, (4111)<br>PBK, (55872)<br>ANKRD45, (339416)<br>SSX4B/SSX4, (548313/6759)<br>MAGEC1, (9947)<br>SSX2B/SSX2, (727837/6757)<br>MAGEA1, (4100)<br>MAGEC2, (51438)<br>DSCR8, (84677)<br>TTK, (7272)<br>CTAG1A/CTAG1B, (246100/1485)<br>TPTE, (7179)<br>XAGE1B/XAGE1E (653220/653067)<br>IL13RA2 (3598) |
| Ovarian cancer | SPAG1, (6674)<br>TTK, (7272)<br>LEMD1, (93273)<br>SPA17, (53340)<br>PBK, (55872)<br>TMEFF1, (8577)<br>CEP55, (55165)<br>CTNNA2, (1496)<br>SPAG4, (6676)<br>CTCFL, (140690)<br>SPAG17, (200162)<br>BAGE, (574)<br>ATAD2, (29028)<br>PRSS54, (221191)<br>GPAT2, (150763)<br>CCDC83, (220047)<br>MAGEA11, (4110)<br>CT45A2/CT45A1/CT45A6/CT45A5/CT45A4/CT45A3, (728911/541466/541465/<br>441521/441519/441519)<br>LY6K, (54742)<br>TSGA10, (80705)<br>DSCR8, (84677)<br>CTAG1A/CTAG1B, (246100/1485)<br>SAGE1, (55511)<br>ZNF165, (7718)<br>PRAME, (23532)<br>GAGE1 (2543)<br>GAGE12F/GAGE12G/GAGE12I/GAGE7/GAGE5 (100008586/645073/26748/2579/<br>2577) |
| Prostate cancer | TDRD1, (56165)<br>POTED, (317754)<br>DCAF12 (25853)<br>TSGA10 (80705) |
| Kidney cancer | CEP55, (55165)<br>GAGE8/GAGE12F, (100101629/100008586)<br>SPAG4, (6676)<br>LOC653786/OTOA, (653786/146183)<br>CTNNA2, (1496)<br>TPTE, (7179)<br>ATAD2, (29028)<br>GAGE8/GAGE12F/GAGE2A/GAGE2D/GAGE12J/GAGE12G/GAGE2B/GAGE2E/<br>GAGE12I/GAGE7/GAGE6/GAGE5/GAGE4 AGE3/GAGE2C/GAGE1, (100101629/<br>100008586/729447/729408/729396/645073/645037/26749/26748/2579/2578/2577/<br>2576/2575/2574/2543)<br>MAGEA6, (4105)<br>MORC1, (27136)<br>TTK, (7272)<br>PBK, (55872)<br>RGS22, (26166)<br>TMEFF1, (8577)<br>ARX, (170302)<br>MAGEB4, (4115)<br>PRAME, (23532)<br>GAGE12D/GAGE12F/GAGE2A/GAGE12H/GAGE12E/GAGE12C/GAGE12G/<br>GAGE12I/GAGE7/GAGE6/GAGE5/GAGE4/GAGE2C, TEX14, POTED, DMRT1,<br>CTCFL, GPAT2, GAGE12F/GAGE12G/GAGE12I/GAGE7/GAGE5, (100132399/ |

TABLE 2-continued

| Tissue | CTA signature (NCBI Gene ID) |
|---|---|
| | 100008586/729447/729442/729431/729422/645073/26748/2579/2578/2577/2576/<br>2574/56155/317754/1761/140690/150763/100008586/645073/26748/2579/2577)<br>GAGE3, (2575)<br>SPANXA2/SPANXC/SPANXA1, (728712/64663/30014)<br>DDX43, (55510)<br>GAGE1 (2543) |
| Uveal<br>melanoma | DDX43, (55510)<br>SSX1, (6756)<br>ATAD2, (29028)<br>CEP55 (55165) |
| Oral<br>squamous<br>cell<br>carcinoma | LY6K, (54742)<br>MAGEA6, (4105)<br>PLAC1, (10761)<br>LEMD1, (93273)<br>MAGEA1, (4100)<br>MAGEA11, (4110)<br>MAGEA4, (4103)<br>MAGEA12, (4111)<br>CEP55 (55165) |

According to another aspect, there is provided a method for diagnosing, prognosticating, monitoring or determining severity of cancer in a subject, the method comprises the steps of:

(a) determining an expression profile of a plurality of antigens listed in a table selected from Table 2, in a non-testis biological sample obtained from a subject; and (b) comparing said expression profile to a reference expression profile, wherein:

(i) an increase in expression of an expression profile of a plurality of antigens selected from the group consisting of: RBM46, CT47A1/A2/A3/A4/A5/A6/A8/A9/A10/A7/A11, PBK, DDX53, MAGEB3, LOC653786/OTOA, DMRT1, LDHC, CCDC83, ANKRD45, DDX53, BAGE, TDRD1, CEP55, PRM1, SSX2B/2, SEMG1, and TPTE, compared to said reference is indicative of breast cancer, (ii) an increase in expression of an expression profile of a plurality of antigens selected from the group consisting of: MAGEB4, TTK, CEP55, SLCO6A1, PBK, SPA17, ATAD2, FAM133A, TTK, MAGEA1, OIP5, CABYR, SSX1, MAGEA3, SSX2B/2, MAGEA6, MAGEA12, CTNNA2, TPTE, SSX4B/4, XAGE1B/1E, MAGEC1, GAGE8/12F/2A/2D/12J/12G/2B/2E/12I/7/6/E5/4/3/2C/1, GAGE12D/12F/2A/12H/12E/12C/12G/12I/7/6/5/4/2C, and GAGE12F/12G/12I/7/5 is indicative of liver cancer, (iii) an increase in expression of an expression profile of a plurality of antigens selected from the group consisting of: FAM133A, MORC1, TEX14, ANKRD45, MAGEB2, MAGEC1 and ELOVL4, is indicative of multiple myeloma, (iv) an increase in expression of an expression profile of a plurality of antigens selected from: IL13RA2, ZNF165, CEP55, CTAG2, SPAG4, MORC1 and SPAG8, is indicative of glioblastoma, (v) an increase in expression of an expression profile of a plurality of antigens selected from the group consisting of: MAGEA11, ODF2, IL13RA2, MAGEA6, DDX43, CEP55, MAGEA1, MAGEB3, SPANXB1, BAGE, TSGA10, MAGEA3, MAGEA12, MAGEA1, and IL13RA2, is indicative of colon cancer, (vi) an increase in expression of an expression profile of a plurality of antigens selected from the group consisting of: PBK, MAGEA12, SPAG4, ELOVL4, CEP55, TTK, ATAD2, OIP5, FAM133A, FATE1, IL13RA2, PRAME, MAGEA6, CTNNA2, MAGEA3, PLAC1, is indicative of adrenal cancer, (vii) an increase in expression of an expression profile of a plurality of antigens selected from the group consisting of: PRAME, CTNNA2, MAGEA2B/2, TMEFF1, IGSF11, MAGEA3, SSX1, MAGEA6, MAGEA12, PBK, ANKRD45, SSX4B/4, MAGEC1, SSX2B/2, MAGEA1, MAGEC2, DSCR8, TTK, CTAG1A/B, TPTE, XAGE1B/1E and IL13RA2, is indicative of melanoma cancer, (viii) an increase in expression of an expression profile of a plurality of antigens selected from the group consisting of: ZNF165, PRAME, GAGE1, GAGE12F/G/I/7/5, SPAG1, TTK, LEMD1, SPA17, PBK, TMEFF1, CEP55, CTNNA2, SPAG4, CTCFL, SPAG17, BAGE, ATAD2, PRSS54, GPAT2, CCDC83, MAGEA11, CT45A2/A1/A6/A5/A4/A3, LY6K, TSGA10, DSCR8, CTAG1A/CTAG1B, and SAGE1 is indicative of ovarian cancer, (ix) an increase in expression of an expression profile of a plurality of antigens selected from the group consisting of: TDRD1, POTED, DCAF12 and TSGA10 is indicative of prostate cancer, (x) an increase in expression of an expression profile of a plurality of antigens selected from the group consisting of: CEP55, GAGE8/12F, SPAG4, LOC653786/OTOA, CTNNA2, TPTE, ATAD2, GAGE8/12F/2A/2D/12J/12G/2B/2E/12I/7/6/5/4/3/2C/1, MAGEA6, MORC1, TTK, PBK, RGS22, TMEFF1, ARX, MAGEB4, PRAME, GAGE12D/2F/2A/12H/12E/12C/12G/12I/7/6/5/4/2C, TEX14, POTED, DMRT1, CTCFL, GPAT2, GAGE12F/12G/2I/E7/E5, GAGE3, SPANXA2/C/A1, DDX43, and GAGE1, is indicative of kidney cancer;

(xi) an increase in expression of an expression profile of a plurality of antigens selected from the group consisting of: DDX43, SSX1, ATAD2 and CEP55 is indicative of uveal melanoma; and (xii) an increase in expression of an expression profile of a plurality of antigens selected from the group consisting of: LY6K, MAGEA6, PLAC1, LEMD1, MAGEA1, MAGEA11, MAGEA4, MAGEA12, and CEP55 is indicative of oral squamous cell carcinoma;

thereby determining a cancerous state in said subject.

According to another aspect, there is provided a method for diagnosing, prognosticating, monitoring or determining severity of cancer in a subject, the method comprises the steps of:
(a) determining an expression profile of a plurality of CT antigens selected from: ZNF165, GAGE1, PRAME, GAGE12, PBK, XAGE1B, IL13RA2, MORC1, BAGE2, CEP55, SPAG4, CTNNA2, GAGE8, OTOA, RBM46, DDX53, CT47A1, TDRD1, DCAF12, POTED, TSGA10, MAGEB4, TTK, SLCO6A1, FAM133A, ANKRD45, ELOVL4, MAGEB2, TEX14, MAGEC1, MAGEA12, DDX43, SSX1, ATAD2, LY6K, MAGEA6, PLAC1, and LEMD1 in a non-testis biological sample obtained from a subject; and
(b) comparing said expression profile to a reference expression profile of said CT antigens, wherein:
 (i) an increase in expression of an expression profile of a plurality of CT antigens selected from the group consisting of: ZNF165, GAGE1, PRAME, and GAGE12, as compared to said reference is indicative of ovarian cancer,
 (ii) an increase in expression of an expression profile of a plurality of CT antigens selected from the group consisting of: PBK, XAGE1B, IL13RA2, MORC1, and BAGE2, as compared to said reference is indicative of lung cancer,
 (iii) an increase in expression of an expression profile of a plurality of CT antigens selected from the group consisting of: CEP55, SPAG4, CTNNA2, GAGE8, and OTOA, as compared to said reference is indicative of kidney cancer,
 (iv) an increase in expression of an expression profile of a plurality of CT antigens selected from the group consisting of: RBM46, DDX53, and CT47A1, as compared to said reference is indicative of breast cancer,
 (v) an increase in expression of an expression profile of a plurality of CT antigens selected from the group consisting of: TDRD1, DCAF12, POTED, and TSGA10, as compared to said reference is indicative of prostate cancer,
 (vi) an increase in expression of an expression profile of a plurality of CT antigens selected from the group consisting of: MAGEB4, TTK, and SLCO6A1, as compared to said reference is indicative of liver cancer,
 (vii) an increase in expression of an expression profile of a plurality of CT antigens selected from the group consisting of: PRAME and CTNNA2, as compared to said reference is indicative of melanoma,
 (viii) an increase in expression of an expression profile of a plurality of CT antigens selected from the group consisting of: FAM133A, ANKRD45, ELOVL4, MORC1, MAGEB2, TEX14, MAGEC1, as compared to said reference is indicative of multiple myeloma,
 (ix) an increase in expression of an expression profile of a plurality of CT antigens selected from the group consisting of: TTK and PRAME, as compared to said reference is indicative of lung cancer,
 (x) an increase in expression of an expression profile of a plurality of CT antigens selected from the group consisting of: PBK, SPAG4, MAGEA12, and ELOVL4, as compared to said reference is indicative of adrenal carcinoma,
 (xi) an increase in expression of an expression profile of a plurality of CT antigens selected from the group consisting of: DDX43, SSX1, ATAD2 and CEP55 as compared to said reference is indicative of uveal melanoma, and
 (xii) an increase in expression of an expression profile of a plurality of CT antigens selected from the group consisting of: LY6K, MAGEA6, PLAC1, LEMD1, MAGEA12, and CEP55, as compared to said reference is indicative of oral squamous cell carcinoma.

According to another aspect, there is provided a method for determining a cancer testis antigen (CTA) signature in a non-testis biological sample, the method comprises the steps of:
(a) determining an expression profile of a plurality of antigens listed in a table selected from Table 2, in a non-testis biological sample obtained from a subject; and
(b) comparing said expression profile to a reference expression profile, wherein:
 (i) an increase in expression of an expression profile of a plurality of antigens selected from the group consisting of: RBM46, CT47A1/A2/A3/A4/A5/A6/A8/A9/A10/A7/A11, PBK, DDX53, MAGEB3, LOC653786/OTOA, DMRT1, LDHC, CCDC83, ANKRD45, DDX53, BAGE, TDRD1, CEP55, PRM1, SSX2B/2, SEMG1, and TPTE, compared to said reference is indicative of a breast CTA signature,
 (ii) an increase in expression of an expression profile of a plurality of antigens selected from the group consisting of: MAGEB4, TTK, CEP55, SLCO6A1, PBK, SPA17, ATAD2, FAM133A, TTK, MAGEA1, OIP5, CABYR, SSX1, MAGEA3, SSX2B/2, MAGEA6, MAGEA12, CTNNA2, TPTE, SSX4B/4, XAGE1B/1E, MAGEC1, GAGE8/12F/2A/2D/12J/12G/2B/2E/12I/7/6/E5/4/3/2C/1, GAGE12D/12F/2A/12H/12E/12C/12G/12I/7/6/5/4/2C, and GAGE12F/12G/12I/7/5 is indicative of a liver CTA signature,
 (iii) an increase in expression of an expression profile of a plurality of antigens selected from the group consisting of: FAM133A, MORC1, TEX14, ANKRD45, MAGEB2, MAGEC1 and ELOVL4, is indicative of a plasma cell CTA signature,
 (iv) an increase in expression of an expression profile of a plurality of antigens selected from: IL13RA2, ZNF165, CEP55, CTAG2, SPAG4, MORC1 and SPAG8, is indicative of a glial cell CTA signature,
 (v) an increase in expression of an expression profile of a plurality of antigens selected from the group consisting of: MAGEA11, ODF2, IL13RA2, MAGEA6, DDX43, CEP55, MAGEA1, MAGEB3, SPANXB1, BAGE, TSGA10, MAGEA3, MAGEA12, MAGEA1, and IL13RA2, is indicative of a colon CTA signature,
 (vi) an increase in expression of an expression profile of a plurality of antigens selected from the group consisting of: PBK, MAGEA12, SPAG4, ELOVL4, CEP55, TTK, ATAD2, OIP5, FAM133A, FATE1, IL13RA2, PRAME, MAGEA6, CTNNA2, MAGEA3, PLAC1, is indicative of an adrenal CTA signature,
 (vii) an increase in expression of an expression profile of a plurality of antigens selected from the group consisting of: PRAME, CTNNA2, MAGEA2B/2, TMEFF1, IGSF11, MAGEA3, SSX1, MAGEA6, MAGEA12, PBK, ANKRD45, SSX4B/4, MAGEC1, SSX2B/2, MAGEA1, MAGEC2, DSCR8, TTK, CTAG1A/B, TPTE, XAGE1B/1E and IL13RA2, is indicative of a melanocytes CTA signature, (viii) an increase in expression of an expression profile of a plurality of antigens selected from the group consisting of: ZNF165, PRAME, GAGE1, GAGE12F/G/I/7/5, SPAG1, TTK, LEMD1, SPA17, PBK, TMEFF1, CEP55, CTNNA2, SPAG4, CTCFL, SPAG17, BAGE, ATAD2, PRSS54, GPAT2, CCDC83, MAGEA11, CT45A2/A1/A6/A5/A4/A3, LY6K, TSGA10, DSCR8, CTAG1A/CTAG1B, and SAGE1 is indicative of a ovarian CTA signature, (ix) an increase in expression of an expression profile of a plurality of antigens selected from the group consisting of: TDRD1, POTED, DCAF12 and TSGA10 is indicative of a prostate CTA signature, (x) an increase in expression of an expression profile of a plurality of antigens selected from the group consisting of: CEP55, GAGE8/12F, SPAG4, LOC653786/0TOA, CTNNA2, TPTE, ATAD2, GAGE8/12F/2A/2D/12J/12G/2B/2E/12I/7/6/5/4/3/2C/1, MAGEA6, MORC1, TTK, PBK, RGS22, TMEFF1, ARX, MAGEB4, PRAME, GAGE12D/2F/2A/12H/12E/12C/12G/12I/7/6/5/4/2C, TEX14, POTED, DMRT1, CTCFL, GPAT2, GAGE12F/12G/2I/E7/E5, GAGE3, SPANXA2/C/A1, DDX43, and GAGE1, is indicative of a kidney CTA signature;

(xi) an increase in expression of an expression profile of a plurality of antigens selected from the group consisting of: DDX43, SSX1, ATAD2 and CEP55 is indicative of a uveal melanocytes CTA signature; and (xii) an increase in expression of an expression profile of a plurality of antigens selected from the group consisting of: LY6K, MAGEA6, PLAC1, LEMD1, MAGEA1, MAGEA11, MAGEA4, MAGEA12, and CEP55 is indicative of a squamous cell CTA signature;

thereby determining the CTA signature in the non-testis biological sample.

As used herein, the term "sensitivity", refers to the proportion of cancer individuals, i.e., actual positives, who are correctly identified by the methods of the invention as such. The term "specificity", as used herein, refers to the proportion of non-cancer individuals, i.e., healthy individuals or individuals suffering from diseases, disorders or conditions other than cancer, who are incorrectly identified by the methods of the invention as such. The term "accuracy", as used herein, means a statistical measure for the correctness of classification or identification of sample types. The accuracy is the proportion of true results (both true positives and true negatives).

In some embodiments, the contacting is performed in-vitro or ex-vivo. In some embodiments, the contacting is performed in-situ (i.e., in a subject's body). Methods of in-situ determination of a cancerous state may also be used for theranostics (e.g., the detecting agent being used also for treatment).

In some embodiments, the method further comprises the step of comparing the expression profile to a reference expression profile. In some embodiments, an increase in expression of the expression profile compared to the reference expression profile is indicative of cancer in said subject.

In some embodiments, the CTA signature is selected from the group consisting of: CEP55, GAGE8/12F, ZNF165, PRAME, SPAG4, PAGE4, PBK, SPANXA2/B1/C/A1, TSPY8/4/3/1, and GAGE12D/12F. In some embodiments, the CTA signature is selected from the group consisting of: RBM46, CT47A1/A2/A3/A4/A5/A6/A8/A9/A10/A7/A11, PBK, and DDX53. In some embodiments, the CTA signature is selected from the group consisting of: FAM133A, MORC1, TEX14, ANKRD45, MAGEB2, MAGEC1 and ELOVL4. In some embodiments, the CTA signature is selected from the group consisting of: MAGEA11, ODF2, IL13RA2, MAGEA6, DDX43, CEP55, MAGEA1, MAGEB3, SPANXB1, BAGE and TSGA10. In some embodiments, the CTA signature is selected from the group consisting of: ZNF165, PRAME, GAGE1 and GAGE12F/12G/12I/7/5.

In some embodiments, the CTA signature is selected from the group consisting of: CEP55, GAGE8, GAGE12F, ZNF165, PRAME, SPAG4, PAGE4, PBK, SPANXA2, SPANXB1, SPANXC, SPANXA1, TSPY8, TSPY4, TSPY3, TSPY1, GAGE12D, RBM46, CT47A1, CT47A2, CT47A3, CT47A4, CT47A5, CT47A6, CT47A8, CT47A9, CT47A10, CT47A7, CT47A11, DDX53, MAGEB3, LOC653786, OTOA, DMRT1, LDHC, CCDC83, ANKRD45, BAGE, TDRD1, PRM1, SSX2B, SSX2, SEMG1, TPTE, SPAG1, SPA17, ATAD2, FAM133A, TTK, MAGEA1, OIP5, CABYR, SSX1, MAGEA3, MAGEA6, MAGEA12, CTNNA2, SSX4B, SSX4, XAGE1B, XAGE1E, MAGEC1, GAGE2A, GAGE2D, GAGE12J, GAGE12G, GAGE2B, GAGE2E, GAGE12I, GAGE7, GAGE6, GAGE5, GAGE4, GAGE3, GAGE2C, GAGE1, GAGE12H, GAGE12E, GAGE12C, GAGE12F, GAGE12G, MORC1, TEX14, MAGEB2, ELOVL4, MAGEA11, ODF2, IL13RA2, DDX43, TSGA10, FATE1, MAGEA2B, MAGEA2, TMEFF1, IGSF11, MAGEC2, CTAG1A, CTAG1B, LEMD1, SPA17, TMEFF1, CTCFL, SPAG17, PRSS54, GPAT2, CCDC83, CT45A2, CT45A1, CT45A6, CT45A5, CT45A4, CT45A3, LY6K, DSCR8, and SAGE1.

According to another aspect, the invention provides a method for determining a cancerous state in a subject, the method comprises the steps of:

(a) determining an expression profile of a plurality of antigens, in a non-testis biological sample obtained from a subject; and (b) comparing the expression profile to a reference expression profile, wherein an increase in expression of the expression profile compared to the reference expression profile is indicative of cancer in said subject, thereby determining a cancerous state in said subject.

According to another aspect, the invention provides a method of treating a cancerous state in a subject, the method comprises the steps of:

(a) determining an expression profile of a plurality of antigens, in a non-testis biological sample obtained from a subject, as described herein;

(b) comparing the expression profile to a reference expression profile; and (c) administering an anti-cancer therapeutic or preventive treatment to the subject when an increase in expression of the expression profile compared to the reference expression profile is indicative of cancer in said subject, thereby treating a cancerous state in said subject.

In some embodiments, the cancerous state is selected from the presence of cancer, a type of cancer, a stage of a cancer, or a prognosis of a cancer. In some embodiments, the method is for detecting a specific type of cancer. In some embodiments, the method is for determining a stage of cancer. In some embodiments, the method is for cancer prognosis. In some embodiments, the method is for monitoring cancer progression and/or regression.

In some embodiments, the plurality of antigens comprises at least 3, 4, 5, 6, 7, 8, 9, 10, 11, 12, 13, 14, 15, 16, 17, 18, 19, 20, 21, 22, 23, 24, 25, 26, 27, 28, 29, 30, or 31 antigens. Each possibility represents a separate embodiment of the present invention. In some embodiments, the required plurality for high diagnosis accuracy varies for different applications (the different sets of expression profiles) of the methods of the invention.

As used herein, the term "subject" refers to any mammal, including both human and other mammals. In some embodiments, the methods of the present invention are applied to human subjects.

In some embodiments, the biological sample is obtained from a subject suspected to be affected by any type of cancer. Suitable samples include, but are not limited to, a cell, cell lysate, a protein sample, tissue, homogenized tissue, organ, homogenized organ, and bodily fluid. As will be appreciated by a skilled artisan, the method of collecting and preparing a sample from a subject can and will vary depending upon the nature of the sample. Any of a variety of methods generally known in the art may be utilized to collect a sample. Generally speaking, the method preferably maintains the integrity of the nucleic acid molecules such that they can accurately be detected and/or quantified in the sample.

In some embodiments, the biological sample is a bodily fluid including but not limited to whole blood, serum, plasma, cerebrospinal fluid, saliva, urine, spinal fluid, abdomen fluid, breast milk and lymphocyte or cell culture supernatants. In some embodiments, the biological sample is selected from: blood, whole blood, plasma, serum and fractions thereof. In some embodiments, the biological sample is selected from: PBMC (peripheral blood mononuclear cell), erythrocytes, leukocytes or thrombocytes. In some embodiments, the biological sample is bone marrow.

In some embodiments, the biological sample may be provided by removing a sample of cells from a subject (e.g., a biopsy). For a non-limiting example, a tissue sample can be removed from a tested subject by conventional biopsy techniques. In some embodiments, the biological sample is derived from a tumor. In some embodiments, the biological sample is selected from the group consisting of: tissue, cells, and cell-secreted vesicles. In some embodiments, said plurality of antigens (CTAs) are expressed within one or more cell-secreted vesicles. In some embodiments, the methods of the invention comprise detecting said plurality of antigens (CTAs) expressed within one or more cell-secreted vesicles (e.g., exosomes).

In some embodiments, the biological sample is cell-secreted vesicles. In some embodiments, the cell-secreted vesicles are microvesicles such as exosomes or ectosomes. Exosomes are known in the art as vesicles having a diameter of 30 to 100 nm that originate from cells. Ectosomes (also called shedding microvesicles (SMVs)) are known in the art as vesicles that are released directly from plasma membranes and have a diameter of 50 to 1000 nm. In some embodiments, the invention provides isolating a microvesicles-containing bodily fluid sample from the subject. In some embodiments, the methods further comprise the isolation of a selective exosome-containing fraction derived from cells of a specific type (e.g., cancer or tumor cells) or bodily fluid. Additionally, the selective exosome fraction may consist essentially of exosomes obtained from serum. Methods of isolating exosomes from a biological sample, including bodily fluids, are known in the art. For example, a method of differential centrifugation is described in a paper by Raposo et al. (Raposo et al., B lymphocytes secrete antigen-presenting vesicles. J Exp Med. 183:1161-721996).

In some embodiments, the expression profile is obtained by measuring protein levels of the plurality of antigens. In some embodiments, at least a portion of the plurality of antigens is expressed on a surface of a cell. In some embodiments, the plurality of antigens is expressed on a surface of a cell.

In some embodiments, the reference profile is an expression profile of the same set of CTAs which is obtained from one or more control biological samples. In some embodiments, the control biological sample originates from the same subject. In some embodiments, the control biological sample originates from the same source (e.g., tissue, blood, urine, etc.) as the biological sample obtained from the subject. In some embodiments, control biological samples are selected from the group consisting of: a sample from at least one healthy subject, a panel of samples from healthy subjects, and a stored set of data from healthy subjects. In some embodiments, the reference expression profile is obtained from a healthy subject. In some embodiments, a reference expression profile is obtained from a healthy subject of the same gender, and/or a similar age as the patient. In some embodiments, the reference expression profile is an average expression profile of a plurality of healthy subjects. In some embodiments, reference profiles are stored in a database, such as an internet database, a centralized or a decentralized database. In some embodiments, the stored reference profiles are derived from previous tests. In some embodiments, the reference profile is a mathematical function or an algorithm which has been developed on the basis of a plurality of reference profiles and allows a diagnosis.

In another embodiment, the control sample may be obtained from the same subject, such as an adjacent tissue (i.e., tissue adjacent to the tumor). In some embodiments, comparable samples may be obtained from the same individual at different times, such as for monitoring the efficacy of various therapies and/or preventive interventions.

As used herein, the terms "cancer" and "cancerous" refer to, or describe, the physiological condition in mammals that is typically characterized by unregulated cell growth and invasion. The terms cancer and cancerous encompasses: carcinoma, sarcoma, lymphoma, leukemia, melanoma, and blastoma. In one embodiment, carcinoma refers to tumors derived from epithelial cells including but not limited to breast cancer, prostate cancer, lung cancer, pancreas cancer, and colon cancer. As used herein, the term "sarcoma" refers of tumors derived from mesenchymal cells including but not limited to sarcoma botryoides, chondrosarcoma, Ewing's sarcoma, malignant hemangioendothelioma, malignant schwannoma, osteosarcoma and soft tissue sarcomas. As used herein, the term "lymphoma" refers to tumors derived from hematopoietic cells that leave the bone marrow and tend to mature in the lymph nodes. including but not limited to Hodgkin, non-Hodgkin lymphoma, and multiple myeloma. As used herein, the term "leukemia" refers to tumors derived from hematopoietic cells that leave the bone marrow and tend to mature in the blood, including but not limited to acute lymphoblastic leukemia, chronic lymphocytic leukemia, acute myelogenous leukemia, chronic myelogenous leukemia, hairy cell leukemia, T-cell prolymphocytic leukemia, large granular lymphocytic leukemia and adult T-cell leukemia. As used herein, the term "melanoma" refers to tumors derived from pigment cells (melanocytes), including but not limited to dermal melanoma and uveal melanoma. As used herein, the term "blastoma" refers to tumors derived from immature precursor cells or embryonic tissue, including but not limited to hepatoblastoma, medulloblastoma, nephroblastoma, neuroblastoma, pancreatoblastoma, pleuropulmonary blastoma, retinoblastoma and glioblastoma-multiforme.

Determining an Expression Profile

The term "expression profile" refers to expression of a group/set of genes. In some embodiments, the expression profile may be detected at the expression levels such as by analyzing and determining RNA values (e.g., mRNA or miRNA). The RNA levels may be determined in various samples including but not limited to cells, and exosomes. In some embodiments, the expression profile may be detected at the translation levels such as by analyzing and determining CTAs expressed on a cell surface such as by using antibodies.

As used in reference with the methods of the invention, "increase in expression of the expression profile" refers to a sum increase of expression of the specific set of CTAs. For a non-limiting example, a specific value of increase may be a result of increase of all the antigens of the set. Alternatively, specific value of increase may be a result of increase of only a few antigens of the set. In some embodiments, the increase refers to at least 10% increase, 20% increase, 30% increase, 40% increase, 50% increase, 60% increase, 70% increase, 80% increase, 90% increase, 100% increase in expression level of the expression profile.

A variety of known techniques may be suitable for determining an expression profile. Such techniques include methods based on hybridization analysis of polynucleotides and on sequencing of polynucleotides, and proteomics-based methods. In some embodiments, the determining step is performed by nucleic acid hybridization, nucleic acid amplification, or an immunological method. In some embodiments, the determining step is performed in-situ. In some embodiments, fluorescence labeling or staining are applied. In some embodiment, an imaging step is further applied.

In some embodiments, the expression profile is obtained by measuring protein levels of CT antigens. In some embodiments, the expression, and the level of expression, of proteins or polypeptides of interest can be detected through immunohistochemical staining of tissue slices or sections. Additionally, proteins/polypeptides of interest may be detected by Western blotting, ELISA or Radioimmunoassay (RIA) assays employing protein-specific antibodies.

Alternatively, protein levels can be determined by constructing an antibody microarray in which binding sites comprise immobilized, preferably monoclonal, antibodies specific to a plurality of proteins of interest. Methods for making monoclonal antibodies are well known (see, e.g., Harlow and Lane, 1988, ANTIBODIES: A LABORATORY MANUAL, Cold Spring Harbor, N.Y., which is incorporated in its entirety for all purposes). In one embodiment, monoclonal antibodies are raised against synthetic peptide fragments designed based on genomic sequence of the cell. With such an antibody array, proteins from the cell are contacted to the array, and their binding is assayed with assays known in the art.

In some embodiments, the determining step comprises the step of obtaining nucleic acid molecules from said non-testis biological sample. In some embodiments, the nucleic acids molecules are selected from mRNA molecules, DNA molecules and cDNA molecules. In some embodiments, the cDNA molecules are obtained by reverse transcribing the mRNA molecules. In some embodiments, the expression profile is determined by measuring mRNA levels of CT antigens. Methods for mRNA extraction are well known in the art and are disclosed in standard textbooks of molecular biology, including Ausubel et al., Current Protocols of Molecular Biology, John Wiley and Sons (1997). Methods for RNA extraction from paraffin embedded tissues are disclosed, for example, in Rupp and Locker, Lab Invest. 56:A67 (1987), and De Andres et al., BioTechniques 18:42044 (1995).

Numerous methods are known in the art for measuring expression levels of a one or more gene such as by amplification of nucleic acids (e.g., PCR, isothermal methods, rolling circle methods, etc.) or by quantitative in situ hybridization. Design of primers for amplification of specific genes is well known in the art, and such primers can be found or designed on various websites such as http://bioinfo.ut.ee/primer3-0.4.0/or https://pga.mgh.harvard.edu/primerbank/for example.

The skilled artisan will understand that these methods may be used alone or combined. Non-limiting exemplary method are described herein.

RT-qPCR: A common technology used for measuring RNA abundance is RT-qPCR where reverse transcription (RT) is followed by real-time quantitative PCR (qPCR). Reverse transcription first generates a DNA template from the RNA. This single-stranded template is called cDNA. The cDNA template is then amplified in the quantitative step, during which the fluorescence emitted by labeled hybridization probes or intercalating dyes changes as the DNA amplification process progresses. Quantitative PCR produces a measurement of an increase or decrease in copies of the original RNA and has been used to attempt to define changes of gene expression in cancer tissue as compared to comparable healthy tissues.

RNA-Seq: RNA-Seq uses recently developed deep-sequencing technologies. In general, a population of RNA (total or fractionated, such as poly(A)+) is converted to a library of cDNA fragments with adaptors attached to one or both ends. Each molecule, with or without amplification, is then sequenced in a high-throughput manner to obtain short sequences from one end (single-end sequencing) or both ends (pair-end sequencing). The reads are typically 30-400 bp, depending on the DNA-sequencing technology used. In principle, any high-throughput sequencing technology can be used for RNA-Seq. Following sequencing, the resulting reads are either aligned to a reference genome or reference transcripts, or assembled de novo without the genomic sequence to produce a genome-scale transcription map that consists of both the transcriptional structure and/or level of expression for each gene. To avoid artifacts and biases generated by reverse transcription direct RNA sequencing can also be applied.

Microarray: Expression levels of a gene may be assessed using the microarray technique. In this method, polynucleotide sequences of interest (including cDNAs and oligonucleotides) are arrayed on a substrate. The arrayed sequences are then contacted under conditions suitable for specific hybridization with detectably labeled cDNA generated from RNA of a test sample. As in the RT-PCR method, the source of RNA typically is total RNA isolated from a tumor sample, and optionally from normal tissue of the same patient as an internal control or cell lines. RNA can be extracted, for example, from frozen or archived paraffin-embedded and fixed (e.g., formalin-fixed) tissue samples. For archived, formalin-fixed tissue cDNA-mediated annealing, selection, extension, and ligation, DASL-Illumina method may be used. For a non-limiting example, PCR amplified cDNAs to be assayed are applied to a substrate in a dense array. Microarray analysis can be performed by commercially available equipment, following manufacturer's protocols, such as by using the Affymetrix GenChip technology, or Incyte's microarray technology.

As used herein, the terms "amplification" or "amplify" mean one or more methods known in the art for copying a target nucleic acid, e.g., the genes listed in any of the Tables disclosed herein, thereby increasing the number of copies of a selected nucleic acid sequence. Amplification may be exponential or linear. In a particular embodiment, the target nucleic acid is RNA.

As used herein, "nucleic acid" refers broadly to segments of a chromosome, segments or portions of DNA, cDNA, and/or RNA. Nucleic acid may be derived or obtained from an originally isolated nucleic acid sample from any source (e.g., isolated from, purified from, amplified from, cloned from, or reverse transcribed from sample DNA or RNA).

As used herein, the term "oligonucleotide" refers to a short polymer composed of deoxyribonucleotides, ribonucleotides or any combination thereof. Oligonucleotides are generally between about 10 and about 100 nucleotides in length. Oligonucleotides are typically 15 to 70 nucleotides long, with 20 to 26 nucleotides being the most common. An oligonucleotide may be used as a primer or as a probe. An oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, or at least 95% sequence identity.

As used herein, a "fragment" in the context of a nucleic acid refers to a sequence of nucleotide residues which hare at least about 5 nucleotides, at least about 7 nucleotides, at least about 9 nucleotides, at least about 11 nucleotides, or at least about 17, nucleotides. A fragment is typically less than about 300 nucleotides, less than about 100 nucleotides, less than about 75 nucleotides less than about 50 nucleotides, or less than about 30 nucleotides. In certain embodiments, the fragments can be used in polymerase chain reaction (PCR), or various hybridization procedures to identify or amplify identical or related DNA molecules.

As used herein, a "primer" for amplification is an oligonucleotide that specifically anneals to a target or marker nucleotide sequence. The 3' nucleotide of the primer should be identical to the target or marker sequence at a corresponding nucleotide position for optimal primer extension by a polymerase. As used herein, a "forward primer" is a primer that anneals to the anti-sense strand of double stranded DNA (dsDNA). A "reverse primer" anneals to the sense-strand of dsDNA.

As used herein, "target nucleic acid" refers to segments of a chromosome, a complete gene with or without intergenic sequence, segments or portions a gene with or without intergenic sequence, or sequence of nucleic acids to which probes or primers are designed. Target nucleic acids may be derived from genomic DNA, cDNA, or RNA. As used herein, target nucleic acid may be native DNA or a PCR-amplified product.

The expression data used in the methods disclosed herein may be normalized. The term "normalized" with regard to a gene transcript or a gene expression product refers to the level of the transcript or gene expression product relative to the mean levels of transcripts/products of a set of reference genes, wherein the reference genes are either selected based on their minimal variation across, patients, tissues or treatments ("housekeeping genes"), or the reference genes are the totality of tested genes.

In general, samples may be normalized by a common factor. For example, cell-containing samples are normalized by protein content or cell count. In some embodiments, samples (i.e., the expression levels) are normalized using a set of normalization genes. In another embodiment, said expression levels are normalized expression levels. With respect to RT-PCR experiments involving archived fixed paraffin embedded tissue samples, sources of systematic variation are known to include the degree of RNA degradation relative to the age of the patient sample and the type of fixative used to store the sample. Other sources of systematic variation are attributable to laboratory processing conditions. More recent tumor banking involves frozen samples of tumor and normal tissue. Normalization is also useful to correct for systematic variation.

Assays may provide normalization by incorporating the expression of certain normalizing genes, which do not differ significantly in expression levels under the relevant conditions. Exemplary normalization genes include housekeeping genes. Alternatively, or additionally, array datasets can be normalized using known RMA, MAS 5.0, Z scoring and by reference to their average values.

Determining Proliferation State of a Cell

In one embodiment, the invention provides a CTA signature indicative of a proliferation state of a cell. In one embodiment, said CTA signature is indicative of cancer. In another embodiment, the CTA signature is indicative of a pluripotency state of a cell.

According to one aspect, the invention provides a method for determining a proliferation state of a cell (e.g., detecting cancer) in a subject, the method comprises the steps of: (a) determining an expression profile of a plurality of CTAs comprising: CEP55, GAGE8/GAGE12F, ZNF165, PRAME, SPAG4, PAGE4, PBK, SPANXA2/SPANXB1/SPANXC/SPANXA1, TSPY8/TSPY4/TSPY3/TSPY1, and GAGE12D/GAGE12F, in a non-testis biological sample obtained from a subject; and (b) comparing the expression profile to a reference expression profile. In some embodiments, an increase in expression of the expression profile compared to the reference expression profile is indicative for cancer. In some embodiments, the method is for distinguishing a cancer afflicted subject from non-cancer afflicted subject.

In some embodiments, the plurality of antigens useful for detecting cancer in a subject or determining a proliferation state of a cell is selected from at least one antigen selected from CEP55, OIP5, TTK, CASC5, and PBK; and a least one additional antigen selected from GAGE8/12F, ZNF165, PRAME, SPAG4, PAGE4, SPANXA2/B1/C/A1, TSPY8/4/3/1, and GAGE12D/F. In some embodiments, the plurality of antigens useful for detecting cancer in a subject or determining a proliferation state of a cell is selected from (i) at least one antigen selected from CEP55, OIP5, TTK, CASC5, and PBK; (ii) at least one GAGE antigen (e.g., cluster 1.2), and (iii) at least one additional antigen selected from ZNF165, PRAME, SPAG4, PAGE4, SPANXA2/B1/C/A1, TSPY8/4/3/1. In some embodiments, the plurality of antigens useful for detecting cancer in a subject or determining a proliferation state of a cell is selected from (i) at least one antigen selected from CEP55, OIP5, TTK, CASC5, and PBK; (ii) at least one GAGE antigen (e.g., cluster 1.2), and (iii) a plurality of antigens selected from ZNF165, PRAME, SPAG4, PAGE4, SPANXA2/B1/C/A1, TSPY8/4/3/1.

In some embodiments, the plurality of antigens is at least 4, 5, 6, 7, 8, 9, 10, 11, 12, 13, 14, 15, 16, 17, 18, 19, 20, 21, 22, 23, 24, 25, 26, 27, 28, 29, 30, or 31 antigens. Each possibility represents a separate embodiment of the present invention. In some embodiments, high diagnosis accuracy for distinguishing cancer-afflicted subjects from non-cancer afflicted subjects is achieved using at least 10 antigens selected from CEP55, GAGE8/GAGE12F, ZNF165, PRAME, SPAG4, PAGE4, PBK, SPANXA2/SPANXB1/SPANXC/SPANXA1, TSPY8/TSPY4/TSPY3/TSPY1, and GAGE12D/GAGE12F. In some embodiments, the plurality of CTAs comprises or consists of: CEP55, GAGE8/GAGE12F, ZNF165, PRAME, SPAG4, PAGE4, PBK, SPANXA2/SPANXB1/SPANXC/SPANXA1, TSPY8/TSPY4/TSPY3/TSPY1, and GAGE12D/GAGE12F.

In some embodiments, the method according to the invention distinguishes a cancer-afflicted subject from a non-cancer afflicted subject with a sensitivity of at least 80%, 85%, 86%, 87%, 88%, 89%, 90%, 95%, 96%, 97%, 98%, 99% or 100%. The specificity of the method for distinguishing a cancer-afflicted subject from a non-cancer afflicted subject may be at least 80%, 85%, 86%, 87%, 88%, 89%, 90%, 91%, 92%, 93%, 94%, 95%, 96%, 97%, 98%. 99% or greater. In some embodiments, the method according to the invention distinguishes a cancer-afflicted subject from a non-cancer afflicted subject with an accuracy of at least 90%, 91%, 92%, 93%, 94%, 95%, 96%, 97%, 98%, 99% or 100%. Each possibility represents a separate embodiment of the present invention.

Diagnosis, Staging, Prognosis and Monitoring Cancer

According to another aspect, the invention provides a method for diagnosis, prognosis and/or staging a specific type of cancer in a subject, the method comprises the steps of: (a) determining an expression profile of a predetermined set of CTAs, in a non-testis biological sample obtained from a subject; and (b) comparing the expression profile to a reference expression profile, wherein an increase in expression of the expression profile compared to the reference expression profile is indicative for a specific cancerous state, thereby providing a diagnosis, prognosis, and or staging a specific type of cancer in said subject.

The term "diagnosis" (along with grammatical variations thereof such as "diagnosing" or "diagnostic") refers to the identification of a molecular or pathological state, disease or condition, such as the identification of cancer, or refers to the identification of a cancer patient who may benefit from a particular treatment regimen.

The term "prediction" or "predicting" is used herein to refer to the likelihood that a patient will respond either favorably or unfavorably to a particular anti-cancer therapy. In one embodiment, prediction or predicting relates to the extent of those responses. In one embodiment, the prediction or predicting relates to whether and/or the probability that a patient will survive or improve following treatment, for example treatment with a particular therapeutic agent, and for a certain period of time without disease progression.

The term "benefit" is used in the broadest sense and refers to any desirable effect and specifically includes clinical benefit as defined herein.

The term "stage" in the context of a disease (such as cancer or tumor), refers to the progression status of the disease which is indicative of the severity of the disease. The term "staging" as used herein refers to identifying the particular stage at which the disease has progressed.

The term "prognosis" as used herein, refers to describing the likelihood of the outcome or course of a specific type of cancer.

(i) Breast Cancer:

In some embodiments, increased expression of a plurality of CTAs comprises: RBM46, CT47A1/A2/A3/A4/A5/A6/A8/A9/A10/A7/A11, PBK, and DDX53, compared to the reference expression profile is indicative of breast cancer.

In some embodiments, the CTA breast cancer signature further comprises one or more CTAs selected from the group consisting of: MAGEB3, LOC653786/OTOA, DMRT1, LDHC, CCDC83, ANKRD45, DDX53, BAGE, TDRD1, CEP55, PRM1, SSX2B/SSX2, SEMG1, TPTE and SPAG1. In some embodiments, the plurality of CTAs comprises or consists of: RBM46, CT47A1/A2/A3/A4/A5/A6/A8/A9/A10/A7/A11, PBK, and DDX53. In some embodiments, the plurality of CTAs is selected from the group consisting of: RBM46, CT47A1/A2/A3/A4/A5/A6/A8/A9/A10/A7/A11, PBK, DDX53, MAGEB3, LOC653786/OTOA, DMRT1, LDHC, CCDC83, ANKRD45, DDX53, BAGE, TDRD1, CEP55, PRM1, SSX2B/SSX2, SEMG1, TPTE and SPAG1. In some embodiments, the plurality of CTAs comprises RBM46 and at least one antigen selected from CT47A1/A2/A3/A4/A5/A6/A8/A9/A10/A7/A11, PBK, and DDX53. In some embodiments, the plurality of CTAs comprises RBM46, CT47A1/A2/A3/A4/A5/A6/A8/A9/A10/A7/A11, and at least one antigen selected from PBK, and DDX53.

In some embodiments, the breast cancer predetermined set of CTAs comprises at most 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. In some embodiments, the predetermined set of CTAs comprises at least 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. Each possibility represents a separate embodiment of the present invention.

(ii) Ovarian Cancer:

In some embodiments, increased expression of a set of CTAs comprising: ZNF165, PRAME, GAGE1 and GAGE12F/G/I/7/5, compared to the reference expression profile is indicative of ovarian cancer and severity thereof. In some embodiments, severity comprises the stage of the ovarian cancer.

In some embodiments, the plurality of CTAs further comprises one or more CTA antigen selected from the group consisting of: SPAG1, TTK, LEMD1, SPA17, PBK, TMEFF1, CEP55, CTNNA2, SPAG4, CTCFL, SPAG17, BAGE, ATAD2, PRSS54, GPAT2, CCDC83, MAGEA11, CT45A2/A1/A6/A5/A4/A3, LY6K, TSGA10, DSCR8, CTAG1A/1B, and SAGE1. In some embodiments, the set/plurality of CTAs comprises or consists of: ZNF165, PRAME, GAGE1 and GAGE12F/G/I/7/5.

In some embodiments, the set/plurality of CTAs comprises or consists of: ZNF165, PRAME, GAGE1 and GAGE12F/G/I/7/5 and one or more CTA antigen selected from the group consisting of: SPAG1, TTK, LEMD1, SPA17, PBK, TMEFF1, CEP55, CTNNA2, SPAG4, CTCFL, SPAG17, BAGE, ATAD2, PRSS54, GPAT2, CCDC83, MAGEA11, CT45A2/CT45A1/CT45A6/CT45A5/CT45A4/CT45A3, LY6K, TSGA10, DSCR8, CTAG1A/CTAG1B and SAGE1. In some embodiments, the set/plurality of CTAs is selected from the group consisting of: SPAG1, TTK, LEMD1, SPA17, PBK, TMEFF1, CEP55, CTNNA2, SPAG4, CTCFL, SPAG17, BAGE, ATAD2, PRSS54, GPAT2, CCDC83, MAGEA11, CT45A2/CT45A1/CT45A6/CT45A5/CT45A4/CT45A3, LY6K, TSGA10, DSCR8, CTAG1A/CTAG1B, SAGE1, ZNF165, PRAME, GAGE1 and GAGE12F/GAGE12G/GAGE12I/GAGE7/GAGE5.

In some embodiments, the predetermined set of CTAs comprises at most 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. In some embodiments, the predetermined set of CTAs comprises at least 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. Each possibility represents a separate embodiment of the present invention.

(iii) Adrenal Cancer:

In some embodiments, increased expression of a set of CTAs comprising: PBK, MAGEA12, SPAG4 and ELOVL4, compared to the reference expression profile is indicative of adrenal cancer and severity thereof. In some embodiments, severity comprises the stage of the adrenal cancer. In some embodiments, the plurality/set of CTAs further comprises one or more CTA antigen selected from the group consisting of: CEP55, TTK, ATAD2, OIP5, FAM133A, FATE1, IL13RA2, PRAME, MAGEA6, CTNNA2, MAGEA3, and PLAC1. In some embodiments, the set/plurality of CTAs comprises or consists of: PBK, MAGEA12, SPAG4 and ELOVL4. In some embodiments, the set/plurality of CTAs consists of: PBK, MAGEA12, SPAG4 and ELOVL4 and one or more CTA antigen selected from the group consisting of: CEP55, TTK, ATAD2, OIP5, FAM133A, FATE1, IL13RA2, PRAME, MAGEA6, CTNNA2, MAGEA3, and PLAC1. In some embodiments, the set/plurality of CTAs is selected from the group consisting of: CEP55, TTK, ATAD2, OIP5, FAM133A, FATE1, IL13RA2, PRAME, MAGEA6, CTNNA2, MAGEA3, PLAC1, PBK, MAGEA12, SPAG4 and ELOVL4.

In some embodiments, the set/plurality of CTAs comprises at least one antigen selected from: PBK, ATAD2 and CEP55; and at least one antigen selected from MAGEA12, SPAG4 and ELOVL4. In some embodiments, the set/plurality of CTAs comprises (i) at least one antigen selected from: PBK, ATAD2 and CEP55; (ii) at least one MAGEA antigen (e.g., cluster 5.5); and (iii) at least one antigen selected from SPAG4 and ELOVL4.

In some embodiments, the predetermined set of CTAs comprises at most 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. In some embodiments, the predetermined set of CTAs comprises at least 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. Each possibility represents a separate embodiment of the present invention.

(iv) Liver Cancer:

In some embodiments, increased expression of a set of CTAs comprising: SLCO6A1 and CEP55, compared to the reference expression profile is indicative of liver cancer and severity thereof. In some embodiments, increase expression of a set of CTAs comprising: MAGEB4, TTK, and SLCO6A1, compared to the reference expression profile is indicative of liver cancer and severity thereof. As exemplified herein, TTK, CEP55 and OIP5 (e.g., cluster 2.5) are correlative and interchangeable in liver cancer diagnosis (Table 5). In one embodiment, the plurality/set of CTAs further comprises one or more CTA antigen selected from the group consisting of: PBK, SPA17, ATAD2, FAM133A, TTK, MAGEA1, OIP5, CABYR, SSX1, MAGEA3, SSX2B/2, MAGEA6, MAGEA12, CTNNA2, TPTE, SSX4B/4, XAGE1B/1E, MAGEC1, GAGE8/12F/2A/2D/12J/12G/2B/2E/12I/7/6/5/4/3/2C/1, GAGE12D/12F/2A/12H/12E/12C/12G/12I/7/6/5/4/2C, and GAGE12F/12G/12I/7/5.

In some embodiments, the set/plurality of CTAs comprises or consists of: SLCO6A1 and CEP55. In some embodiments, the set/plurality of CTAs comprises: SLCO6A1 and at least one antigen selected from CEP55, OIP5 and TTK (e.g., cluster 2.2). In some embodiments, the set/plurality of CTAs comprises: at least one antigen selected from MAGEB4, and SLCO6A1 and at least one antigen selected from CEP55, OIP5 and TTK (e.g., cluster 2.2). In some embodiments, the set/plurality of CTAs consists of: SLCO6A1, at least one antigen selected from CEP55, OIP5 and TTK (e.g., cluster 2.2) and one or more CTA antigen selected from the group consisting of: PBK, SPA17, ATAD2, FAM133A, MAGEA1, CABYR, SSX1, MAGEA3, SSX2B/SSX2, MAGEA6, MAGEA12, CTNNA2, TPTE, SSX4B/SSX4, XAGE1B/XAGE1E, MAGEC1, GAGE8/12F/2A/2D/12J/12G/2B/2E/12I/7/6/5/4/3/2C/1, GAGE12D/12F/2A/12H/12E/12C/12G/12I/7/6/5/4/2C, and GAGE12F/12G/12I/7/5. In some embodiments, the plurality of CTAs is selected from the group consisting of: PBK, SPA17, ATAD2, FAM133A, TTK, MAGEA1, OIP5, CABYR, SSX1, MAGEA3, SSX2B/2, MAGEA6, MAGEA12, CTNNA2, TPTE, SSX4B/SSX4, XAGE1B/1E, MAGEC1, GAGE8/12F/2A/2D/12J/12G/2B/2E/12I/7/6/5/4/3/2C/1, GAGE12D/12F/2A/12H/12E/12C/12G/12I/7/6/5/4/2C, and GAGE12F/12G/12I/7/5.

In some embodiments, the predetermined set of CTAs comprises at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. In some embodiments, the predetermined set of CTAs comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. Each possibility represents a separate embodiment of the present invention.

(v) Multiple Myeloma:

In some embodiments, increased expression of a set of CTAs comprising: FAM133A, MORC1, TEX14, ANKRD45, MAGEB2, MAGEC1 and ELOVL4, compared to the reference expression profile is indicative of multiple myeloma and severity thereof. In some embodiments, severity comprises distinguishing between smoldering multiple myeloma and multiple myeloma. In some embodiments, the set/plurality of CTAs comprises or consists of: FAM133A, MORC1, TEX14, ANKRD45, MAGEB2, MAGEC1 and ELOVL4.

In some embodiments, the set of CTAs is selected from the group consisting of: FAM133A, MORC1, TEX14, ANKRD45, MAGEB2, MAGEC1 and ELOVL4. In some embodiments, the set/plurality of CTAs comprises FAM133A, and at least one antigen selected from MORC1, TEX14, ANKRD45, MAGEB2, MAGEC1 and ELOVL4. In some embodiments, the set/plurality of CTAs comprises FAM133A, MORC1 and at least one antigen selected from TEX14, ANKRD45, MAGEB2, MAGEC1 and ELOVL4. In some embodiments, the set/plurality of CTAs comprises FAM133A, MORC1, TEX14 and at least one antigen selected from ANKRD45, MAGEB2, MAGEC1 and ELOVL4. In some embodiments, the set/plurality of CTAs comprises FAM133A, MORC1, TEX14, ANKRD45 and at least one antigen selected from MAGEB2, MAGEC1 and ELOVL4. In some embodiments, the set/plurality of CTAs comprises FAM133A, MORC1, TEX14, ANKRD45, MAGEB2 and at least one antigen selected from MAGEC1 and ELOVL4.

In some embodiments, the predetermined set of CTAs comprises at most 3, 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. In some embodiments, the predetermined set of CTAs comprises at least 3, 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. Each possibility represents a separate embodiment of the present invention.

(vi) Glioblastoma:

In some embodiments, increased expression of a set of CTAs comprising: IL13RA2, ZNF165, CEP55, CTAG2, SPAG4, MORC1 and SPAG8, compared to the reference expression profile is indicative of glioblastoma and severity thereof. In some embodiments, severity comprises the stage of the glioblastoma. In some embodiments, severity comprises distinguishing between glioblastoma with necrosis and without. In some embodiments, the set/plurality of CTAs comprises or consists of: IL13RA2, ZNF165, CEP55, CTAG2, SPAG4, MORC1 and SPAG8.

In some embodiments, the set/plurality of CTAs comprises: IL13RA2 and at least one antigen selected from ZNF165, CEP55, CTAG2, SPAG4, MORC1 and SPAG8. In some embodiments, the set/plurality of CTAs comprises: IL13RA2, ZNF16, and at least one antigen selected from CEP55, CTAG2, SPAG4, MORC1 and SPAG8. In some embodiments, the set/plurality of CTAs comprises: IL13RA2, ZNF16, CEP55 and at least one antigen selected from CTAG2, SPAG4, MORC1 and SPAG8. In some embodiments, the set/plurality of CTAs comprises: IL13RA2, ZNF16, CEP55, CTAG2 and at least one antigen selected from SPAG4, MORC1 and SPAG8. In some embodiments, the set/plurality of CTAs comprises: IL13RA2, ZNF16, CEP55, CTAG2, SPAG4 and at least one antigen selected from MORC1 and SPAG8.

In some embodiments, the predetermined set of CTAs comprises at most 7, 8, 9, 10, 11, 12, 13, 14, 15, 16, 17, 18, 19, 20, 21, 22, 23, 24, 25, 26, 27, 28, 29, 30, 40 or 50 antigens. In some embodiments, the predetermined set of CTAs comprises at least 4, 5, 6, 7, 8, 9, 10, 11, 12, 13, 14, 15, 16, 17, 18, 19, 20, 21, 22, 23, 24, 25, 26, 27, 28, 29, 30, or 40 antigens.

(vii) Colon Cancer:

In some embodiments, increased expression of a set of CTAs comprising: MAGEA11, ODF2, IL13RA2, MAGEA6, DDX43, CEP55, MAGEA1, MAGEB3, SPANXB1, BAGE and TSGA10, compared to the reference expression profile is indicative of colon cancer and severity thereof. In some embodiments, severity comprises the ability to metastasize. In some embodiments, the set/plurality of CTAs further comprises one or more CTAs selected from the group consisting of: MAGEA3, MAGEA12, MAGEA1, and IL13RA2. In some embodiments, the set/plurality of CTAs consists of: MAGEA11, ODF2, IL13RA2, MAGEA6, DDX43, CEP55, MAGEA1, MAGEB3, SPANXB1, BAGE and TSGA10. In some embodiments, the set/plurality of CTAs is selected from the group consisting of: MAGEA11, ODF2, IL13RA2, MAGEA6, DDX43, CEP55, MAGEA1, MAGEB3, SPANXB1, BAGE, TSGA10, MAGEA3, MAGEA12, MAGEA1, and IL13RA2.

In some embodiments, the set/plurality of CTAs is selected from the group consisting of: MAGEA11, and at least one antigen selected from ODF2, IL13RA2, MAGEA6, DDX43, CEP55, MAGEA1, MAGEB3, SPANXB1, BAGE and TSGA10. In some embodiments, the set/plurality of CTAs is selected from the group consisting of: MAGEA11, ODF2, and at least one antigen selected from IL13RA2, MAGEA6, DDX43, CEP55, MAGEA1, MAGEB3, SPANXB1, BAGE and TSGA10. In some embodiments, the set/plurality of CTAs is selected from the group consisting of: MAGEA11, ODF2, IL13RA2, and at least one antigen selected from MAGEA6, DDX43, CEP55, MAGEA1, MAGEB3, SPANXB1, BAGE and TSGA10. In some embodiments, the set/plurality of CTAs is selected from the group consisting of: MAGEA11, ODF2, IL13RA2, and at least one antigen selected from MAGEA6, DDX43, CEP55, MAGEA1, MAGEB3, SPANXB1, BAGE and TSGA10. In some embodiments, the set/plurality of CTAs is selected from the group consisting of: MAGEA11, ODF2, IL13RA2, at least one antigen selected from MAGEA6, MAGEA3, MAGEA12 (cluster 6.1-3), and at least one antigen selected from DDX43, CEP55, MAGEA1, MAGEB3, SPANXB1, BAGE and TSGA10.

In some embodiments, increased expression of the above described sets of CTAs as compared to the reference expression profile is indicative of colon cancer cells that have metastasized to the lung or liver. In some embodiments, increased expression of the above described set of CTAs can distinguish metastatic colon cancer cells from neighboring healthy liver or lung cells.

In some embodiments, the predetermined set of CTAs comprises at most 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. In some embodiments, the predetermined set of CTAs comprises at least 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. Each possibility represents a separate embodiment of the present invention.

(viii) Lung Cancer:

In some embodiments, increased expression of a set of CTAs comprising: PBK, MORC1, XAGE1B/1E, BAGE2/3/5/KMT2C and IL13RA2, compared to the reference expression profile is indicative of lung cancer and severity thereof. In some embodiments, the set/plurality of CTAs further comprises one or more CTAs selected from the group consisting of: TTK, ATAD2, CEP55, LDHC, PRAME, HORMAD1, PASD1, MAGEA6, MAGEA2B/MAGEA2, ELOVL4, SPAG4 and MAGEA3. In some embodiments, the set/plurality of CTAs comprises or consists of: PBK, MORC1, XAGE1B/1E, BAGE2/3/5/KMT2C and IL13RA2. In some embodiments, the plurality/set of CTAs is selected from the group consisting of: TTK, ATAD2, CEP55, LDHC, PRAME, HORMAD1, PASD1, MAGEA6, MAGEA2BA2, ELOVL4, SPAG4, MAGEA3, PBK, MORC1, XAGE1B/1E, BAGE2/3/5/KMT2C and IL13RA2.

In some embodiments, the plurality/set of CTAs comprises the CTA selected from the group consisting of: TTK and PRAME. In some embodiments, the set/plurality of CTAs comprises: PBK and at least one antigen selected from MORC1, XAGE1B/XAGE1E, BAGE2/BAGE3/BAGE5/KMT2C and IL13RA2. In some embodiments, the set/plurality of CTAs comprises: PBK, MORC1, and at least one antigen selected from XAGE1B/1E, BAGE2/3/5/KMT2C and IL13RA2. In some embodiments, the set/plurality of CTAs comprises: PBK, MORC1, XAGE1B/1E, and at least one antigen selected from BAGE2/3/5/KMT2C and IL13RA2.

In some embodiments, the predetermined set of CTAs comprises at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. In some embodiments, the predetermined set of CTAs comprises at least 2,3, 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. Each possibility represents a separate embodiment of the present invention.

(ix) Prostate Cancer:

In some embodiments, increased expression of a set of CTAs comprising: TDRD1, POTED, DCAF12 and TSGA10, compared to the reference expression profile is indicative of prostate cancer and severity thereof. In some embodiments, the predetermined set of CTAs comprises TDRD1, and at least one antigen selected from POTED, DCAF12 and TSGA10.

In some embodiments, the predetermined set of CTAs comprises TDRD1, POTED, and at least one antigen selected from DCAF12 and TSGA10.

In some embodiments, the predetermined set of CTAs comprises at most 4, 5, 6, 7, 8, 9, 10, 11, 12, 13, 14, 15, 16, 17, 18, 19, 20, 21, 22, 23, 24, 25, 26, 27, 28, 29, 30, or 40 antigens. In some embodiments, the predetermined set of CTAs comprises at least 4, 5, 6, 7, 8, 9, 10, 11, 12, 13, 14, 15, 16, 17, 18, 19, 20, 21, 22, 23, 24, 25, 26, 27, 28, 29, 30, or 40 antigens.

(x) Melanoma:

In some embodiments, increased expression of a set of CTAs comprising: PRAME and CTNNA2, compared to the reference expression profile is indicative of melanoma cancer and severity thereof. In some embodiments, the set/plurality of CTAs further comprises one or more CTAs selected from the group consisting of: MAGEA2B/2, TMEFF1, IGSF11, MAGEA3, SSX1, MAGEA6, MAGEA12, PBK, ANKRD45, SSX4B/SSX4, MAGEC1, SSX2B/SSX2, MAGEA1, MAGEC2, DSCR8, TTK, CTAG1A/CTAG1B, TPTE, XAGE1B/XAGE1E and IL13RA2. In some embodiments, the set/plurality of CTAs comprises or consists of: PRAME and CTNNA2. In some embodiments, the plurality/set of CTAs is selected from the group consisting of: PRAME, CTNNA2, MAGEA2B/MAGEA2, TMEFF1, IGSF11, MAGEA3, SSX1, MAGEA6, MAGEA12, PBK, ANKRD45, SSX4B/SSX4, MAGEC1, SSX2B/SSX2, MAGEA1, MAGEC2, DSCR8, TTK, CTAG1A/CTAG1B, TPTE, XAGE1B/XAGE1E and IL13RA2.

In some embodiments, the predetermined set of CTAs comprises at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. In some embodiments, the predetermined set of CTAs comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. Each possibility represents a separate embodiment of the present invention.

(xi) Uveal Melanoma

In some embodiments, increased expression of a set of CTAs comprising: DDX43, SSX1, ATAD2 and CEP55 compared to the reference expression profile is indicative of uveal melanoma. In some embodiments, the set/plurality of CTAs comprises or consists of: DDX43, SSX1, ATAD2 and CEP55. In some embodiments, the set/plurality of CTAs comprises DDX43, and at least one antigen selected from SSX1, ATAD2 and CEP55. In some embodiments, the set/plurality of CTAs comprises DDX43, and SSX1, and at least one antigen selected from ATAD2 and CEP55.

(xii) Kidney Cancer:

In some embodiments, increased expression of a set of CTAs comprising: CEP55, GAGE8/12F, SPAG4, LOC653786/OTOA and CTNNA2, compared to the reference expression profile is indicative of kidney cancer and severity thereof. In some embodiments, the set/plurality of CTAs further comprises one or more CTAs selected from the group consisting of: TPTE, ATAD2, GAGE8/12F/2A/2D/12J/12G/2B/2E/12I/7/6/5/4/3/2C/1, MAGEA6, MORC1, TTK, PBK, RGS22, TMEFF1, ARX, MAGEB4, PRAME, GAGE12D/2F/2A/12H/12E/12C/12G/12I/7/6/5/4/2C, TEX14, POTED, DMRT1, CTCFL, GPAT2, GAGE12F/12G/2I/E7/E5, GAGE3, SPANXA2/C/A1, DDX43, and GAGE1. In some embodiments, the set/plurality of CTAs consists of: CEP55, GAGE8/GAGE12F, SPAG4, LOC653786/OTOA and CTNNA2. In some embodiments, the plurality/set of CTAs is selected from the group consisting of: CEP55, GAGE8/12F/2A/2D/12J/12G/2B/2E/12I/7/6/5/4/3/2C/1, MAGEA6, MORC1, TTK, PBK, RGS22, TMEFF1, ARX, MAGEB4, PRAME, GAGE12D/2F/2A/12H/12E/12C/12G/12I/7/6/5/4/2C, TEX14, POTED, DMRT1, CTCFL, GPAT2, GAGE12F/12G/2I/E7/E5, GAGE3, SPANXA2/C/A1, DDX43, and GAGE1.

In some embodiments, the set/plurality of CTAs comprises at least one antigen selected from CEP55, TTK and ATAD2, and at least one antigen selected from GAGE8/12F, SPAG4, LOC653786/OTOA and CTNNA2. In some embodiments, the set/plurality of CTAs comprises (i) at least one antigen selected from CEP55, TTK and ATAD2, (ii) at least one antigen selected from GAGE8/12F, (iii) at least one antigen selected from GAGE8/12F, SPAG4, LOC653786/OTOA and CTNNA2. In some embodiments, the set/plurality of CTAs comprises (i) at least one antigen selected from CEP55, TTK and ATAD2, (ii) GAGE8/12F and SPAG4 (iii) at least one antigen selected from, LOC653786/OTOA and CTNNA2.

In some embodiments, the predetermined set of CTAs comprises at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. In some embodiments, the predetermined set of CTAs comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. Each possibility represents a separate embodiment of the present invention.

(xiii) Oral Squamous Cell Carcinoma:

In some embodiments, increased expression of a set of CTAs comprising: LY6K, and MAGEA6, compared to the reference expression profile is indicative of oral squamous cell carcinoma and severity thereof. In some embodiments, increased expression of a set of CTAs comprising: LY6K, and MAGEA6, compared to the reference expression profile is indicative of metastasis to the lymph. In some embodiments, the set/plurality of CTAs further comprises one or more CTAs selected from the group consisting of PLAC1, LEMD1, MAGEA1, MAGEA11, MAGEA4, MAGEA12, and CEP55. In some embodiments, the set/plurality of CTAs comprises or consists of: LY6K, and MAGEA6. In some embodiments, the plurality/set of CTAs is selected from the group consisting of: LY6K, MAGEA6, PLAC1, LEMD1, MAGEA1, MAGEA11, MAGEA4, MAGEA12, and CEP55.

In some embodiments, the predetermined set of CTAs comprises at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. In some embodiments, the predetermined set of CTAs comprises at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 40 or 50 antigens. Each possibility represents a separate embodiment of the present invention.

In some embodiments, the diagnosis described herein is useful for determining a stage and/or severity of a cancer. In some embodiments, the invention provides a method for staging a specific type of cancer in a subject, the method comprises the steps of: (a) determining an expression profile of a set of CTAs relevant to the cancer type, as described herein, in a non-testis biological sample obtained from a subject; and (b) comparing the expression profile to a reference expression profile, wherein an amount of increased expression of the expression profile compared to the reference expression profile correlates to a stage of the cancer, thereby providing a prediction of cancer outcome. In some embodiments, the stage is determined by comparing the expression profile to a statistical analysis of expression profiles of subjects having known stages of the specific type of cancer.

In some embodiments, specific sets of CTAs may be used to determine stage/severity of the cancer. In some embodiments, the set of CTAs for detecting cancer may differ at least in part from the set of CTAs for determining stage/severity of the same cancer. As exemplified in the example section below, the CTAs: ZNF165, PRAME, GAGE1 and GAGE12F/GAGE12G/GAGE12I/GAGE7/GAGE5 were found to distinguish ovarian cancer samples from non-cancerous samples and the CTAs: DDX43, KIAA0100 and MAGEA4 were found to have high accuracy for distinguishing between different stages of ovarian cancer.

In some embodiments, the method and/or kit of the invention are based on determination of a plurality of antigens comprising CEP55, TTK and SPAG4 for determining breast cancer.

In some embodiments, the method and/or kit of the invention are based on determination of a plurality of antigens comprising CEP55, ATAD2, MAGEA3, MAGEA4, and SPANXB2 for determining liver cancer.

In some embodiments, the method and/or kit of the invention are based on determination of a plurality of antigens comprising MAGEA6, ODF2, and BRDT for determining esophagus cancer;

In some embodiments, the method and/or kit of the invention are based on determination of a plurality of antigens comprising CEP55, MAGEA6, and MAGEA11 for determining colon cancer;

In some embodiments, the method and/or kit of the invention are based on determination of a plurality of antigens comprising CEP55, MAGEA2B, MAGEA9B, MAGEAB3, MAGEAB2, MAGEA1, SPANXB1, and SEMG1 for determining thyroid cancer.

In some embodiments, an increase in expression of a plurality of CTAs selected from the group consisting of: CEP55, PBK, TTK, ATAD2 and OIP5, compared to a reference profile is indicative of cancer stem cells. In some embodiments, the method and/or kit of the invention are based on determination of a plurality of antigens selected from the group consisting of: CEP55, PBK, TTK, ATAD2, and OIP5 for determining cancer stem cell. In some embodiments, the method and/or kit of the invention are based on determination of a plurality of antigens comprising: CEP55, PBK, TTK, ATAD2, and OIP5 for determining cancer stem cell.

In some embodiments, the diagnosis described herein is useful for predicting the response of the subject to therapeutic intervention. In some embodiments, the invention provides a method for monitoring a response to anti-cancer therapy. In some embodiments, anti-cancer therapy is a radiotherapy, a chemotherapy any other treatment with an anti-cancer agent, or a combination thereof. In embodiments of the method for monitoring a response to anti-cancer therapy, the biological sample is obtained from the subject in at least two-time points. In embodiments of the method for monitoring a response to anti-cancer therapy, the biological sample is obtained from the subject in several time points. In some embodiments, the biological sample is obtained from the subject prior to initiation of the anti-cancer therapy. In some embodiments, the biological sample is obtained from the subject following initiation of anti-cancer therapy. In some embodiments, the biological sample is obtained from the subject post anti-cancer therapy. In some embodiments, decrease in expression profile correlates to a good response of the subject to the treatment.

The methods and kits of the invention may also be used for cancer prognosis. According to some embodiments, the invention provides a method for cancer prognosis in a subject, the method comprises the steps of: (a) determining an expression profile of a set of CTAs relevant to the cancer type, as described herein, in a non-testis biological sample obtained from a subject; and (b) comparing the expression profile to a reference expression profile, wherein an increased level of expression of the expression profile compared to the reference expression profile, above a predefined threshold correlates with poor outcome, thereby providing a prediction of cancer outcome.

In some embodiments, increased level above a predefined threshold is indicative for poor prognosis. In some embodiments, the predefined threshold is obtained by a statistical analysis of expression profiles of subjects having known prognosis and/or stages of the specific type of cancer. In some embodiments, increase in the CTA genes which are indicative for a specific cancer is correlative to a severity/stage of the cancer.

Kits

According to one aspect the invention provides a kit for detecting a cancerous state in a subject. According to one aspect the invention provides a kit for assessing a pluripotency state of cells.

A kit comprising reagents adapted to specifically determine the expression level of a plurality of antigens selected from the group consisting of:
(i) a plurality of CTAs selected from the group consisting of: CEP55, GAGE8/GAGE12F, ZNF165, PRAME, SPAG4, PAGE4, PBK, SPANXA2/B1/C/A1, TSPY8/4/3/1, and GAGE12D/12F;
(ii) a plurality of CTAs selected from the group consisting of: RBM46, CT47A1/A2/A3/A4/A5/A6/A8/A9/A10/A7/A11, PBK, DDX53, MAGEB3, LOC653786/OTOA, DMRT1, LDHC, CCDC83, ANKRD45, DDX53, BAGE, TDRD1, CEP55, PRM1, SSX2B/2, SEMG1, TPTE and SPAG1;
(iii) a plurality of CTAs selected from the group consisting of: MAGEB4, TTK, CEP55, SLCO6A1, PBK, SPA17, ATAD2, FAM133A, TTK, MAGEA1, OIP5, CABYR, SSX1, MAGEA3, SSX2B/2, MAGEA6, MAGEA12, CTNNA2, TPTE, SSX4B/4, XAGE1B/1E, MAGEC1, GAGE8/12F/2A/2D/12J/12G/2B/2E/12I/7/6/E5/4/3/2C/1, GAGE12D/12F/2A/12H/12E/12C/12G/12I/7/6/5/4/2C, and GAGE12F/12G/12I/7/5;
(iv) a plurality of CTAs selected from the group consisting of: FAM133A, MORC1, TEX14, ANKRD45, MAGEB2, MAGEC1 and ELOVL4;
(v) a plurality of CTAs selected from the group consisting of: MAGEA11, ODF2, IL13RA2, MAGEA6, DDX43, CEP55, MAGEA1, MAGEB3, SPANXB1, BAGE, TSGA10, MAGEA3, MAGEA12, MAGEA1, and IL13RA2;
(vi) a plurality of antigens selected from the group consisting of: CEP55, TTK, ATAD2, OIP5, FAM133A, FATE1, IL13RA2, PRAME, MAGEA6, CTNNA2, MAGEA3, PLAC1, PBK, MAGEA12, SPAG4 and ELOVL4;

(vii) a plurality of CTAs selected from the group consisting of: PRAME, CTNNA2, MAGEA2B/MAGEA2, TMEFF1, IGSF11, MAGEA3, SSX1, MAGEA6, MAGEA12, PBK, ANKRD45, SSX4B/SSX4, MAGEC1, SSX2B/SSX2, MAGEA1, MAGEC2, DSCR8, TTK, CTAG1A/CTAG1B, TPTE, XAGE1B/XAGE1E and IL13RA2;

(viii) a plurality of CTAs selected from the group consisting of: ZNF165, PRAME, GAGE1, GAGE12F/G/I/7/5, SPAG1, TTK, LEMD1, SPA17, PBK, TMEFF1, CEP55, CTNNA2, SPAG4, CTCFL, SPAG17, BAGE, ATAD2, PRSS54, GPAT2, CCDC83, MAGEA11, CT45A2/A1/A6/A5/A4/A3, LY6K, TSGA10, DSCR8, CTAG1A/CTAG1B, and SAGE1;

(ix) a plurality of CTAs selected from the group consisting of: TDRD1, POTED, DCAF12 and TSGA10;

(x) a plurality of CTAs selected from the group consisting of: CEP55, GAGE8/12F, SPAG4, LOC653786/OTOA, CTNNA2, TPTE, ATAD2, GAGE8/12F/2A/2D/12J/12G/2B/2E/12I/7/6/5/4/3/2C/1, MAGEA6, MORC1, TTK, PBK, RGS22, TMEFF1, ARX, MAGEB4, PRAME, GAGE12D/2F/2A/12H/12E/12C/12G/12I/7/6/5/4/2C, TEX14, POTED, DMRT1, CTCFL, GPAT2, GAGE12F/12G/2I/E7/E5, GAGE3, SPANXA2/C/A1, DDX43, and GAGE1;

(xi) a plurality of CTAs selected from the group consisting of: DDX43, SSX1, ATAD2 and CEP55; and (xii) a plurality of CTAs selected from the group consisting of: LY6K, MAGEA6, PLAC1, LEMD1, MAGEA1, MAGEA11, MAGEA4, MAGEA12, and CEP55.

According to another aspect, there is provided a kit comprising reagents adapted to specifically determine the expression level of a plurality of antigens selected from the group consisting of:

(i) a plurality of CTAs selected from the group consisting of: ZNF165, GAGE1, PRAME, and GAGE12, (ii) a plurality of CTAs selected from the group consisting of: PBK, XAGE1B, IL13RA2, MORC1, and BAGE2, (iii) a plurality of CTAs selected from the group consisting of: CEP55, SPAG4, CTNNA2, GAGE8, and OTOA, (iv) a plurality of CTAs selected from the group consisting of: RBM46, DDX53, and CT47A1, (v) a plurality of CTAs selected from the group consisting of: TDRD1, DCAF12, POTED, and TSGA10, (vi) a plurality of CTAs selected from the group consisting of: MAGEB4, TTK, and SLCO6A1, (vii) a plurality of CTAs selected from the group consisting of: PRAME and CTNNA2, (viii) a plurality of CTAs selected from the group consisting of: FAM133A, ANKRD45, ELOVL4, MORC1, MAGEB2, TEX14, MAGEC1, (ix) a plurality of CTAs selected from the group consisting of: TTK and PRAME, (x) a plurality of CTAs selected from the group consisting of: PBK, SPAG4, MAGEA12, and ELOVL4, (xi) a plurality of CTAs selected from the group consisting of: LY6K, MAGEA6, PLAC1, and LEMD1, (xii) a plurality of CTAs residing on a non-X chromosome selected from the group consisting of: CEP55, TTK, ATAD2 and OIP5, and a plurality of antigens selected from the group consisting of: FOXM1, UBE2C, MAD2L1, CCNB2, CDC20, CKS2, RRM2 CCNB1, AURKB, ECT2, and NEK2, (xiii) a plurality of CTAs residing on a non-X chromosome selected from the group consisting of: CEP55, PBK and TTK, and a plurality of CTAs residing on the X chromosome selected from the group consisting of: MAGE, GAGE, and SPANX.

In some embodiments, the kit comprises reagents adapted to specifically determine the expression levels of any of the CTAs which are used in the methods of the present invention ('affinity reagents'). In some embodiments, the kit comprises affinity reagents having specific affinity to a single CTA of the pre-determined CTA sets described herein. In one example of such a kit, affinity reagents would be included that will specifically detect any of at least 4, 5, 6, 7, 8, 9, 10, 11,12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 47, 48, 49, 50, 60, 65, 70, 75, 80, 85, 90, 95, 100, 105, 110, 115, 120, 125, 130, 135, 140, 145, 150, 155, 160, 165, or 170 of the CTAs which are used in the methods of the present invention.

In some embodiments, the reagents adapted to specifically determine the expression levels of any of the CTAs of the invention are arranged on a microarray. In some embodiments, include only affinity reagents for detecting gene or protein expression of the genes discussed herein, along with a number of control genes, such as housekeeping genes, for use in normalization of the results. In some embodiments, the microarray would contain no more than about 25, 20, 15, or 10 affinity reagents for control genes or protein products expressed thereby. A microarray for use in the kit of the present invention preferably includes fewer than 2,501 affinity reagents, more preferably fewer than 626, most preferably fewer than 101. In some embodiments, such a microarray includes affinity reagents specific for no more than 10,000, 5,000, 4,000 or 3,000 total affinity reagents. In some embodiments, common microarray such as illumina, affymetrix and other microarray covering up to 25000 genes with many of the genes having 1 to 10 probes, are used.

In some embodiments, the kit comprises reagents adapted to specifically determine the expression level of a plurality of CT antigens selected from a set of CTAs of the invention, or any combination of sets of the invention.

In some embodiments, the reagents are selected from mRNA or cDNA hybridization or amplification reagents, and a plurality of mRNA or cDNA-specific probes or amplification primers. In some embodiments, the kit further comprises detectable tags or labels, solutions for rendering a nucleic acid susceptible to hybridization, solutions for lysing cells, or solutions for the purification of nucleic acids.

In some embodiments, the reagents comprise a plurality of antibodies specific for CTAs of the invention. The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

In some embodiments, the kit further comprises: detectable tags or labels, solutions for rendering a polypeptide susceptible to the binding of an antibody, solutions for lysing cells, or solutions for the purification of CTAs.

The kits can further comprise a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for diagnosing the condition. The label or package insert indicates that the composition is used for in vitro diagnosis of the condition of choice.

According to one aspect the invention provides an expression vector for detecting cancerous cells. In some embodiments, the expression vector encodes a plurality of nucleotide sequences complementary to a plurality of mRNAs of the CTAs which are used in the methods of the present invention. In some embodiments, the plurality of mRNAs-specific probes is further tagged with detectable tags or labels. In some embodiments, the mRNAs-specific probes are conjugated to one or more cytotoxic agents.

Assessing Pluripotent Potential of Cells

In some embodiments, the invention provides a method for assessing a pluripotency state of cells, the method comprises the steps of:
  (a) determining an expression profile of a plurality of antigens selected from the group consisting of: CEP55, GAGE8/GAGE12F, ZNF165, PRAME, SPAG4, PAGE4, PBK, SPANXA2/SPANXB1/SPANXC/SPANXA1, TSPY8/TSPY4/TSPY3/TSPY1, and GAGE12D/GAGE12F, in a non-testis biological sample; and
  (b) comparing the expression profile to a reference expression profile, wherein an amount of increase in expression of the expression profile compared to the reference expression profile correlates with a degree of developmental versatility of said cells.

In some embodiments, the cells may be derived from neonatal tissue, including, but not limited to: umbilical cord tissues (e.g., the umbilical cord, cord blood, cord blood vessels), the amnion, the placenta, or other various neonatal tissues (e.g., bone marrow fluid, muscle, adipose tissue, peripheral blood, skin, skeletal muscle etc.).

The term "pluripotency" or a "pluripotent state" as used herein refers to a cell with the ability to differentiate into all three embryonic germ layers: endoderm (gut tissue), mesoderm (including blood, muscle, and vessels), and ectoderm (such as skin and nerve). Hence, a pluripotent cell has high degree of developmental versatility.

The term "multipotent" when used in reference to a "multipotent cell" refers to a cell that is able to differentiate into some but not all of the cells derived from all three germ layers. Thus, a multipotent cell is a partially differentiated cell. Multipotent cells are well known in the art, and non-limiting examples of multipotent cells can include adult stem cells, such as for example, hematopoietic stem cells and neural stem cells. Multipotent means a stem cell may form many types of cells in a given lineage, but not cells of other lineages. For example, a multipotent blood stem cell can form the many different types of blood cells (red, white, platelets, etc.), but it cannot form neurons. The term "multipotency" refers to a cell with the degree of developmental versatility that is less than totipotent and pluripotent.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise", "include" and "have" and conjugates thereof, are used to indicate that the object or objects of the verb are not necessarily a complete listing of components, elements or parts of the subject or subjects of the verb.

Other terms as used herein are meant to be defined by their well-known meanings in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); "Bacteriophage Methods and Protocols", Volume 1: Isolation, Characterization, and Interactions, all of which are incorporated by reference. Other general references are provided throughout this document.

Various embodiments and aspects of the present invention as delineated hereinabove and as claimed in the claims section below find experimental support in the following examples. Reference is now made to the following examples, which together with the above descriptions illustrate some embodiments of the invention in a non-limiting fashion.

Materials and Methods

Volcano analysis: Volcano analysis is a special 2D view of data which is split into 2 groups, such as responders to a treatment vs. non-responders or cancer group versus normal healthy group. For each gene, a fold ratio between the groups and its p-value (after 1000 permutation in a t-test) is depicted. Y axis is p-value where the higher the value the better (smaller) is the p value. The X axis is the fold change. Right direction represents up regulation, and left direction represents down regulation. Since CTA of interest are the up-regulated ones, the genes in the right side with p-values greater than 2 and p-value of less than 0.05 were selected.

Ranking method: The ranking method is based on performing a sequential selection of genes for obtaining an optimal set with the highest accuracy and minimal number of selections. The assumption is that a group of CTA genes are highly up regulated in comparison to their normal average with high variability on a large set of patients (2, 3, 4, 5 . . . 30). Thus, a ranking algorithm is used. The ranking is on the basis of fold change compared to average of all normal controls. The program ranks each of the CTA gene members as to how many patients have a fold change greater than 2, 3, 4, . . . , 30 and creates a matrix. Then the gene with the largest number of cases with fold change greater than five (5) is chosen. Those patients fulfilling the condition are removed and the process is repeated without them. This is repeated until no patients are left. This guarantees no highly correlated genes, a minimal number of genes and an optimal signature, giving each gene the opportunity to compete. As a non-limiting example: 1090 patients (out of 2155) have an expression in gene CEP55 which is greater than five times the its average value in all the 449 norm patients. The gene is selected the 1090 are removed from the table and the ranking repeats on the 1056 remaining patients. This time GAGE8 has the highest score with 206 (out of 1056) people having his expression increase by more than 5 times compared to average normal. The gene is selected and we remain to go on with ranking 850 people. After selecting 6 genes CEP55 (1090 people), GAGE8 (206), ZNF165 (146), PRAME (114), SPAG4 (78), 1634 people were removed. The remaining 521 are removed with the selection of 4 more genes going on sequentially with the same process.

TABLE 1

Exemplary table for the ranking process

| | CEP55 | TTK | PBK | ZNF165 | PRAME | ATAD2 |
|---|---|---|---|---|---|---|
| fold_2 | 1673 | 1599 | 1564 | 1605 | 934 | 1350 |
| fold_3 | 1443 | 1378 | 1346 | 1258 | 792 | 981 |
| fold_4 | 1236 | 1210 | 1158 | 999 | 715 | 750 |
| fold_5 | 1090 | 1065 | 1016 | 803 | 642 | 561 |

| | GAGE8/GAGE12F/GAGE2A/GAGE2D/GAGE2J/GAGE12G/GAGE2B/GAGE2E/GAGE12I/GAGE7/GAGE6/GAGE5/GAGE4/GAGE3/GAGE2C/GAGE1 | PRAME | ZNF165 | SPAG4 | TTK | PBK |
|---|---|---|---|---|---|---|
| fold_2 | 714 | 336 | 631 | 410 | 515 | 488 |
| fold_3 | 487 | 260 | 397 | 272 | 312 | 315 |
| fold_4 | 308 | 223 | 249 | 207 | 196 | 190 |
| fold_5 | 206 | 188 | 170 | 155 | 123 | 120 |

| | ZNF165 | PRAME | SPAG4 | PBK | TTK | SPANXA2/SPANXB1/SPANXC/SPANXA1 |
|---|---|---|---|---|---|---|
| fold_2 | 517 | 259 | 335 | 392 | 409 | 269 |
| fold_3 | 335 | 200 | 225 | 253 | 242 | 198 |
| fold_4 | 211 | 169 | 173 | 151 | 156 | 120 |
| fold_5 | 146 | 142 | 127 | 100 | 99 | 74 |

| | PRAME | SPAG4 | TTK | PBK | PAGE4 | SPANXA2/SPANXB1/SPANXC/SPANXA1 |
|---|---|---|---|---|---|---|
| fold_2 | 216 | 261 | 311 | 291 | 82 | 221 |
| fold_3 | 164 | 181 | 179 | 182 | 71 | 159 |
| fold_4 | 138 | 139 | 109 | 97 | 67 | 91 |
| fold_5 | 114 | 105 | 67 | 64 | 63 | 54 |

TABLE 1-continued

Exemplary table for the ranking process

| | SPAG4 | PAGE4 | TSPY8/TSPY4/TSPY3/TSPY1 | TTK | SPANXA2/SPANXB1/SPANXC/SPANXA1 | PBK |
|---|---|---|---|---|---|---|
| fold_2 | 208 | 75 | 126 | 244 | 191 | 223 |
| fold_3 | 138 | 67 | 90 | 134 | 135 | 134 |
| fold_4 | 105 | 63 | 62 | 76 | 74 | 70 |
| fold_5 | 78 | 60 | 45 | 44 | 43 | 42 |

Example 1

A CTA Signature for Cancer Diagnosis

Expression of CTA genes was analyzed in 449 non-cancer subjects and 2155 cancer subjects having one of 166 different cancers.

The analyzed cancerous samples included 166 different types of cancerous tissues, they are: Abdominal mass, Abdominal wall, Abdominal wall fascia, Abdominal wall mass, Abdominal Wall Soft Tissue, Abdominal/Pelvic Tissue Abdominal-pelvic mass, Acetabulum, Acetabulum and pelvic soft tissues, Adrenal gland, Appendix, Ascending Colon, Axillary lymph node, Bladder, Bone, Bone & Cartilage, Brain, Branchial Cleft Cyst, Breast, Breast dermal mass, Bronchus and Lung, Cecum, Cerebellar tissue, Cervical Lymph Node, Cervix, Cervix Uteri, Chest Wall, Chest wall mass, Colon, Colon mesentery, Common Bile Duct, Conncective tissue of abdomen, Connective tissue of abdomen, Corpus Uteri, Dermal and subcutaneous fat and lymph nodes from neck dissection, Duodenum, Endocervix, Endometrium, Esophagus, Exocrine Pancreas, Fallopian Tube, Femoral Lymph Node, Gallbladder, Gastroesophageal junction, GI Tract Connective Tissue, Head of Pancreas, Hemidiaphragm, Hepatic Flexure, Humerus bone, Ileum, Iliac bone & soft tissue, Iliac Lymph Node, Inguinal Lymph Nodes, Islets of Langerhans, Jejunum, Kidney, Kidney and Ureter, Adnexa, axillary lymph node, pelvic sidewall, Left Lower Lobe Lung, Liver, Liver or Omentum, LUL Lung, Lung, Lymph Node, Lymph node neck, Lymph Nodes, Mesenteric Lymph Node, Myometrium, Neck mass, Omentum, Omentum or Pelvic Mass, Ovary, Ovary or Omentum, Pancreas, Para aortic tissue, Parametrial Implant, Parietal Pleura, Parotid Gland, Parotid Lymph Node, Pectoral Muscle, Pelvic lymph node, Pelvic mass, Pelvic sidewall nodule, Pelvic Soft Tissue, Pelvic Tissue, Pelvic Tumor, Penis, Perihepatic adipose tissue, Perihepatic Mass, Peritoneum, Pleural Nodule, Popliteal soft tissue, Prostate, Prostate Gland, adnexa or metastatic transverse colon nodule, chest wall mass, hip/buttock mass, thigh mass, Rectosigmoid, Rectosigmoid Colon, Rectosigmoid Junction, Rectum, Renal Pelvis, Retroperitoneal Mass, Retroperitoneum, Rib, Right Colon, Sigmoid colon, Skin, skin from abdomen, Small bowel, Small Intestine, Soft Tissue Abdominal Mass, Soft Tissue Abdominal Wall, Soft Tissue Thigh, Soft Tissue Upper Arm, Soft Tissue Left Buttock, Soft tissue of abdomen, Soft tissue of arm, Soft tissue of hip, Soft Tissue of Knee, Soft Tissue of Leg, Soft Tissue of Neck, Soft Tissue of Retroperitoneum, Soft tissue of shoulder, Soft Tissue of thigh, Soft Tissue Knee, Soft Tissue Thigh, Spinal cord, Spleen, Stomach, Stomach (Gastroesophageal junction), Superior mediastinal lymph node, Supraclavicular Lymph Node, Testis, Thoracic spine bone and intervertebral disc, Thyroid, Tongue, Transverse colon nodule, Unspecified soft tissue from abdomen or pelvis, Upper Back Soft Tissue, Ureter, Ureterovesicle junction, Urethral Nodule, Urinary Bladder, Urinary Tract, Uterine Cervix, Uterine Corpus, Uterine Serosa, Uterine/Bladder Tumor, Uterus, Uterus and cervix, Uterus, Vagina, Vaginal mass, Vaginal Wall, Vulva, and Vulvar lesion.

The non-cancerous tissues examined include samples obtained from: accumbens, adipose tissue, adipose tissue omental, adipose tissue subcutaneous, adrenal gland cortex, amygdala, aorta, bone marrow, breast, bronchus, caudate, cerebellar hemisphere, cerebellar vermis, cerebellum, cerebral cortex, cervix, colon, colon cecum, coronary artery, corpus callosum, deltoid muscle, dorsal root ganglia, endometrium, esophagus, fallopian tube, fetal brain, fetal liver, frontal cortex, frontal lobe, globus pallidus, gloubus pallidum external, gloubus pallidum internal, heart, heart atrium, heart ventricle, hippocampus, hypothalamus, joint tissue synovium, kidney, kidney cortex, kidney medulla, liver, lung, lymph nodes, mammary gland, medulla midbrain, myometrium, nipple cross section, nodose nucleus, occipital lobe, oral mucosa, ovary, pancreas, parietal lobe, penis, pericardium, peritneum, pharyngeal mucosa, pituitary gland, placenta, pons, prefrontal cortex, prostate gland, putamen, retrocervical infiltrate, salivary gland, saphenous vein, skeletal muscle, skeletal muscle-superior quadracep, skin, small intestine, small intestine duodenum small intestine jejunum, spinal cord, spleen, stomach, stomach cardiac, stomach fundus, stomach pyloric, substantia nigra pars compacta, substantia nigra reticulata, substantia nigra, subthalamic nucleus, synovial membrane, temporal lobe, thalamus, thalamus lateral nuclei, thalamus subthalamic nucleus, thyroid gland, tongue, tongue main corpus, tongue superior part w/papillae, tonsil, trachea, trigeminal ganglia, urethra, uterus, vagina, vena cava, ventral tegmental area, vestibular nuclei superior, and vulva.

Ranked statistical analyses were conducted in order to identify CTA genes exhibiting increased expression in all cancerous samples (166 different types of cancers), as well as in samples from specific cancers (breast, liver, multiple myeloma, glioblastoma, colon, adrenal, melanoma, ovarian, prostate and kidney) as compared to non-cancerous samples taken from individuals which are not afflicted with cancer.

Figure 1K:
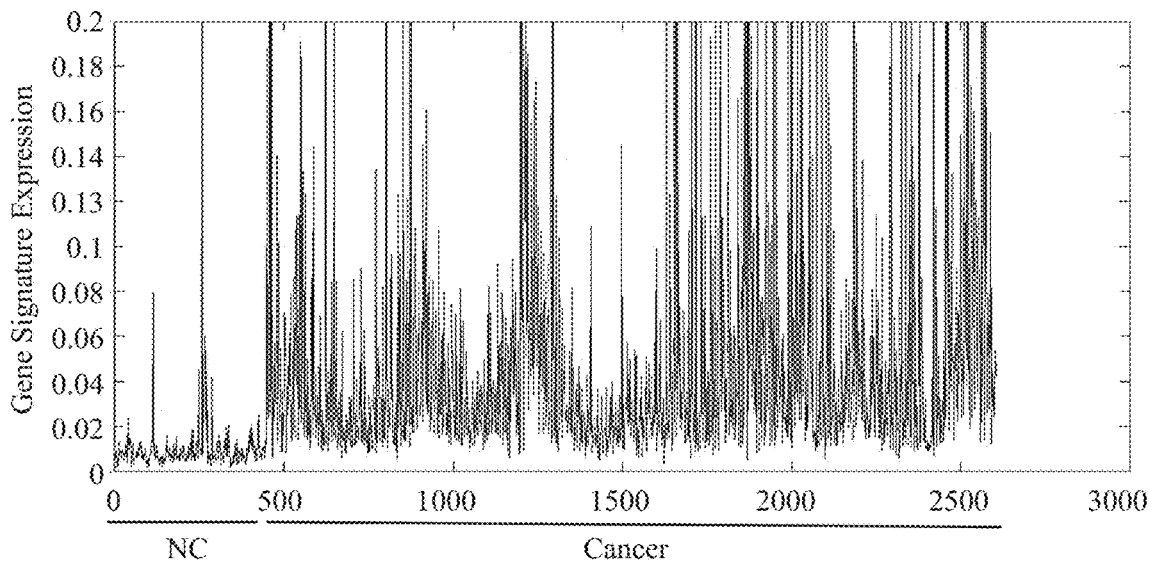

The CTA genes that were found to identify cancers in general, as well as in specific cancers, can be found in Table 2. As can be seen in FIGS. 1A-J, the genes CEP55, GAGE8/12F, ZNF165, PRAME, SPAG4, PAGE4, PBK, SPANXA1/A2/B1/C, TSPY1/3/4/8, and GAGE12D/F, had high-ranking scores when assessing all cancers. Some probes recognize multiple potential target sequences, in this case members of the same gene family are indicated by a slash "/" between their names. It was found that a sum of the fold changes of these genes in a test sample could be compared to standard expression in non-cancerous samples, and if the fold change was higher than a predetermined threshold the test sample could be positively identified as cancerous (FIG. 1K).

Figure 1L:
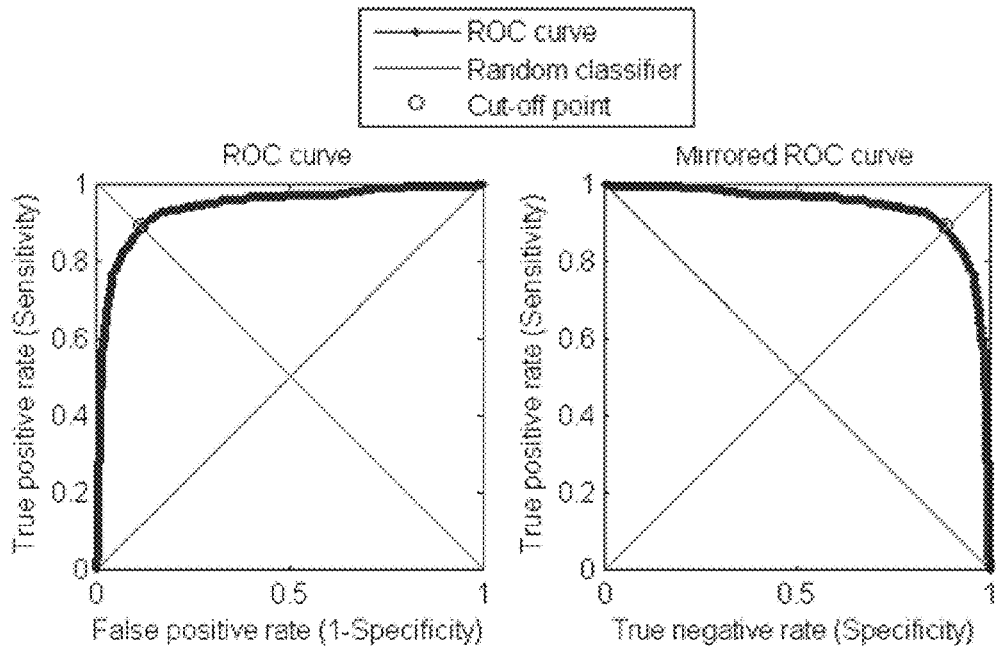

An ROC curve analysis (FIG. 1L) for using the sum of fold increases of these genes to differentiate between cancer patients and non-cancerous individuals, was performed. The cut-off point, for best sensitivity and specificity of the ROC curve analysis, resulted in a sensitivity of 89.5% with a 95% confidence interval of 86.7%-92.4% and false negative proportion of 10.5%, and a specificity of 88.5% with a 95% confidence interval of 87.2%-89.9% and a false positive proportion of 10.5%. The area under the curve of the ROC analysis was found to be 0.94496, indicating the high accuracy of this test.

As summarized in Table 3, as the sum increase in expression of the 10 CTAs increases ("threshold" measures the minimum the sum must increase), accuracy for detecting cancer increases. A sum signature of expression refers to the total expression of the group of 10 CTAs. For a threshold increase of 0.06 in the sum signature of expression there are 558 cancer subjects and no non-cancer subjects detected, thus this is the minimum increase required for 100% accuracy (also called specificity). Further, for a threshold increase of 0.015 there are 1831 cancer subjects and 36 non-cancer subjects detected as having a positive signature. Thus, a cancer case is detected with an accuracy of 98% using this threshold (0.015) and a false positive rate of 2%. In summary, this global signature can for example spot a cancer in 70% of the 2155 patients having one of 166 different cancers, with an accuracy of 98.56% using a threshold of 0.02.

TABLE 3

Accuracy of determining cancer

| Threshold | Number of cancer subjects above threshold | Number of non-cancer subjects above threshold | Accuracy of detecting cancer |
|---|---|---|---|
| 0.01 | 2078 | 117 | 94.66 |
| 0.013 | 1943 | 60 | 97 |
| 0.015 | 1831 | 36 | 98 |
| 0.02 | 1511 | 22 | 98.56 |

Example 2

A CTA Signature for Detecting Liver Cancer

Firstly, statistical analyses using volcano plots were conducted in order to identify CTA genes exhibiting increased expression in specific cancer (breast, liver, multiple myeloma, glioblastoma, colon, adrenal, melanoma, ovarian, prostate and kidney) samples as compared to non-cancerous samples that were taken from the same individual. Liver cancer samples from 11 individuals were tested. Table 4 presents the genes that demonstrated at least a 2-fold increase (fold change, FC) in expression, with a P-value threshold of 0.05.

TABLE 4

CTA genes demonstrating increased expression in liver cancer samples

| Gene | P-Value | FC |
|---|---|---|
| PBK | 2.10E−05 | 6.08 |
| SPA17 | 3.25E−05 | 2.21 |
| ATAD2 | 1.84E−04 | 2.05 |
| FAM133A | 8.20E−04 | 4.41 |
| TTK | 8.58E−04 | 4.57 |
| MAGEA1 | 1.04E−03 | 7.44 |
| CEP55 | 2.19E−03 | 3.02 |
| OIP5 | 4.11E−03 | 2.19 |
| SLCO6A1 | 8.59E−03 | 2.31 |
| CABYR | 1.04E−02 | 2.88 |
| SSX1 | 1.62E−02 | 3.28 |
| MAGEA3 | 1.73E−02 | 6.50 |
| SSX2/2B | 1.74E−02 | 2.85 |
| MAGEA6 | 1.80E−02 | 6.63 |
| MAGEA12 | 1.91E−02 | 5.10 |
| CTNNA2 | 2.29E−02 | 4.45 |
| TPTE | 2.67E−02 | 3.43 |
| SSX4/4B | 3.18E−02 | 3.02 |
| XAGE1B/E | 3.72E−02 | 2.38 |
| MAGEC1 | 4.44E−02 | 2.96 |
| GAGE1/2A/2B/2C/2D/2E/3/4/5/6/7/8/12F/12G/12I/12J | 4.49E−02 | 6.06 |
| GAGE2A/2C/4/5/6/7/12C/12D/12E/12F/12G/12H/12I | 4.60E−02 | 5.29 |
| GAGE5/7/12F/12G/12I | 4.82E−02 | 5.37 |

Further, clusters of highly correlated genes that demonstrate expression values that have a sufficient degree of correlation as to allow their interchangeable use for detecting liver cancer, are presented in Table 5. For example, determination of an expression level of TTK may be substituted by determination of an expression level of PBK (see, Table 5, Liver, Cluster 4).

TABLE 5

Clusters of highly correlated genes

Gene name (correlation of expression to the 1st gene)

All Cancers

| | |
|---|---|
| Cluster 1.1 | CEP55 (1), OIP5 (0.782), TTK (0.766), CASC5 (0.764), PBK (0.747) |
| Cluster 1.2 | CTAG1A/B (1), CTAG2 (0.881) |
| Cluster 1.3 | DCAF12 (1), RQCD1 (0.746) |
| Cluster 1.4 | GAGE2A/2C/4/5/6/7/12C/12D/12E/12F/12G/12H/12I (1), GAGE1/2A/2C/2D/2E/4/5/6/7/8/12C/12D/12E/12F/12G/12H/12I/12J (0.998), GAGE5/7/12F/12G/12I (0.997), GAGE1/4/5/6/7/12F/12G/12I/12J (0.995), GAGE1/2A/2B/2C/2D/2E/3/4/5/6/7/8/12F/12G/12I/12J (0.994), GAGE3 (0.982) |
| Cluster 1.5 | MAGEA12 (1), MAGEA2B (0.908), MAGEA6 (0.886), MAGEA3 (0.866), MAGEA5 (0.787) |
| Cluster 1.6 | MAGEA5 (1), MAGEA6 (0.817), MAGEA3 (0.793), MAGEA12 (0.787), MAGEA2B (0.763) |
| Cluster 1.7 | OIP5 (1), CASC5 (0.827), CEP55 (0.782), TTK (0.748), PBK (0.726) |
| Cluster 1.8 | PRSS55 (1), ZNF645 (0.767) |

TABLE 5-continued

Clusters of highly correlated genes

Gene name (correlation of expression to the 1st gene)

| | |
|---|---|
| Cluster 1.9 | PQCD1 (1), ODF2 (0.782), DCAF12 (0.746) |
| Cluster 1.10 | SPA17 (1), ARMC3 (0.820), TSGA10 (0.719), SPEF2 (0.710) |
| Cluster 1.11 | SPANXA1/A2/B1/C (1), SPANXC (0.989), SPANXA1/A2/C (0.976), |
| Cluster 1.12 | SSX1 (1), SSX4/4B (0.981), SSX3 (0.972), SSX2/2B (0.960), SSX5 (0.904) |
| Cluster 1.13 | TTK (1), CEP55 (0.766), OIP5 (0.748), CASC5 (0.723) |
| Liver | |
| Cluster 2.1 | GAGE1/2A/2B/2C/2D/2E/3/4/5/6/7/8/12F/12G/12I/12J (1), GAGE5/7/12F/12G/12I (0.999), GAGE2A/2C/4/5/6/7/12C/12D/12E/12F/12G/12H/12I (0.999), XAGE1B/E (0.930), MAGE16 (0.851), MAGEA3 (0.844), MAGEA12 (0.820) |
| Cluster 2.2 | CEP55 (1), OIP5 (0.923), TTK (0.837) |
| Cluster 2.3 | MAGEA1 (1), SSX1 (0.802) |
| Cluster 2.4 | PBK (1), TTK (0.845) |
| Cluster 2.5 | TTK (1), CEP55 (0.711), OIP5 (0.701) |
| Cluster 2.6 | PBK (1), OIP5 (0.919), CEP55 (0.833), HORMAD1 (0.717), ELOVL4 (0.709) |
| Cluster 2.7 | MAGEA3 (1), MAGEA6 (0.984), MAGEA2/A2B (0.949), MAGEA5 (0.859) |
| Cluster 2.8 | ATAD2 (1), TFDP3 (0.871), MAGEA1 (0.836), MAGEA5 (0.803) |
| Kidney | |
| Cluster 3.1 | ATAD2 (1), TTK (0.832), CEP55 (0.822) |
| Lung | |
| Cluster 4.1 | MAGEA3 (1), MAGEA6 (0.996), MAGEA2/A2B (0.860) |
| Cluster 4.2 | ATAD2 (1), CEP55 (0.812) |
| Adrenal | |
| Cluster 5.1 | CEP55 (1), PBK (0.805), ATAD2 (0.753), OIP5 (0.7139) |
| Cluster 5.2 | PBK (1), ATAD2 (0.825), CEP55 (0.805) |
| Cluster 5.3 | ATAD2 (1), PBK (0.825), CEP55 (0.753) |
| Cluster 5.4 | PRAME (1), MAGEA6 (0.756), MAGEA3 (0.740) |
| Cluster 5.5 | MAGEA6 (1), MAGEA3 (0.997), MAGEA12 (0.917), PRAME (0.756) |
| Colon | |
| Cluster 6.1 | MAGEA3 (1), MAGEA6 (0.992), MAGEA12 (0.889) |
| Cluster 6.2 | MAGEA6 (1), MAGEA3 (0.992), MAGEA12 (0.894 |
| Cluster 6.3 | MAGEA12 (1), MAGEA3 (0.889), MAGEA6 (0.894) |
| Melanoma | |
| Cluster 7.1 | MAGEA1 (1), XAGE1B/E (0.856), TPTE (0.804) |
| Cluster 7.2 | MAGEA2/2B (1), SSX1 (0.944), MAGEA6 (0.907), IGF11 (0.897) |
| Cluster 7.3 | DSCR8 (1), MAGEA12 (0.864) |

The CTA genes PBK, SPA17, ATAD2, FAM133A and MAGEA1, that exhibit the highest fold increase and the lowest P values (see Table 4), were used for further analysis. It should be noted that since TTK and PBK were found to be highly correlated genes (see Table 5) TTK was not used for further analysis. It was found that the sum of the fold increases in expression of PBK, SPA17, ATAD2, FAM133A and MAGEA1 between liver cancer tissues and non-cancerous tissues of each patient ranged from $2^5$ to $2^{13}$ (FIG. 1K).

Figure 2:
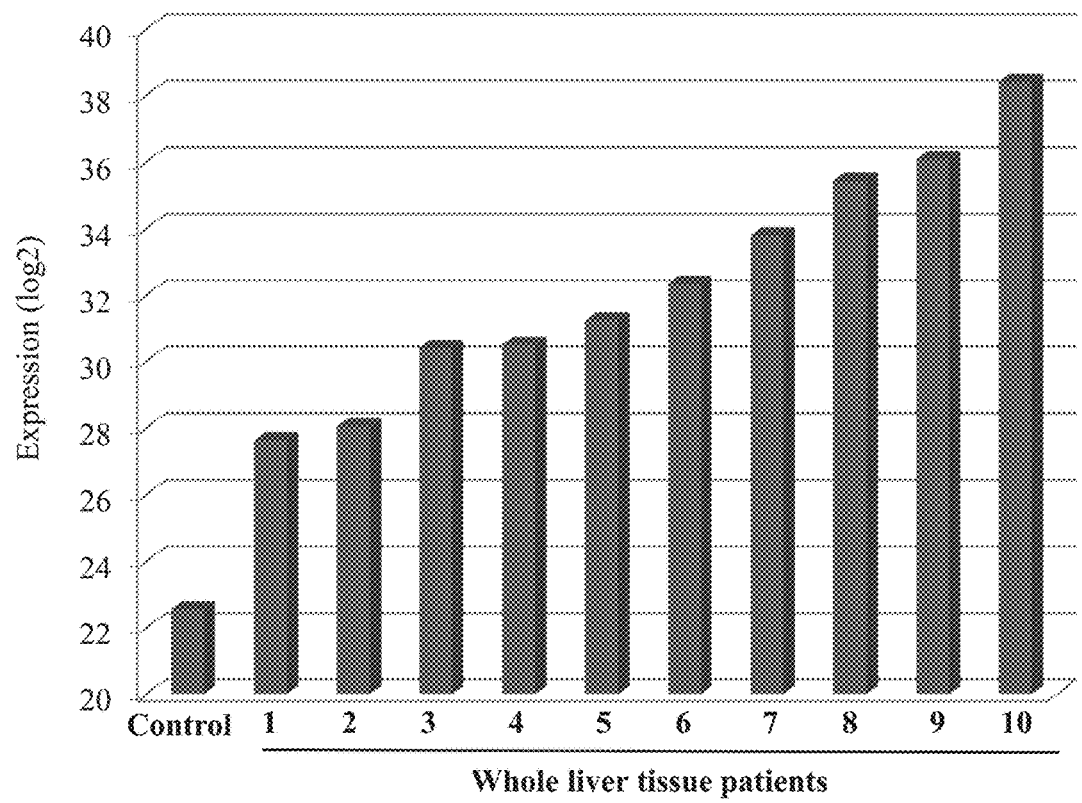
FIG. 2 is a bar graph showing the sum of log 2 expression values of PBK, SPA17, ATAD2, FAM133A and MAGEA1 in normal patients (control) and in 10 individual liver cancer patients.

The sum of log 2 expression values of PBK, SPA17, ATAD2, FAM133A and MAGEA1 in normal patients (control) and in 10 individual cancer patients, is shown in FIG. 2. As had been done before, statistical analyses using volcano plots were conducted in order to identify CTA genes exhibiting increased expression in cancerous samples, but for this second analysis the samples were compared to non-cancerous samples taken from individuals which are not afflicted with cancer. Table 6 presents the genes that demonstrated at least a 2-folds increase in expression, with a P value threshold of 0.05.

TABLE 6

CTA genes demonstrating increased expression in liver cancer patients vs. non-cancerous individuals.

| Gene | P-Value | FC |
|---|---|---|
| MAGEB4 | 2.14E−13 | 6.224045 |
| TTK | 5.51E−10 | 10.71485 |
| SLCO6A1 | 2.51E−09 | 9.067909 |
| CEP55 | 1.87E−07 | 33.4099 |
| TMEFF1 | 1.87E−07 | 3.35633 |
| SPAG4 | 5.83E−07 | 9.988404 |
| GPATCH2 | 1.72E−06 | 2.209838 |
| SPAG1 | 5.24E−06 | 6.458305 |
| PBK | 2.75E−05 | 8.984222 |
| SSX7 | 3.15E−05 | 3.141749 |
| ZNF165 | 3.26E−05 | 7.825225 |
| CTNNA2 | 0.000105 | 3.198691 |
| SPANXA1/A2/B1/C | 0.000239 | 2.950634 |
| SPA17 | 0.000268 | 2.050225 |
| ARX | 0.00055 | 3.689407 |
| TEX101 | 0.000599 | 2.622375 |
| OIP5 | 0.000766 | 2.767701 |
| BAGE | 0.00095 | 2.097327 |
| ADAM2 | 0.001933 | 2.78834 |
| TPTE | 0.002554 | 3.799161 |
| TSPY1/3/4/8 | 0.003842 | 5.012224 |
| IGSF11 | 0.003894 | 2.991969 |
| SPANXA2-OT1 | 0.004857 | 2.456417 |

TABLE 6-continued

CTA genes demonstrating increased expression in liver cancer patients vs. non-cancerous individuals.

| Gene | P-Value | FC |
|---|---|---|
| MAGEA3 | 0.004929 | 27.59158 |
| MAGEA6 | 0.005461 | 37.52972 |
| LOC653786/OTOA | 0.007236 | 2.810354 |
| MAGEA2/2B | 0.007548 | 22.95135 |
| ELOVL4 | 0.016667 | 5.127799 |
| ATAD2 | 0.021821 | 5.746095 |
| HORMAD1 | 0.022018 | 7.143033 |
| GAGE1 | 0.024201 | 3.503409 |
| MAGEA1 | 0.030876 | 3.910258 |
| MAGEA5 | 0.03452 | 2.088143 |
| MAGEA4 | 0.036532 | 3.058595 |
| TFDP3 | 0.041749 | 4.128752 |
| ACTL8 | 0.042094 | 2.961209 |

Further, clusters of highly correlated genes were identified. Table 5 presents 4 more clusters (5-8) of highly correlated genes in liver cancer.

The CTA genes MAGEB4, TTK and SLCO6A1, that exhibit the highest fold increase and the lowest P values (see Table 6), were used for further analysis.

Figure 3A:
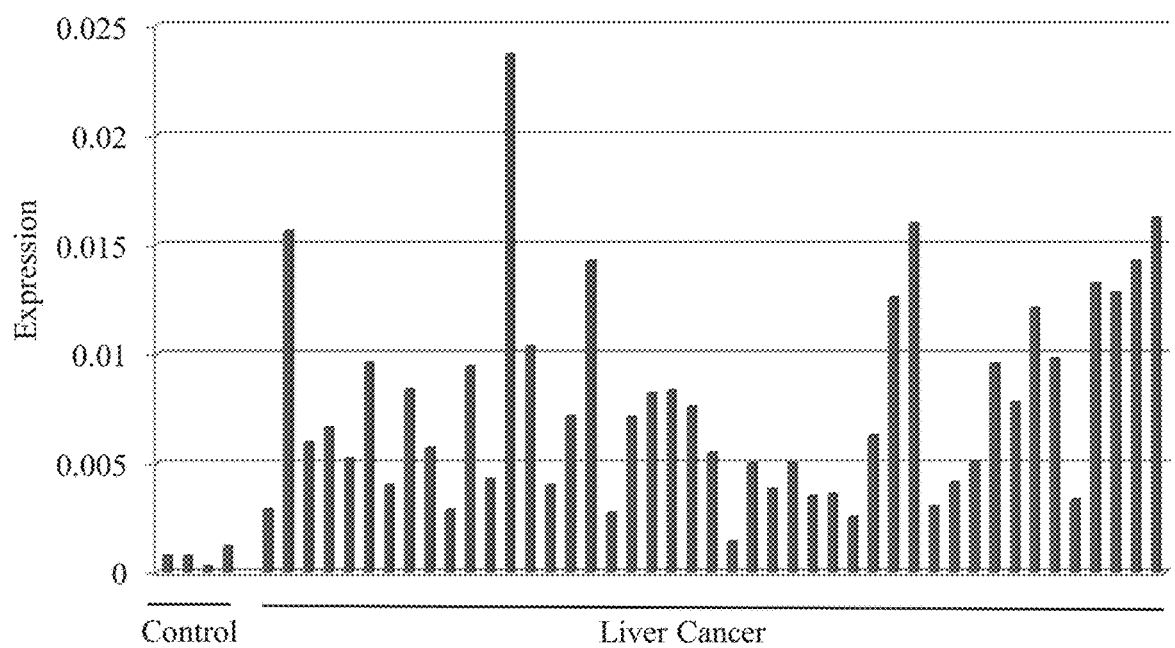
FIGS. 3A-3C.
Figure 3B:
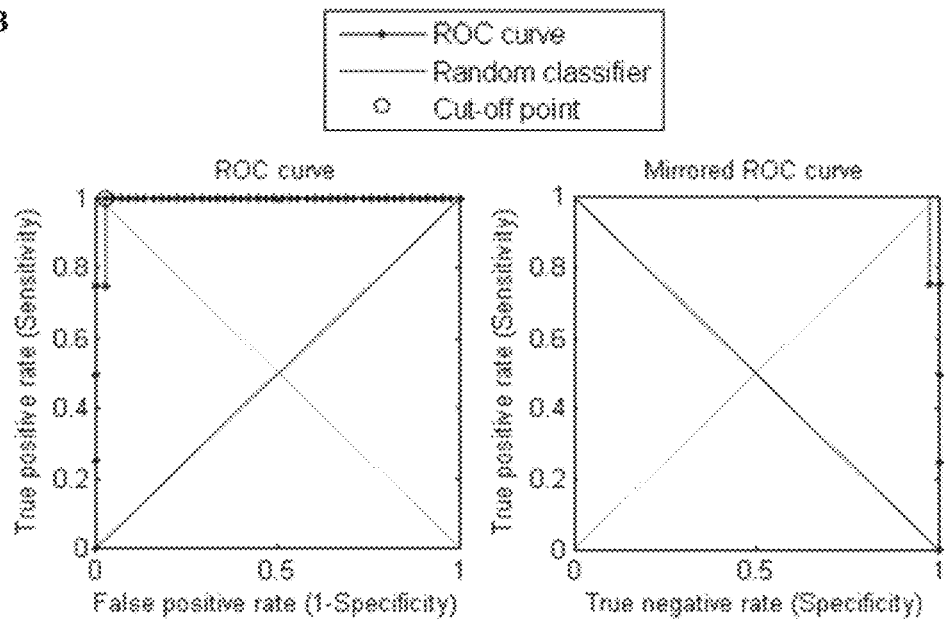
Figure 3C:
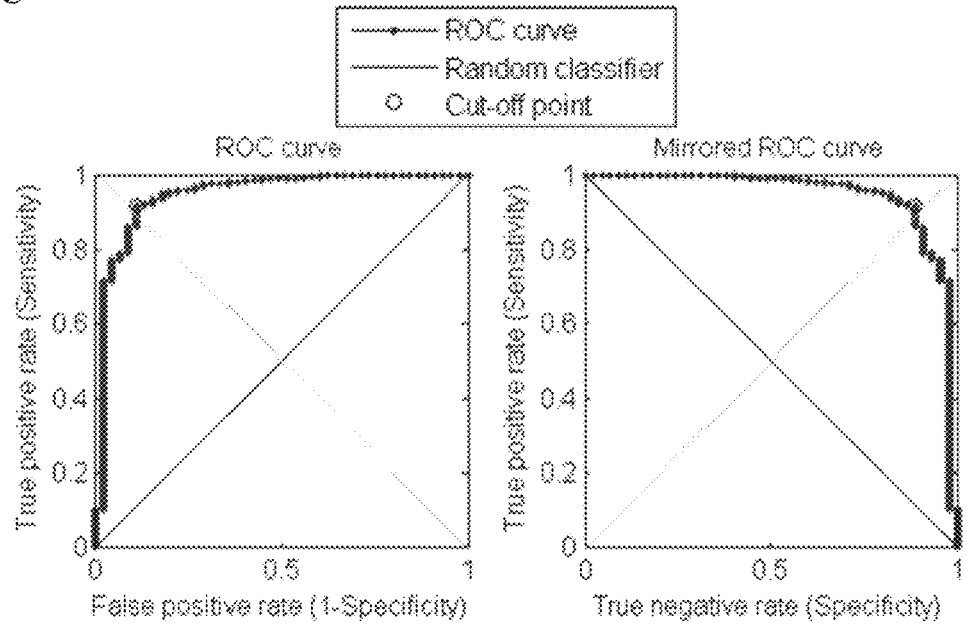

It was found that the sum folds increase of MAGEB4, TTK and SLCO6A1 may be used to differentiate between samples taken from cancer patients and samples taken from non-cancer individuals (FIG. 3A). The accuracy obtained using the sum of fold increases of MAGEB4, TTK and SLCO6A1 to differentiate between normal and cancer patients is 100% (FIG. 3B). In contrast, using a randomized set of CTAs including TTK, PBK, CEP55, ZNF165, ATAD2, SPAG1, MAGEA6 and GAGE12D, resulted in a lower accuracy (FIG. 3C).

Figure 4A:
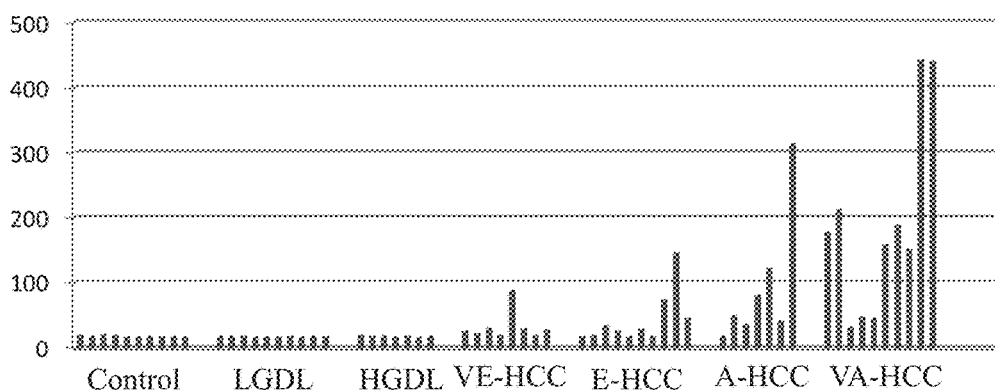
FIGS. 4A-B: 4A is a bar graph demonstrating correlation between increase in a value of the sum folds increase of MAGEB4, TTK and SLCO6A1 and a disease stage/severity. 4B is a heat map demonstrating correlation between increase in expression of OIP5, PBK, CEP55, CC6A1, AGEB4 and TTK and a disease stage/severity. Control, normal tissue; LGDL, low-grade dysplastic liver; VE-HCC, high-grade dysplastic liver, HGDL; very early hepatocellular carcinoma; E-HCC, early hepatocellular carcinoma; A-HCC, advanced hepatocellular carcinoma; VA-HCC, very advanced hepatocellular carcinoma.
Figure 4B:
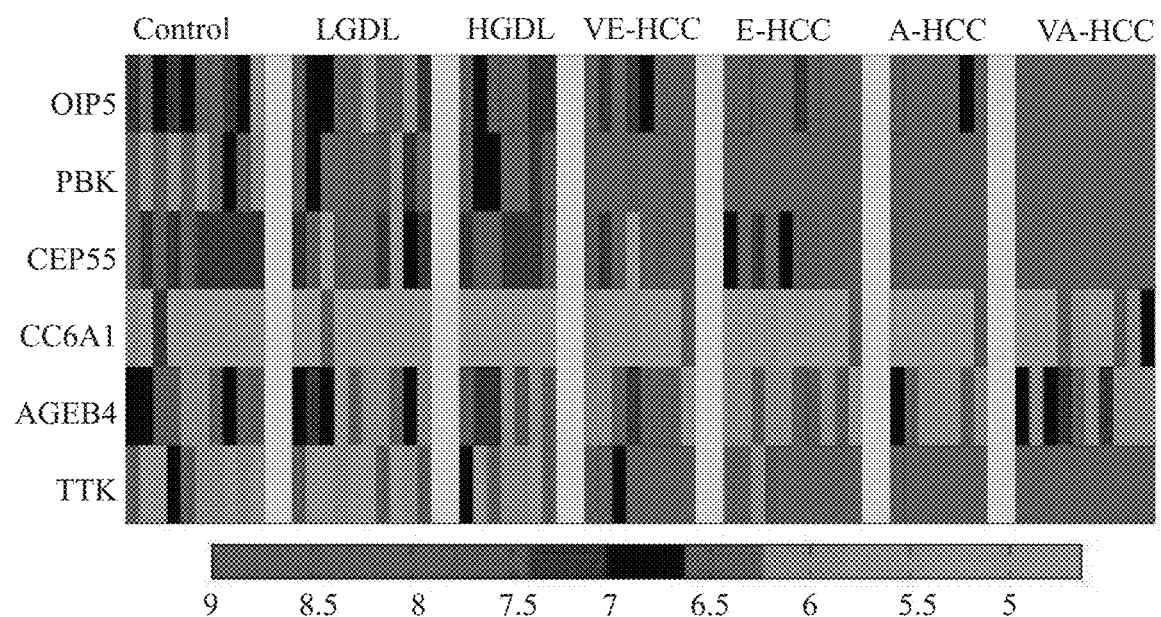

It was further demonstrated that the sum of fold increases of MAGEB4, TTK and SLCO6A1 correlates with an increase in severity of the cancer (FIGS. 4A and 4B).

Table 7 presents the results of both volcano analyses described above (analysis 1 within one subject, analysis 2 cancerous vs healthy subjects). As demonstrated in Table 7, the level of expression change is similar in the key CTAs even though the comparison is made using different controls. This is due to the fact that in both groups the change is from normal to cancer. In all further experiments, reference will only be made to comparing cancer patients to non-cancer patients.

TABLE 7

CTA genes demonstrating increased expression in liver cancer tissues compared to non-cancerous tissues and in cancer patients compared to non-cancer individuals.

| | Analysis No. 1 | | Analysis No. 2 | |
|---|---|---|---|---|
| Gene name | P value | Folds increase | P value | Folds increase |
| PBK | 2.10E−05 | 6.081217 | 2.75E−05 | 8.984222 |
| SPA17 | 3.25E−05 | 2.212338 | 0.000268 | 2.050225 |
| ATAD2 | 0.000184 | 2.04996 | 0.021821 | 5.746095 |
| TTK | 0.000858 | 4.565035 | 5.51E−10 | 10.71485 |
| MAGEA1 | 0.001042 | 7.43634 | 0.030876 | 3.910258 |
| CEP55 | 0.002186 | 3.01749 | 1.87E−07 | 33.4099 |
| OIP5 | 0.00411 | 2.187082 | 0.000766 | 2.767701 |
| SLCO6A1 | 0.008594 | 2.313521 | 2.51E−09 | 9.067909 |
| MAGEA3 | 0.017317 | 6.504792 | 0.004929 | 27.59158 |
| MAGEA6 | 0.017962 | 6.631704 | 0.005461 | 37.52972 |
| CTNNA2 | 0.022883 | 4.453263 | 0.000105 | 3.198691 |
| TPTE | 0.026682 | 3.434725 | 0.002554 | 3.799161 |

Figure 5:
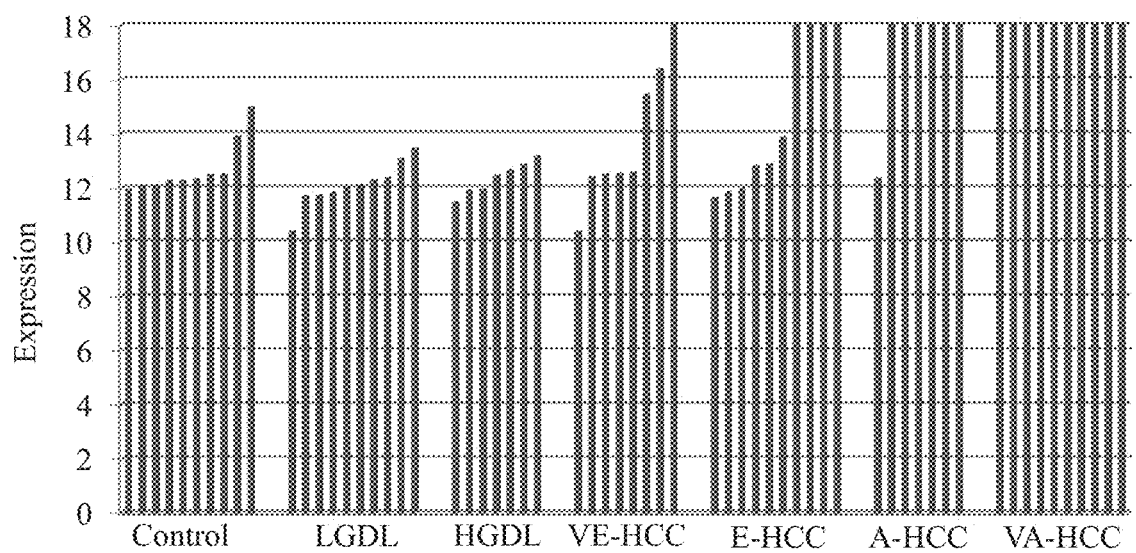
FIG. 5 is a bar graph demonstrating correlation between increase in a value of the sum folds increase of CEP55 and SLCO6A1 and a disease stage/severity.

Further, statistical analyses using the ranking method were conducted in order to identify CTA genes exhibiting increased expression in cancerous samples taken from cancer patients as compared to non-cancerous samples taken from healthy individuals. SLCO6A1 and CEP55 were found to be sufficient for detecting liver cancer (Table 8 and FIG. 5). The sensitivity (sen.) and specificity (spec.) are given at examined informative cut-off values. It should be noted that based on the cluster of highly correlated genes (Table 5, Liver, Cluster 2), analysis of CEP55 expression may be substituted with that of TTK and OIP5.

TABLE 8

ROC curve data for CTA signatures

| Cut-off | Sen. | Spec. |
|---|---|---|
| Liver | | |
| 2.00E−04 | 1.00 | 0.00 |
| 2.00E−04 | 1.00 | 0.25 |
| 3.00E−04 | 1.00 | 0.50 |
| 4.00E−04 | 1.00 | 0.75 |
| 8.00E−04 | 1.00 | 1.00 |
| 1.70E−03 | 0.98 | 1.00 |
| Adrenal | | |
| 29.38 | 1.00 | 0.10 |
| 29.81 | 1.00 | 0.20 |
| 29.87 | 1.00 | 0.30 |
| 30.10 | 1.00 | 0.40 |
| 30.11 | 1.00 | 0.50 |
| 30.13 | 1.00 | 0.60 |
| 30.22 | 1.00 | 0.70 |
| 30.55 | 1.00 | 0.80 |
| 30.80 | 1.00 | 0.90 |
| 30.81 | 0.97 | 0.90 |
| 31.51 | 0.97 | 1.00 |
| Multiple myoloma | | |
| 23.61 | 1.00 | 0.00 |
| 23.76 | 1.00 | 0.20 |
| 24.18 | 1.00 | 0.40 |
| 24.34 | 1.00 | 0.60 |
| 24.40 | 0.98 | 0.60 |
| 24.47 | 0.98 | 0.80 |
| 24.50 | 0.95 | 0.80 |
| 25.36 | 0.95 | 1.00 |
| Colon | | |
| 190.00 | 0.96 | 0.93 |
| 250.00 | 0.83 | 0.96 |
| 260.00 | 0.80 | 0.98 |
| 300.00 | 0.65 | 0.98 |
| 350.00 | 0.46 | 0.99 |
| 400.00 | 0.29 | 0.98 |
| 450.00 | 0.22 | 1.00 |
| 500.00 | 0.15 | 1.00 |
| Melanoma | | |
| 6.18 | 1.00 | 0.00 |
| 7.09 | 1.00 | 0.06 |
| 7.16 | 1.00 | 0.13 |
| 7.19 | 1.00 | 0.19 |
| 7.69 | 1.00 | 0.25 |
| 7.82 | 1.00 | 0.31 |
| 7.99 | 1.00 | 0.38 |
| 8.20 | 1.00 | 0.44 |
| 8.33 | 1.00 | 0.50 |
| 8.66 | 0.98 | 0.50 |
| 8.80 | 0.98 | 0.56 |
| 8.90 | 0.98 | 0.63 |
| 9.29 | 0.98 | 0.69 |
| 9.31 | 0.98 | 0.75 |
| 9.93 | 0.98 | 0.81 |
| 10.76 | 0.98 | 0.88 |
| 11.24 | 0.96 | 0.88 |
| 11.25 | 0.96 | 0.94 |

TABLE 8-continued

ROC curve data for CTA signatures

| Cut-off | Sen. | Spec. |
|---|---|---|
| 12.06 | 0.93 | 0.94 |
| 12.80 | 0.91 | 0.94 |
| 14.40 | 0.89 | 0.94 |
| 14.89 | 0.87 | 0.94 |
| 15.45 | 0.85 | 0.94 |
| 15.61 | 0.83 | 0.94 |
| 15.63 | 0.80 | 0.94 |
| 15.65 | 0.78 | 0.94 |
| 16.02 | 0.76 | 0.94 |
| 16.27 | 0.74 | 0.94 |
| 16.31 | 0.72 | 0.94 |
| 16.48 | 0.70 | 0.94 |
| 16.52 | 0.67 | 0.94 |
| 16.54 | 0.65 | 0.94 |
| 16.55 | 0.63 | 0.94 |
| 16.59 | 0.61 | 0.94 |
| 16.67 | 0.59 | 0.94 |
| 16.69 | 0.57 | 0.94 |
| 16.78 | 0.54 | 0.94 |
| 16.92 | 0.52 | 0.94 |
| 16.94 | 0.50 | 0.94 |
| 17.05 | 0.48 | 0.94 |
| 17.17 | 0.46 | 0.94 |
| 17.29 | 0.43 | 0.94 |
| 17.36 | 0.41 | 0.94 |
| 17.51 | 0.39 | 0.94 |
| 17.57 | 0.37 | 0.94 |
| 17.63 | 0.35 | 0.94 |
| 17.81 | 0.33 | 0.94 |
| 17.95 | 0.33 | 1.00 |
| Prostate | | |
| 2.27 | 1.00 | 0.00 |
| 2.27 | 1.00 | 0.07 |
| 2.27 | 1.00 | 0.14 |
| 2.27 | 1.00 | 0.21 |
| 2.28 | 1.00 | 0.29 |
| 2.28 | 1.00 | 0.36 |
| 2.29 | 1.00 | 0.43 |
| 2.29 | 1.00 | 0.50 |
| 2.30 | 0.97 | 0.50 |
| 2.30 | 0.97 | 0.57 |
| 2.30 | 0.97 | 0.64 |
| 2.30 | 0.94 | 0.64 |
| 2.30 | 0.92 | 0.64 |
| 2.31 | 0.92 | 0.71 |
| 2.31 | 0.89 | 0.71 |
| 2.31 | 0.86 | 0.71 |
| 2.31 | 0.83 | 0.71 |
| 2.31 | 0.81 | 0.71 |
| 2.31 | 0.78 | 0.71 |
| 2.31 | 0.78 | 0.79 |
| 2.32 | 0.78 | 0.86 |
| 2.32 | 0.75 | 0.86 |
| 2.34 | 0.75 | 0.93 |
| 2.35 | 0.72 | 0.93 |
| 2.35 | 0.69 | 0.93 |
| 2.45 | 0.67 | 0.93 |
| 2.50 | 0.64 | 0.93 |
| 3.23 | 0.61 | 0.93 |
| 3.38 | 0.58 | 0.93 |
| 3.65 | 0.56 | 0.93 |
| 3.67 | 0.53 | 0.93 |
| 4.16 | 0.50 | 0.93 |
| 5.11 | 0.47 | 0.93 |
| 5.52 | 0.44 | 0.93 |
| 5.62 | 0.42 | 0.93 |
| 5.72 | 0.39 | 0.93 |
| 6.00 | 0.36 | 0.93 |
| 6.16 | 0.33 | 0.93 |
| 6.24 | 0.31 | 0.93 |
| 6.57 | 0.28 | 0.93 |
| 6.63 | 0.28 | 1.00 |
| Prostate 2 | | |
| 17.80 | 1.00 | 0.07 |
| 17.93 | 1.00 | 0.14 |
| 18.31 | 1.00 | 0.21 |
| 18.41 | 1.00 | 0.29 |
| 18.47 | 1.00 | 0.36 |
| 18.66 | 1.00 | 0.43 |
| 18.71 | 1.00 | 0.50 |
| 18.77 | 1.00 | 0.57 |
| 18.79 | 1.00 | 0.64 |
| 19.12 | 1.00 | 0.71 |
| 19.35 | 0.97 | 0.71 |
| 19.45 | 0.97 | 0.79 |
| 19.65 | 0.97 | 0.86 |
| 19.94 | 0.94 | 0.86 |
| 20.04 | 0.92 | 0.86 |
| 20.29 | 0.89 | 0.86 |
| 20.54 | 0.89 | 0.93 |
| 20.59 | 0.86 | 0.93 |
| 21.20 | 0.83 | 0.93 |
| 21.33 | 0.81 | 0.93 |
| 21.33 | 0.78 | 0.93 |
| 21.39 | 0.75 | 0.93 |
| 21.48 | 0.72 | 0.93 |
| 21.68 | 0.69 | 0.93 |
| 21.80 | 0.67 | 0.93 |
| 21.81 | 0.64 | 0.93 |
| 21.90 | 0.61 | 0.93 |
| 21.92 | 0.58 | 0.93 |
| 22.06 | 0.56 | 0.93 |
| 22.12 | 0.53 | 0.93 |
| 22.33 | 0.50 | 0.93 |
| 22.41 | 0.47 | 0.93 |
| 22.53 | 0.44 | 0.93 |
| 22.70 | 0.42 | 0.93 |
| 22.80 | 0.39 | 0.93 |
| 22.81 | 0.36 | 0.93 |
| 23.19 | 0.36 | 1.00 |
| Glioblastoma | | |
| 102.05 | 1.00 | 0.00 |
| 154.20 | 1.00 | 0.04 |
| 156.90 | 1.00 | 0.08 |
| 163.90 | 1.00 | 0.13 |
| 172.90 | 0.98 | 0.13 |
| 173.15 | 0.98 | 0.17 |
| 174.95 | 0.98 | 0.21 |
| 180.75 | 0.98 | 0.25 |
| 181.15 | 0.98 | 0.29 |
| 198.20 | 0.98 | 0.33 |
| 199.95 | 0.98 | 0.38 |
| 209.80 | 0.96 | 0.38 |
| 218.50 | 0.94 | 0.38 |
| 226.15 | 0.94 | 0.42 |
| 243.05 | 0.94 | 0.46 |
| 247.65 | 0.94 | 0.50 |
| 323.60 | 0.94 | 0.54 |
| 352.35 | 0.92 | 0.54 |
| 365.40 | 0.92 | 0.58 |
| 372.75 | 0.90 | 0.58 |
| 447.45 | 0.88 | 0.58 |
| 462.20 | 0.88 | 0.63 |
| 502.90 | 0.86 | 0.63 |
| 550.90 | 0.84 | 0.63 |
| 578.05 | 0.82 | 0.63 |
| 598.85 | 0.82 | 0.67 |
| 633.20 | 0.82 | 0.71 |
| 638.50 | 0.80 | 0.71 |
| 647.20 | 0.78 | 0.71 |
| 652.60 | 0.76 | 0.71 |
| 654.15 | 0.74 | 0.71 |
| 655.05 | 0.72 | 0.71 |
| 672.80 | 0.72 | 0.75 |
| 704.65 | 0.70 | 0.75 |
| 776.25 | 0.68 | 0.75 |

TABLE 8-continued

ROC curve data for CTA signatures

| Cut-off | Sen. | Spec. |
|---|---|---|
| 778.20 | 0.66 | 0.75 |
| 848.30 | 0.64 | 0.75 |
| 872.75 | 0.62 | 0.75 |
| 889.40 | 0.60 | 0.75 |
| 889.40 | 0.58 | 0.75 |
| 921.40 | 0.56 | 0.75 |
| 935.85 | 0.54 | 0.75 |
| 938.00 | 0.54 | 0.79 |
| 963.75 | 0.52 | 0.79 |
| 997.90 | 0.50 | 0.79 |
| 1015.75 | 0.48 | 0.79 |
| 1119.45 | 0.48 | 0.83 |
| 1241.35 | 0.46 | 0.83 |
| 1312.15 | 0.44 | 0.83 |
| 1315.30 | 0.42 | 0.83 |
| 1326.65 | 0.40 | 0.83 |
| 1426.25 | 0.38 | 0.83 |
| 1436.65 | 0.36 | 0.83 |
| 1630.70 | 0.36 | 0.88 |
| 1666.30 | 0.36 | 0.92 |
| 1747.00 | 0.34 | 0.92 |
| 1766.85 | 0.34 | 0.96 |
| 1864.65 | 0.34 | 1.00 |

Example 3

A CTA Signature for Detecting Breast Cancer 353 breast cancer samples and 2 samples from healthy individuals were used for the volcano analysis described above. Table 9 presents the genes that demonstrated at least a 2-fold increase in expression with a P value threshold of 0.05.

TABLE 9

CTA genes demonstrating increased expression in breast cancer samples.

| Gene | P-Value | FC |
|---|---|---|
| RBM46 | 1.48E−03 | 17.98 |
| CT47A1/2/3/4/5/6/7/8/9/10/11 | 4.06E−03 | 13.25 |
| MAGEB3 | 7.79E−03 | 6.72 |
| LOC653786/OTOA | 9.84E−03 | 3.44 |
| DMRT1 | 1.37E−02 | 5.68 |
| LDHC | 2.03E−02 | 3.15 |
| CCDC83 | 2.44E−02 | 12.89 |
| ANKRD45 | 2.52E−02 | 4.94 |
| DDX53 | 2.53E−02 | 9.67 |
| BAGE | 2.53E−02 | 2.33 |
| TDRD1 | 2.60E−02 | 5.45 |
| CEP55 | 2.63E−02 | 3.20 |
| PRM1 | 2.72E−02 | 3.86 |
| SSX2/2B | 3.17E−02 | 5.48 |
| SEMG1 | 3.32E−02 | 8.51 |
| TPTE | 4.17E−02 | 3.90 |
| SPAG1 | 4.20E−02 | 2.43 |

Figure 6A:
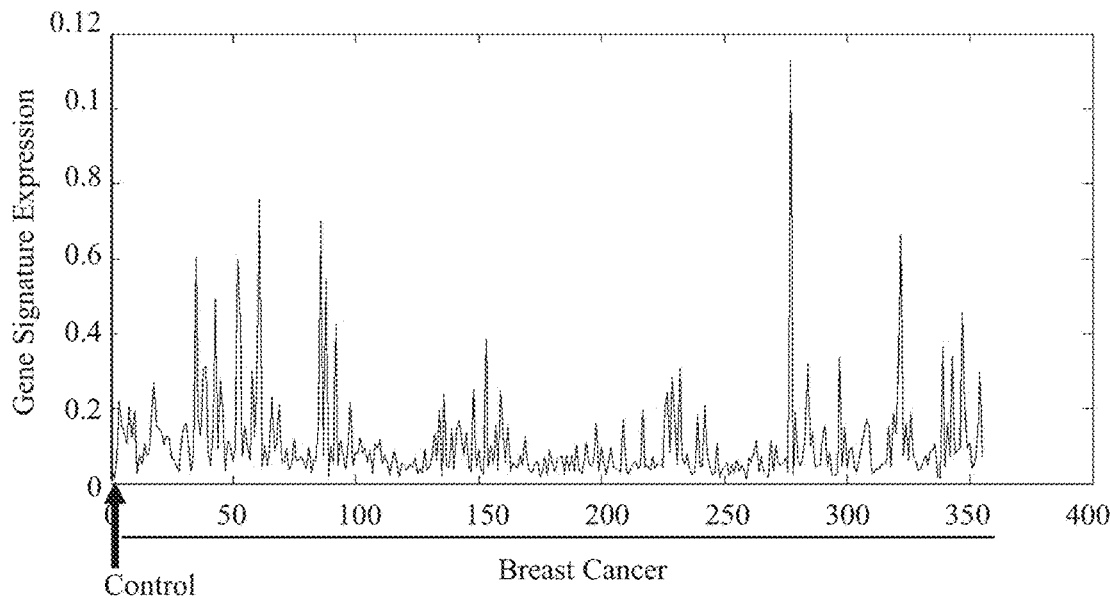
FIGS. 6A-6B.
Figure 6B:
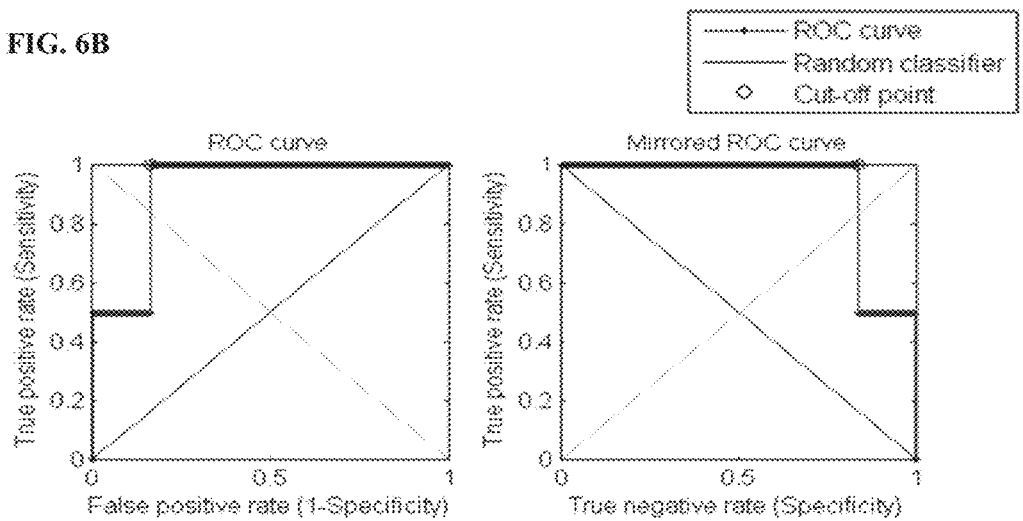

Using the ranking method, it was found that the sum of fold increases of the four highest ranking genes (RBM46, CT47A1/2/3/4/5/6/7/8/9/10/11, PBK, and DDX53) when compared to control levels can be used to differentiate between samples taken from breast cancer patients and samples taken from non-cancerous individuals (FIG. 6A). A ROC curve analysis using the sum of fold increases of these genes, was performed. The cut-off point, for best sensitivity and specificity of the ROC curve analysis, resulted in a sensitivity of 100.0% with a 95% confidence interval of 100.0% and false negative proportion of 0.0%, a specificity of 83.6% with a 95% confidence interval of 79.7%-87.4% and a false positive proportion of 16.4% (FIG. 6B). Further, the area under the curve of the ROC analysis was found to be 0.91643, indicating the high accuracy of this test (FIG. 6B).

Example 4

A CTA Signature for Detecting Kidney Cancer 281 kidney cancer samples and 9 samples from healthy individuals were used for the volcano analysis described above. Table 10 presents the genes that demonstrated at least a 2-fold increase in expression with a P value threshold of 0.05. Table 5 presents, inter alia, clustering data for kidney cancer genes.

TABLE 10

CTA genes demonstrating increased expression in kidney cancer samples.

| Gene | P-Value | FC |
|---|---|---|
| SPAG4 | 1.39E−07 | 7.20 |
| LOC653786/OTOA | 6.57E−06 | 4.86 |
| CEP55 | 6.79E−06 | 9.19 |
| GAGE1/2A/2B/2C/2D/2E/3/4/5/6/7/8/12F/12G/12I/12J | 6.34E−05 | 5.09 |
| ATAD2 | 4.64E−05 | 3.31 |
| TPTE | 4.43E−05 | 3.55 |
| MAGEA6 | 1.04E−04 | 3.52 |
| MORC1 | 1.27E−04 | 4.67 |
| TTK | 2.12E−04 | 4.12 |
| CTNNA2 | 4.90E−04 | 3.98 |
| PBK | 4.91E−04 | 3.16 |
| RGS22 | 9.69E−04 | 3.55 |
| TMEFF1 | 1.06E−03 | 2.55 |
| ARX | 1.32E−03 | 2.59 |
| MAGEB4 | 1.47E−03 | 2.78 |
| PRAME | 2.12E−03 | 3.15 |
| GAGE2A/2C/4/5/6/7/12C/12D/12E/12F/12G/12GH/12I | 4.51E−03 | 2.39 |
| TEX14 | 7.55E−03 | 2.46 |
| POTED | 8.78E−03 | 2.53 |
| DMRT1 | 8.82E−03 | 3.01 |
| CTCFL | 1.02E−02 | 2.28 |
| GPAT2 | 1.27E−02 | 2.44 |
| GAGE5/7/12F/12G/12I | 1.34E−02 | 2.09 |
| GAGE3 | 1.74E−02 | 2.29 |
| SPANXA1/A2/C | 1.82E−02 | 2.17 |
| DDX43 | 1.97E−02 | 2.00 |
| GAGE1 | 2.55E−02 | 2.42 |

Figure 7A:
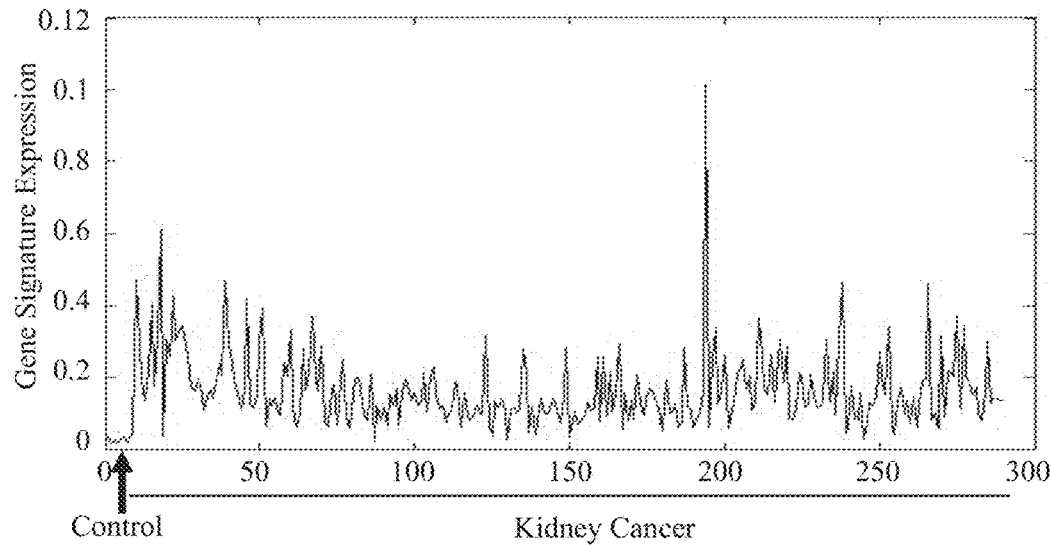
FIGS. 7A-7B.
Figure 7B:
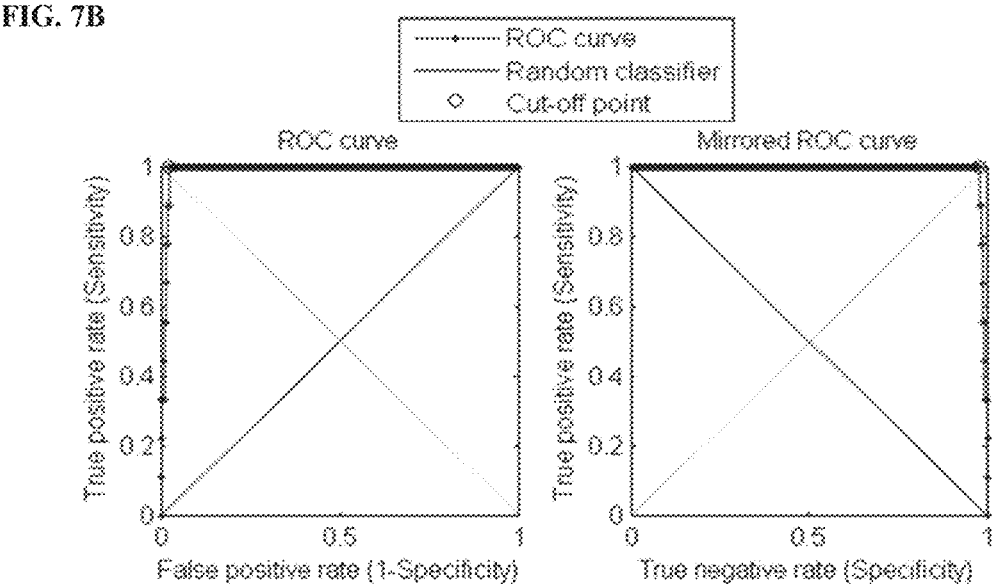

Using the ranking method, it was found that the sum of fold increases of the five highest ranking genes (CEP55, GAGE1/2A/2B/2C/2D/2E/3/4/5/6/7/8/12F/12G/12I/12J, SPAG4, LOC653786/OTOA and CTNNA2) when compared to control levels can be used to differentiate between samples taken from kidney cancer patients and samples taken from non-cancerous individuals (FIG. 7A). A ROC curve analysis was performed as before. The cut-off point, for best sensitivity and specificity of the ROC curve analysis, resulted in a sensitivity of 100.0% with a 95% confidence interval of 100.0% and false negative proportion of 0.0%, and a specificity of 97.9% with a 95% confidence interval of 96.2%-99.6% and a false positive proportion of 2.1% (FIG. 7B). Further, the area under the curve of the ROC curve was found to be 0.99209, indicating the high accuracy of this test (FIG. 7B).

Example 5

A CTA Signature for Detecting Lung Cancer 129 lung cancer samples and 3 samples from healthy individuals were used for the volcano analysis described above. Table 11 presents the genes that demonstrated at least a 2-fold increase in expression with a P value threshold of 0.05. Table 5 presents clustering data for lung cancer genes.

TABLE 11

CTA genes demonstrating increased expression in lung cancer samples.

| Gene | P-Value | FC |
|---|---|---|
| TTK | 1.97E−03 | 7.40 |
| ATAD2 | 2.19E−03 | 3.32 |
| CEP55 | 4.22E−03 | 5.75 |
| PBK | 6.15E−03 | 11.34 |
| MORC1 | 8.35E−03 | 4.47 |
| LDHC | 9.81E−03 | 4.39 |
| BAGE2/3/5/KMT2C | 1.03E−02 | 4.00 |
| PRAME | 2.70E−02 | 10.38 |
| HORMAD1 | 2.84E−02 | 5.86 |
| PASD1 | 3.10E−02 | 2.14 |
| XAGE1B/E | 3.45E−02 | 19.55 |
| MAGEA6 | 3.61E−02 | 19.66 |
| MAGEA2/2B | 3.73E−02 | 27.60 |
| ELOVL4 | 4.12E−02 | 2.43 |
| SPAG4 | 4.33E−02 | 4.12 |
| MAGEA3 | 4.36E−02 | 11.79 |
| IL13RA2 | 4.81E−02 | 10.84 |

Figure 8A:
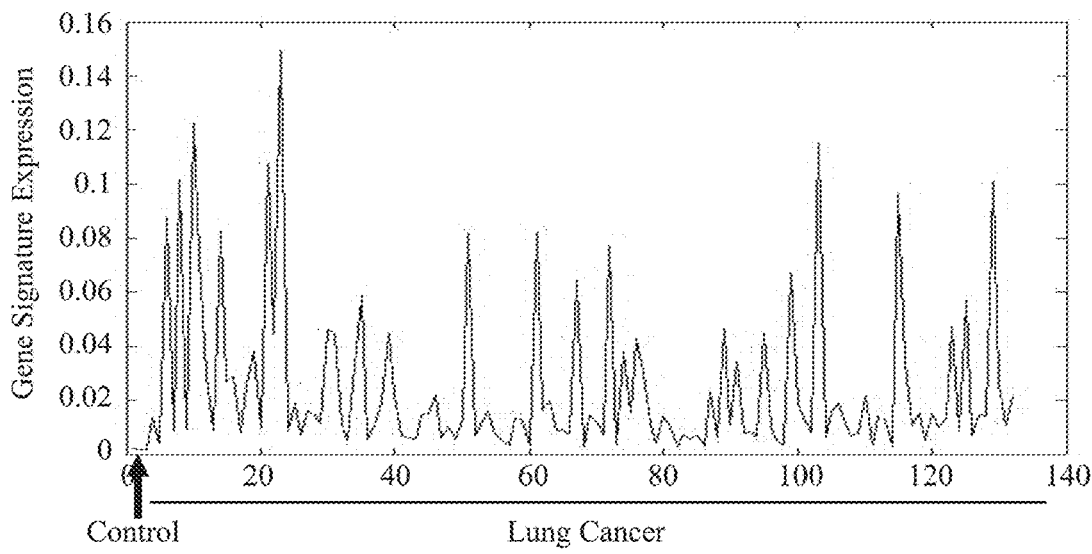
FIGS. 8A-8B.
Figure 8B:
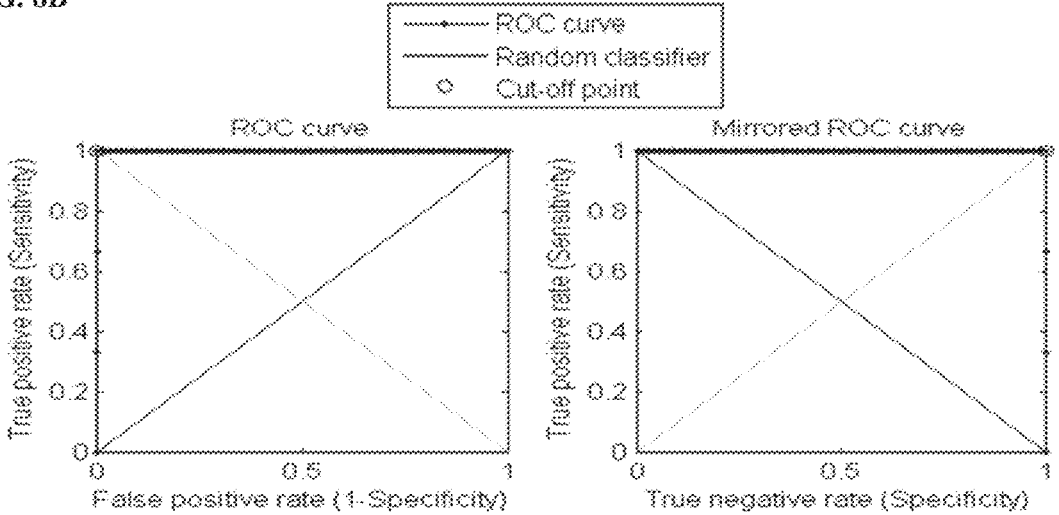

Using the ranking method, it was found that the sum of fold increases of the five highest ranking genes (PBK, MORC1, XAGE1B/E, BAGE2/3/5/KMT2C and IL13RA2) when compared to control levels can be used to differentiate between samples taken from lung cancer patients and samples taken from non-cancerous individuals (FIG. 8A). A ROC curve analysis was performed as before. The cut-off point, for best sensitivity and specificity of the ROC curve analysis, resulted in a sensitivity of 100.0% with a 95% confidence interval of 100.0% and false negative proportion of 0.0%, and a specificity of 100% with a 95% confidence interval of 100% and a false positive proportion of 0% (FIG. 8B). Further, the area under the curve of the ROC curve was found to be 1, indicating the near perfect accuracy of this test (FIG. 8B).

Example 6

A CTA Signature for Detecting Ovarian Cancer 2004 ovarian cancer samples and 5 samples from healthy individuals were used for the volcano analysis described above. Table 12 presents the genes that demonstrated at least a 2-fold increase in expression with a P value threshold of 0.05.

TABLE 12

CTA genes demonstrating increased expression in ovarian cancer samples.

| Gene name | FI | P value |
|---|---|---|
| ZNF165 | 9.51 | 4.36E−05 |
| GAGE1 | 6.24 | 1.75E−04 |
| SPAG1 | 7.20 | 3.17E−04 |
| PRAME | 14.14 | 3.65E−04 |

TABLE 12-continued

CTA genes demonstrating increased expression in ovarian cancer samples.

| Gene name | FI | P value |
|---|---|---|
| TTK | 8.67 | 6.57E−04 |
| LEMD1 | 12.16 | 2.03E−03 |
| SPA17 | 5.15 | 2.06E−03 |
| PBK | 6.69 | 4.54E−03 |
| TMEFF1 | 2.99 | 4.64E−03 |
| CEP55 | 5.75 | 4.77E−03 |
| CTNNA2 | 6.58 | 1.00E−02 |
| SPAG4 | 2.52 | 1.09E−02 |
| CTCFL | 10.32 | 1.37E−02 |
| SPAG17 | 2.01 | 1.57E−02 |
| BAGE | 2.28 | 1.70E−02 |
| ATAD2 | 2.13 | 2.05E−02 |
| PRSS54 | 2.09 | 2.34E−02 |
| GPAT2 | 3.78 | 2.39E−02 |
| CCDC83 | 2.24 | 2.81E−02 |
| MAGEA11 | 6.64 | 2.93E−02 |
| CT45A1/A2/A3/A4/A5/A6 | 32.68 | 3.32E−02 |
| LY6K | 3.42 | 3.40E−02 |
| TSGA10 | 2.22 | 3.47E−02 |
| DSCR8 | 4.11 | 3.50E−02 |
| CTAG1A/CTAG1B | 9.72 | 3.71E−02 |
| SAGE1 | 2.44 | 3.81E−02 |

Figure 9A:
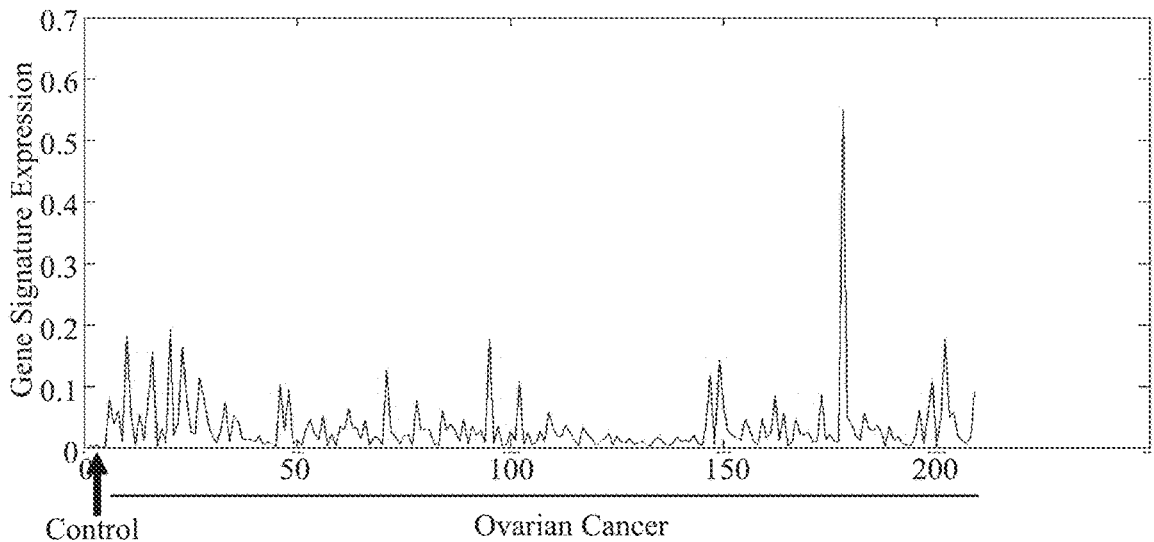
FIGS. 9A-9B.
Figure 9B:
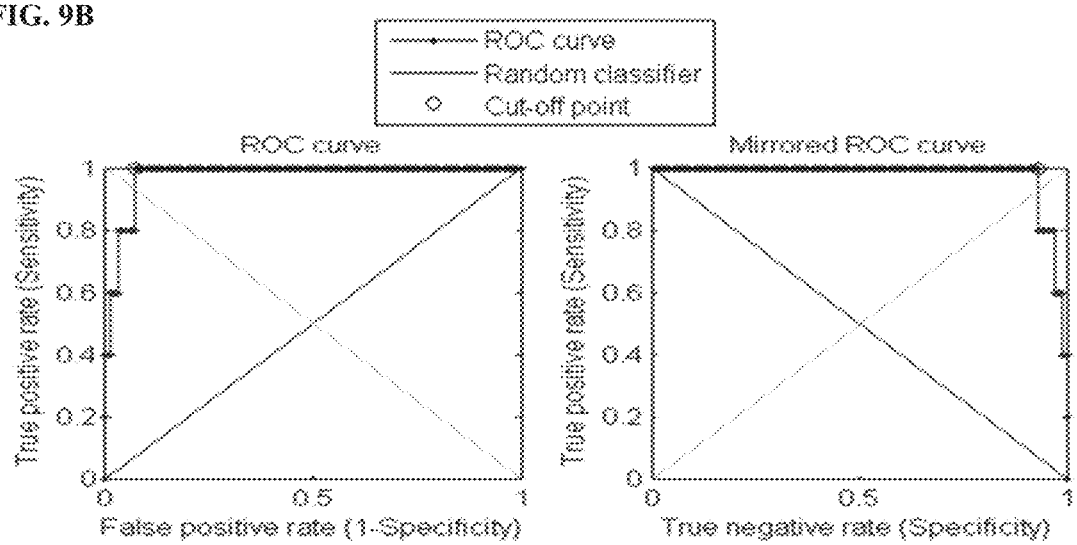

Using the ranking method, it was found that the sum of fold increases of the four highest ranking genes (ZNF165, PRAME, GAGE1 andGAGE5/7/12F/G/I) when compared to control levels can be used to differentiate between samples taken from ovarian cancer patients and samples taken from non-cancerous individuals (FIG. 9A). A ROC curve analysis was performed as before. The cut-off point, for best sensitivity and specificity of the ROC curve analysis, resulted in a sensitivity of 100.0% with a 95% confidence interval of 100.0% and false negative proportion of 0.0%, and a specificity of 93.1% with a 95% confidence interval of 89.7%-96.6% and a false positive proportion of 6.9% (FIG. 9B). Further, the area under the curve of the ROC curve was found to be 0.97843, indicating the high accuracy of this test (FIG. 9B).

Example 7

A CTA Signature for Detecting Adrenal Cancer 33 adrenal cancer samples and 10 samples from healthy individuals were used for the volcano analysis described above. Table 13 presents the genes that demonstrated at least a 2-fold increase in expression with a P value threshold of 0.05. Table 5 presents clustering data for adrenal cancer genes.

TABLE 13

CTA genes demonstrating increased expression in adrenal cancer samples.

| Gene name | FI | P value |
|---|---|---|
| CEP55 | 7.35 | 5.15E−06 |
| TTK | 5.84 | 1.65E−05 |
| PBK | 17.15 | 2.14E−05 |
| ATAD2 | 2.38 | 2.24E−05 |
| ELOVL4 | 5.04 | 3.57E−05 |
| OIP5 | 2.62 | 5.02E−05 |
| FAM133A | 4.12 | 2.43E−03 |
| FATE1 | 32.49 | 6.69E−03 |
| IL13RA2 | 16.14 | 6.76E−03 |
| PRAME | 5.24 | 1.18E−02 |

TABLE 13-continued

CTA genes demonstrating increased expression
in adrenal cancer samples.

| Gene name | FI | P value |
|---|---|---|
| MAGEA6 | 15.89 | 1.23E−02 |
| CTNNA2 | 3.37 | 1.27E−02 |
| MAGEA3 | 13.65 | 1.35E−02 |
| PLAC1 | 5.30 | 1.73E−02 |
| MAGEA12 | 7.95 | 1.78E−02 |

Figure 10A:
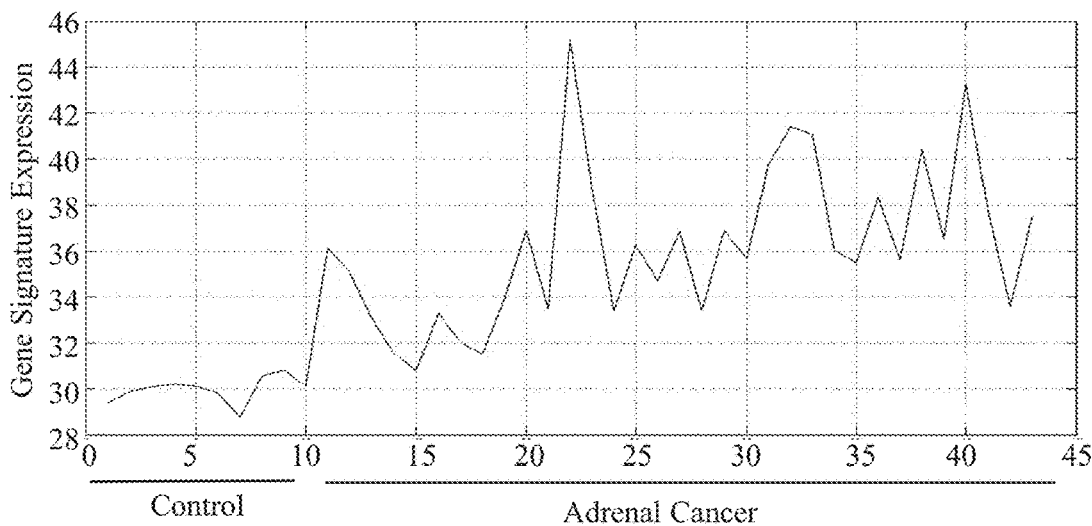
FIGS. 10A-10C: 10A is a graph showing the sum expression of: MAGEA12, SPAG4 and ELOVL4 in 10 non-cancerous samples followed by 33 adrenal cancer samples.
Figure 10B:
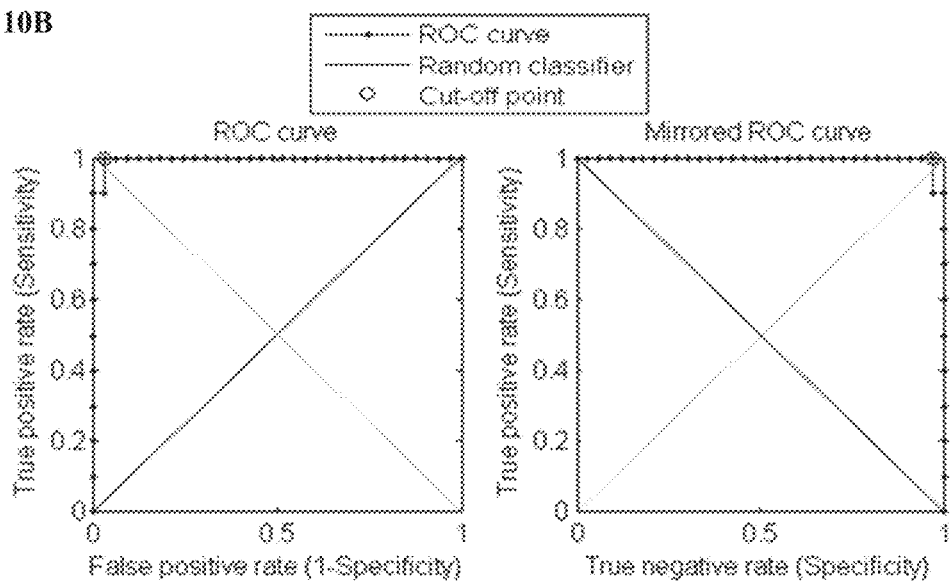
Figure 10C:
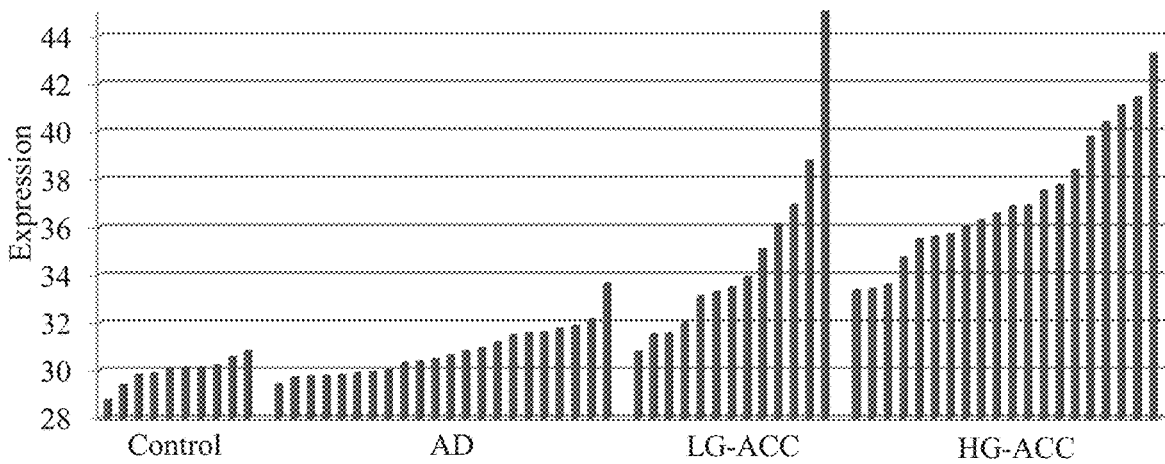

Using the ranking method, it was found that the sum of fold increases of the four highest ranking genes (PBK, MAGEA12, SPAG4 and ELOVL4) when compared to control levels can be used to differentiate between samples taken from adrenal cancer patients and samples taken from non-cancerous individuals (FIG. 10A). A ROC curve analysis was performed as before, data from which can be seen in Table 8 and FIG. 10B. Further, the sum of fold increases demonstrated a correlation with the severity and stage of the adrenal cancer (FIG. 10C).

Example 8

A CTA Signature for Detecting Colon Cancer 186 colon cancer samples and 10 samples from healthy individuals were used for the volcano analysis described above. Table 14 presents the genes that demonstrated at least a 2-fold increase in expression with a P value threshold of 0.05. Table 5 presents clustering data for colon cancer genes.

TABLE 14

CTA genes demonstrating increased
expression in colon cancer samples.

| Gene name | FI | P value |
|---|---|---|
| ODF2 | 2.39 | 2.87E−05 |
| MAGEA11 | 2.88 | 3.15E−05 |
| MAGEA3 | 8.81 | 7.01E−04 |
| CEP55 | 2.35 | 7.64E−04 |
| MAGEA6 | 8.25 | 1.04E−03 |
| MAGEA12 | 2.17 | 1.38E−03 |
| MAGEA1 | 2.06 | 3.73E−03 |
| IL13RA2 | 2.52 | 5.22E−03 |

Figure 11:
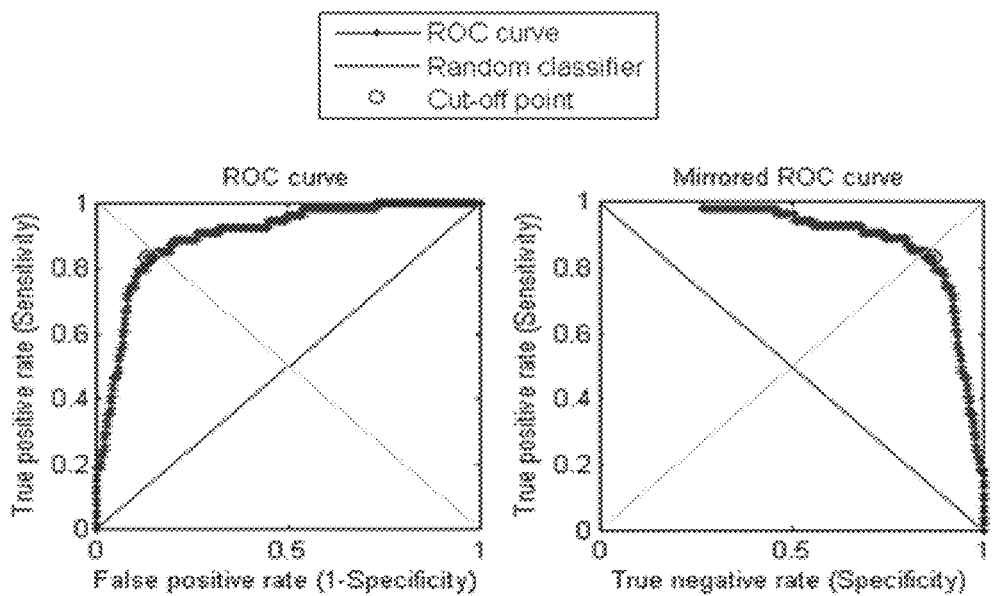
FIG. 11 is a ROC curve based on the sum folds increase in expression of the CTA genes.

Using all eight CTA genes found to differentiate between colon cancer patients and non-cancerous individuals, resulted in a sensitivity of 83.3% with a 95% confidence interval of 73.4%-93.3% and false negative proportion of 16.7%, and a specificity of 87.1% with a 95% confidence interval of 82.3%-91.9% and a false positive proportion of 12.9% (FIG. 11). The area under the curve of the ROC curve was found to be 0.90382, indicating the high accuracy of this test (FIG. 11).

Figure 12:
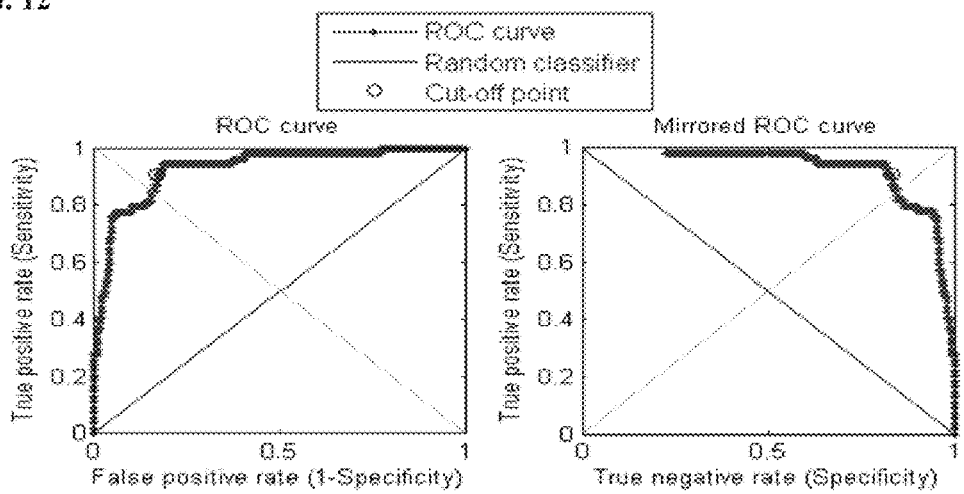
FIG. 12 is a ROC curve based on the sum folds increase in expression of the CTA genes.

Using the ranking method, it was found that the sum of fold increases of the highest-ranking genes (MAGEA11, ODF2, IL13RA2, MAGEA6, DDX43, CEP55, MAGEA1, MAGEB3, SPANXB1, BAGE and TSGA10) when compared to control levels can be used to differentiate between samples taken from colon cancer patients and samples taken from non-cancerous individuals. A ROC curve analysis was performed as before, data from which can be seen in Table 8. The cut-off point, for best sensitivity and specificity of the ROC curve analysis, resulted in a sensitivity of 90.7% with a 95% confidence interval of 83%-98.5% and false negative proportion of 9.3%, and a specificity of 83.3% with a 95% confidence interval of 78%-88.7% and a false positive proportion of 16.7% (FIG. 12). The area under the curve of the ROC curve was found to be 0.93260, indicating the high accuracy of this test (FIG. 12).

Figure 13:
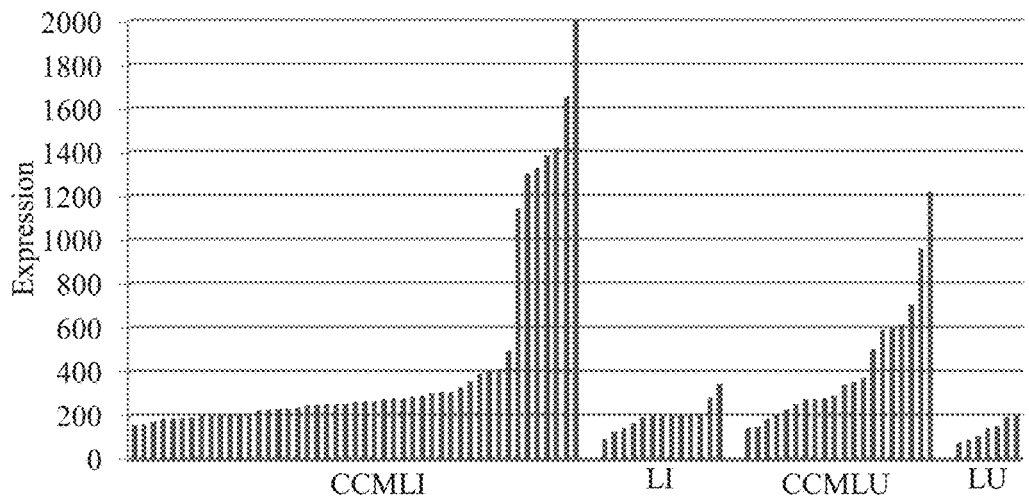
FIG. 13 is a bar graph showing the sum expression of 11 signature genes in colon carcinoma metastatic to the liver (CCMLI) and lungs (CCMLU) and their neighboring healthy liver (LI) and lung (LU) cells.

As shown in FIG. 13, increase in the sum expression value of these CTA genes may be used to distinguish between metastatic colon cancer cells and neighboring healthy lung and liver cells.

A ROC curve analysis was performed as before to differentiate between metastatic colon cancer cells and neighboring healthy lung cells, was performed. The cut-off point, for best sensitivity and specificity of the ROC curve analysis, resulted in a sensitivity of 100% with a 95% confidence interval of 100% and false negative proportion of 0%, and a specificity of 85%. The area under the curve of the ROC curve was found to be 0.94286, indicating the high accuracy of this test.

A ROC curve analysis was performed as before to differentiate between metastatic colon cancer and neighboring healthy liver cells, was performed. The cut-off point, for best sensitivity and specificity of the ROC curve analysis, resulted in a sensitivity of 84.6% with a 95% confidence interval of 65%-100% and false negative proportion of 15.4%, and a specificity of 76.6% with a 95% confidence interval of 64.5%-88.7% and a false positive proportion of 23.4%. The area under the curve of the ROC curve was found to be 0.94777, indicating the high accuracy of this test.

Example 9

A CTA Signature for Detecting Multiple Myeloma 41 multiple myeloma cancer samples and 5 samples from healthy individuals were used for volcano analysis as described above. Table 15 presents the genes that demonstrated at least a 2-fold increase in expression with a P value threshold of 0.05. Table 5 presents clustering data for multiple myeloma cancer genes.

TABLE 15

CTA genes demonstrating increased expression
in multiple myeloma samples.

| Gene name | FI | P value |
|---|---|---|
| MAGEC1 | 1.230536 | 0.000141 |
| FAM133A | 1.518777 | 0.000165 |
| MORC1 | 1.328271 | 0.000196 |

Figure 14A:
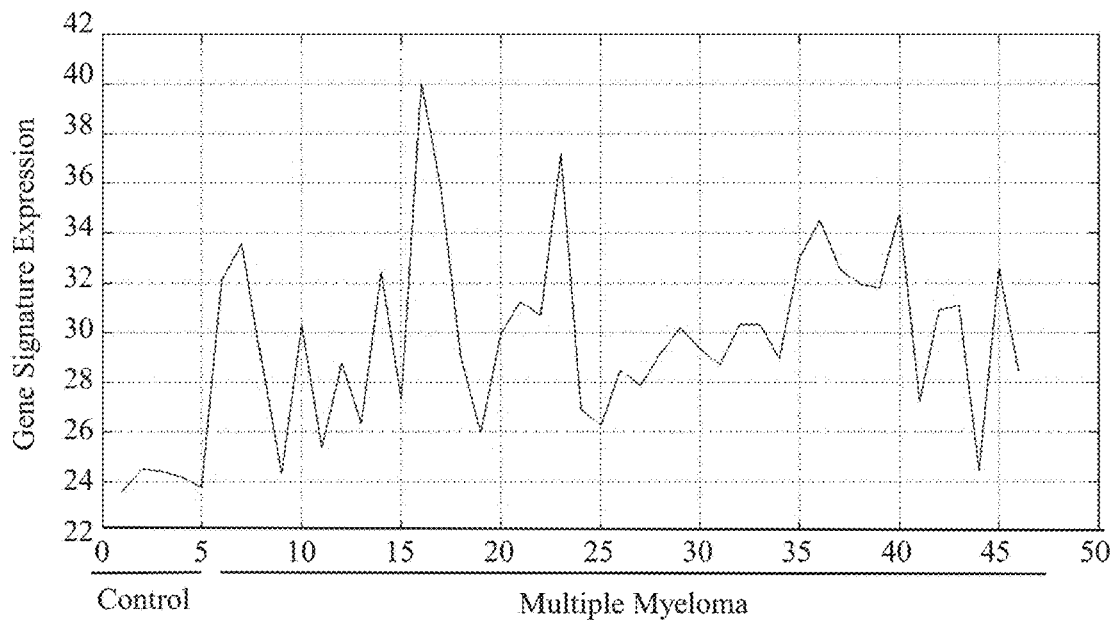
FIGS. 14A-14C.
Figure 14B:
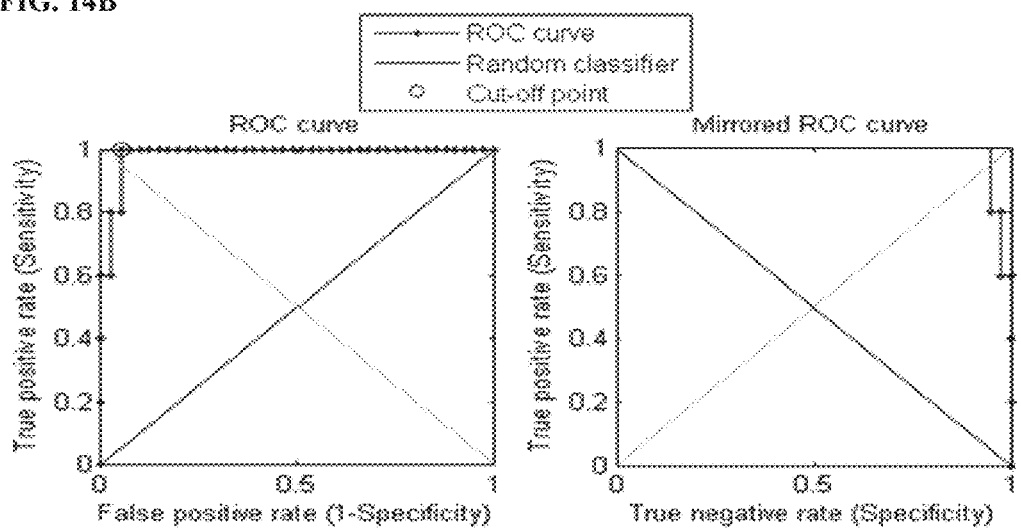

Using the ranking method, it was found that the sum of fold increases of the seven highest ranking genes (FAM133A, MORC1, TEX14, ANKRD45, MAGEB2, MAGEC1 and ELOVL4) when compared to control levels can be used to differentiate between samples taken from multiple myeloma cancer patients and samples taken from non-cancerous individuals (FIG. 14). A ROC curve analysis was performed as before data from which can be found in Table 8. The cut-off point, for best sensitivity and specificity of the ROC curve analysis, resulted in a sensitivity of 100.0% with a 95% confidence interval of 100.0% and false negative proportion of 0.0%, and a specificity of 95.1% with a 95% confidence interval of 88.5%-100% and a false positive proportion of 4.9% (Table 30 and FIG. 14B). The area under the curve of the ROC curve was found to be 0.98537, indicating the high accuracy of this test (FIG. 14B).

Figure 14C:
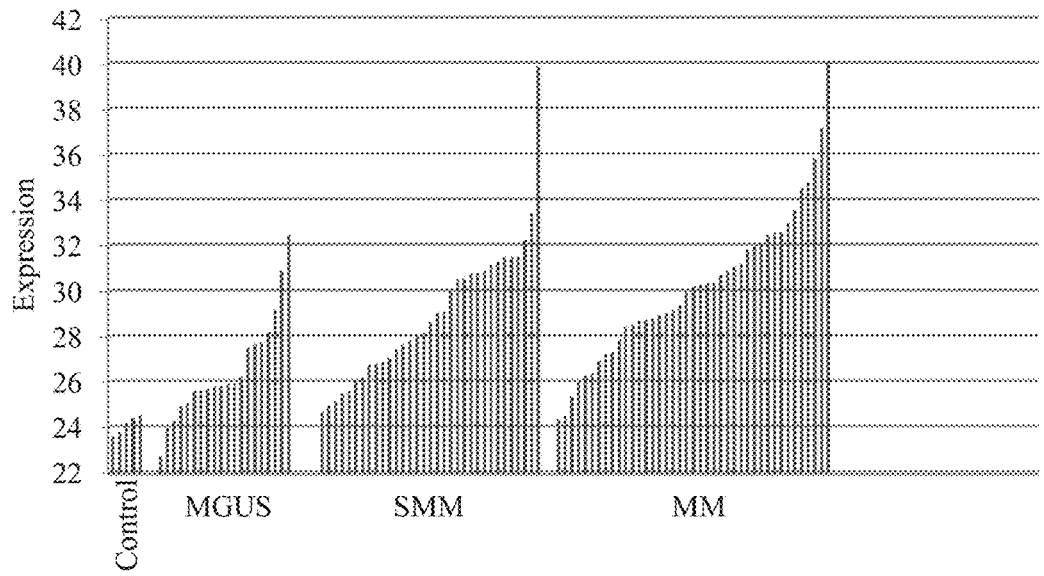

Further, the sum of gene expression had a demonstrated correlation with the severity and stage of the multiple myeloma (FIG. 14C).

Example 10

A CTA Signature for Detecting Melanoma 46 melanoma cancer samples and 16 samples from healthy individuals were used for the volcano analysis described above. Table 16 presents the genes that demonstrated at least a 2-fold increase in expression with a P value threshold of 0.05. Table 5 presents clustering data for melanoma cancer genes.

TABLE 16

CTA genes demonstrating increased expression in melanoma samples.

| Gene name | FI | P value |
|---|---|---|
| MAGEA2/2B | 5.78 | 2.23E−06 |
| TMEFF1 | 2.20 | 2.45E−06 |
| IGSF11 | 10.26 | 3.95E−06 |
| MAGEA3 | 11.01 | 1.14E−05 |
| SSX1 | 5.38 | 1.22E−05 |
| MAGEA6 | 10.70 | 3.23E−05 |
| MAGEA12 | 6.92 | 5.16E−05 |
| CTNNA2 | 5.12 | 1.38E−04 |
| PBK | 2.73 | 1.67E−04 |
| ANKRD45 | 2.17 | 1.94E−04 |
| SSX4/4B | 3.74 | 1.96E−04 |
| MAGEC1 | 3.98 | 3.69E−04 |
| SSX2/2B | 2.78 | 4.85E−04 |
| MAGEA1 | 2.06 | 5.74E−04 |
| MAGEC2 | 5.05 | 7.66E−04 |
| DSCR8 | 4.67 | 1.08E−03 |
| PRAME | 40.82 | 1.16E−03 |
| TTK | 2.13 | 2.83E−03 |
| CTAG1A/B | 2.33 | 7.35E−03 |
| TPTE | 2.69 | 1.16E−02 |
| XAGE1B/E | 2.20 | 1.27E−02 |
| IL13RA2 | 2.66 | 1.34E−02 |

Figure 15A:
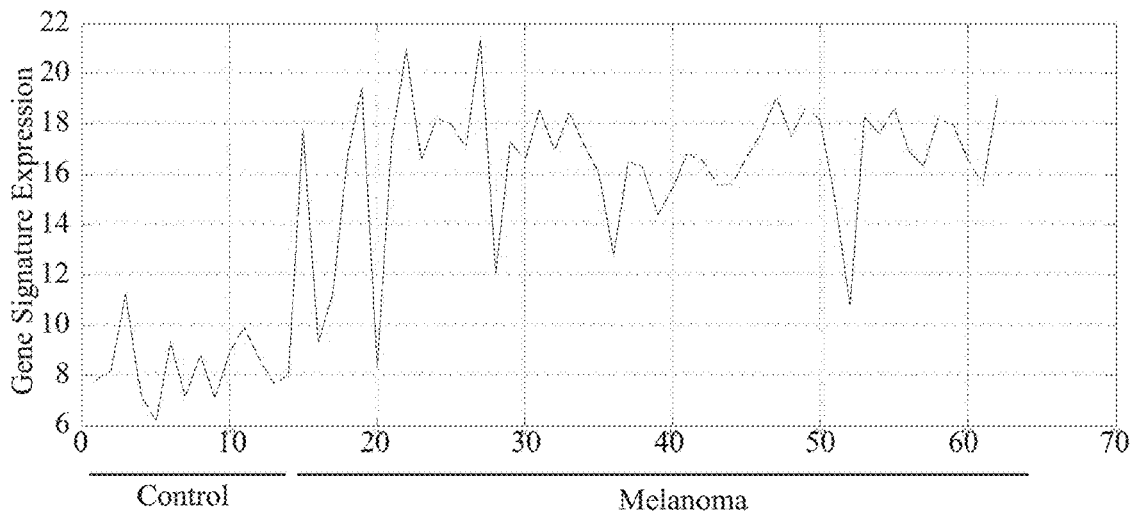
FIGS. 15A-15C.
Figure 15B:
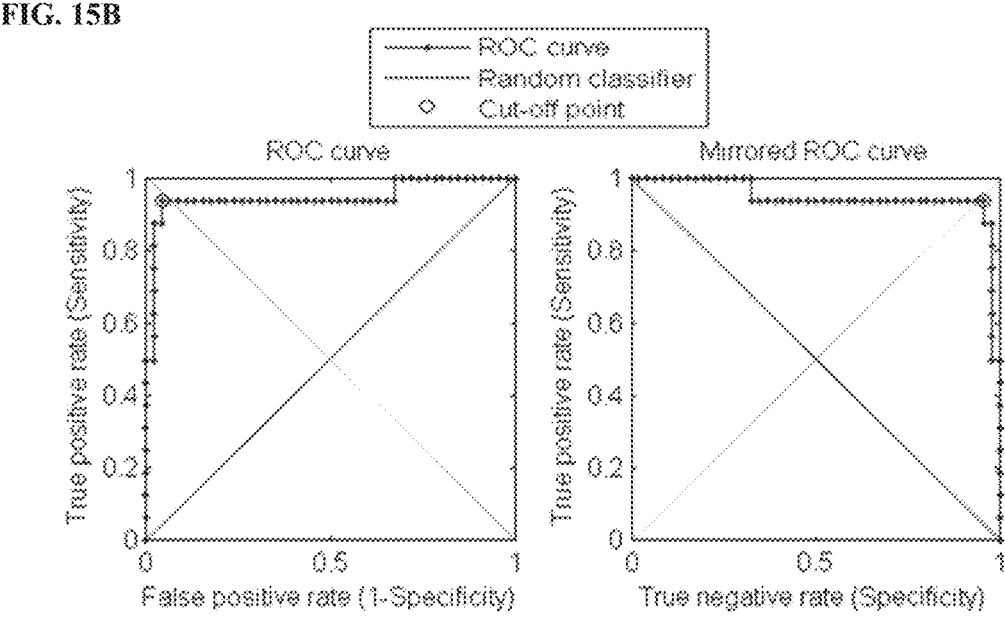

Using the ranking method, it was found that the sum of fold increases of two genes (PRAME and CTNNA2) when compared to control levels can be used to differentiate between samples taken from melanoma cancer patients and samples taken from non-cancerous individuals (FIG. 15A). A ROC curve analysis was performed as before, data from which can be seen in Table 8 and FIG. 15B. The area under the curve of the ROC curve was found to be 0.94701, indicating the high accuracy of this test (FIG. 15B).

Figure 15C:
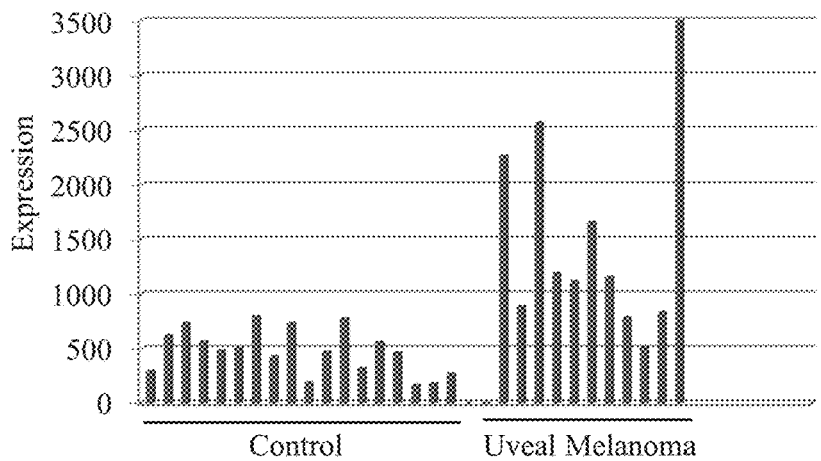

In uveal melanoma, the sum of the expression of four genes (DDX43, SSX1, ATAD2 and CEP55) when compared to control levels can be used to differentiate between samples taken from uveal melanoma cancer patients and samples taken from non-cancerous individuals (FIG. 15C).

Example 11

A CTA Signature for Detecting Prostate Cancer 36 prostate cancer samples and 14 samples from healthy individuals were used for the volcano analysis described above. The gene TDRD1 was the only gene that demonstrated at least a 2-fold increase in expression with a P value threshold of 0.05.

Figure 16:
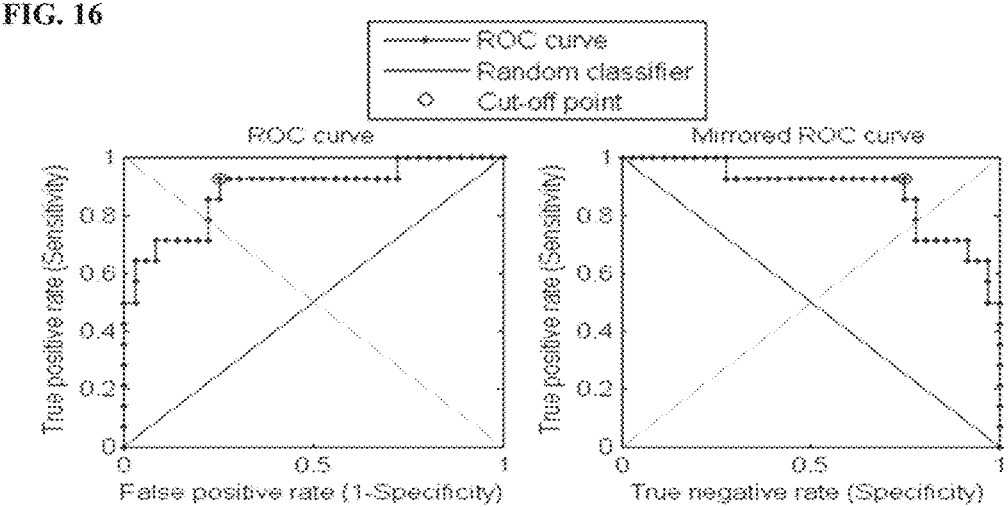
FIG. 16 is a ROC curve based on the fold increase in expression of the TDRD1.

A ROC curve analysis was performed as before, data from which can be seen in Table 8 and FIG. 16. The area under the curve of the ROC curve was found to be 0.88889, indicating the high accuracy of this test (FIG. 16).

Using the ranking method, it was found that the sum of fold increases of the four highest ranking genes (TDRD1, POTED, DCAF12 and TSGA10) when compared to control levels can be used to differentiate between samples taken from prostate cancer patients and samples taken from non-cancerous individuals (FIG. 17A). A ROC curve analysis was performed as before, data from which can be seen in Table 8 and FIG. 17B. The area under the curve of the ROC curve was found to be 0.94246, indicating the high accuracy of this test (FIG. 17B).

Example 12

A CTA Signature for Detecting Glioblastoma

Figure 18B:
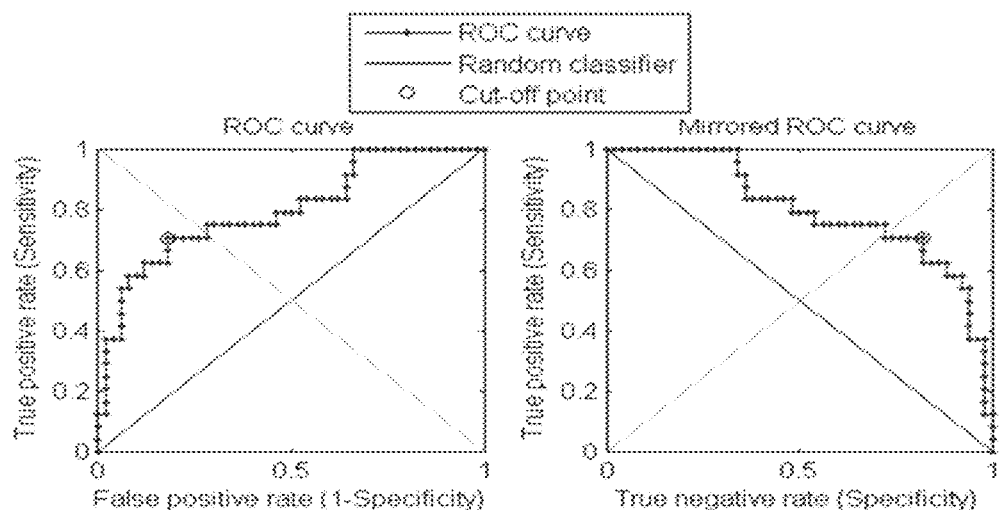
Figure 18C:
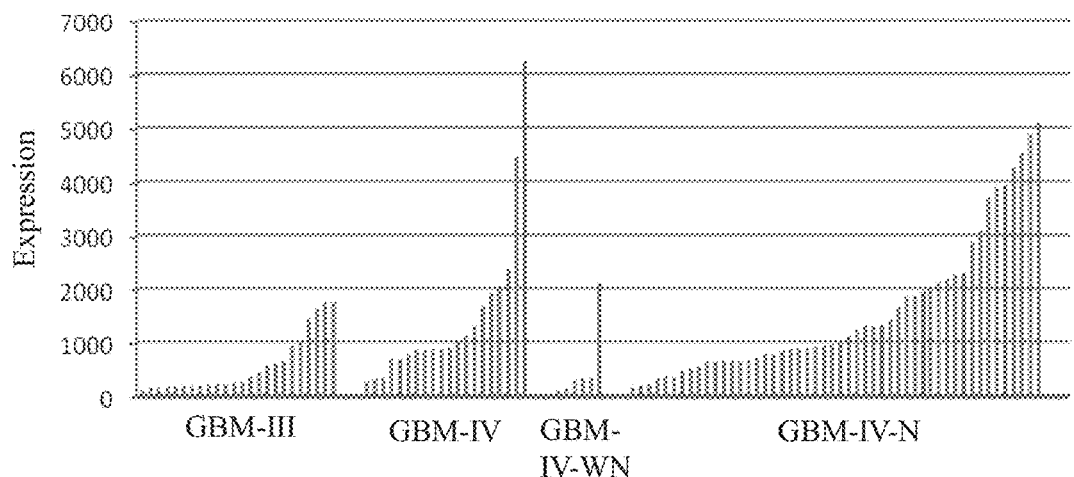

Using the ranking method, it was found that the sum of fold increases of the seven highest ranking genes (IL13RA2, ZNF165, CEP55, CTAG2, SPAG4, MORC1 and SPAG8) when compared to control levels can be used to differentiate between samples taken from glioblastoma cancer patients and samples taken from non-cancerous individuals (FIG. 18A). A ROC curve analysis was performed as before, data from which can be seen in Table 8 and FIG. 18B. The area under the curve of the ROC curve was found to be 0.80083, indicating the high accuracy of this test (FIG. 18B). Further, the sum of the fold increases, demonstrated a correlation with the severity and stage of the glioblastoma (FIG. 18C).

Example 13

A CTA Signature for Detecting Pancreas Cancer and Circulating Tumor Cells (CTC) of Pancreas in Blood Statistical analyses were conducted in order to identify CTA genes exhibiting increased expression in pancreases cancer samples as compared to non-cancerous samples taken from healthy individuals. The CTA genes: CEP55, PBK, TTK and OIP5, were found to be significantly increased in pancreas tumor cells as compared to non-cancerous samples.

It was found that the sum of the fold increases over a control of CEP55, PBK, TTK and OIP5 was significant in pancreas tumor cells and not in non-cancerous samples, and thus can be used to distinguish between them (Table 37).

TABLE 37

CTA genes expression in normal and pancreas tumors

| Tissue type | Expression of CEP55 | Expression of PBK | Expression of TTK | Expression of OIP5 | sum Expression |
|---|---|---|---|---|---|
| Normal 1 | 5.19882 | 5.13765 | 4.60199 | 4.82551 | 19.76397 |
| Normal 2 | 6.76366 | 6.57255 | 5.94084 | 5.85294 | 25.12999 |
| Normal 3 | 5.66895 | 5.25197 | 4.24975 | 4.89307 | 20.06374 |
| Normal 4 | 6.77359 | 5.83651 | 5.11862 | 5.56327 | 23.29199 |
| Normal 5 | 4.29182 | 5.32631 | 3.62687 | 4.20061 | 17.44561 |
| Normal 6 | 6.24269 | 5.46714 | 5.19147 | 5.27818 | 22.17948 |
| Pancreas tumor 1 | 7.61108 | 6.98011 | 5.20545 | 5.49264 | 25.28928 |
| Pancreas tumor 2 | 8.11612 | 8.14771 | 6.0728 | 8.00791 | 30.34454 |
| Pancreas tumor 3 | 7.3283 | 6.74037 | 6.54589 | 6.29493 | 26.90949 |
| Pancreas tumor 4 | 10.8232 | 10.1569 | 8.23528 | 8.18082 | 37.3962 |

TABLE 37-continued

CTA genes expression in normal and pancreas tumors

| Tissue type | Expression of CEP55 | Expression of PBK | Expression of TTK | Expression of OIP5 | sum Expression |
|---|---|---|---|---|---|
| Pancreas tumor 5 | 7.63468 | 6.50474 | 6.71224 | 6.22659 | 27.07825 |
| Pancreas tumor 6 | 8.6355 | 8.32513 | 7.28934 | 6.63727 | 30.88724 |
| T test | 0.003268 | 0.003391 | 0.004281 | 0.00552 | 0.002706 |
| Diff | 2.534892 | 1.396275 | 2.210472 | 1.888577 | 8.33837 |

Figure 19:
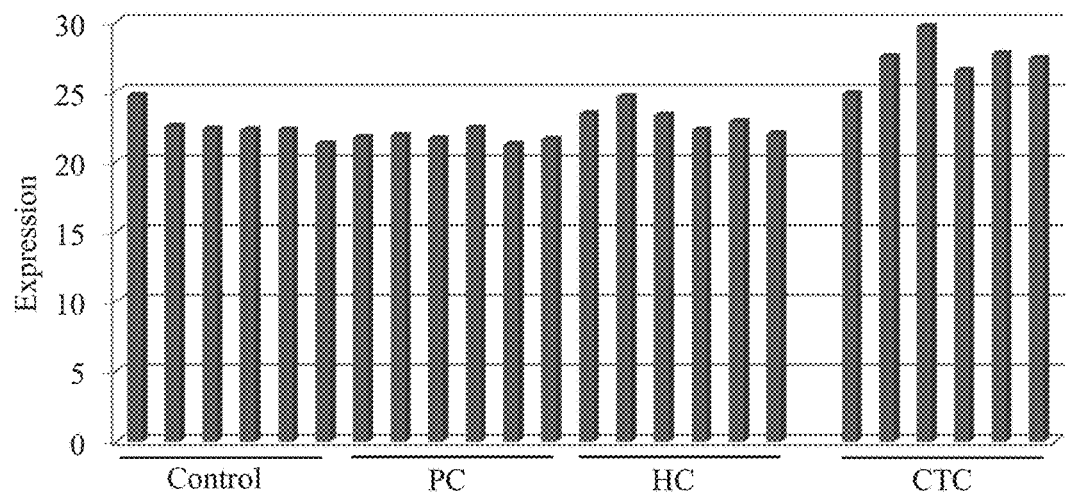
FIG. 19 is a bar graph showing sum expression of DSCR8, CCDC33, BAGE, DKKL1 and TULP2 in normal pancreas samples (Control), pancreas cancer samples (PC), hematological cells samples (HC) and CTCs of pancreas samples (CTC).

Further, CTAs expression in CTCs and regular hematological cells, as well as in normal pancreas and cancerous pancreas, was compared. A unique gene expression signature specific only to metastasis of pancreas was identified. The sum expression of: DSCR8, CCDC33, BAGE, DKKL1 and TULP2, was found to significantly distinguish CTCs of pancreas from hematological cells, as well as normal distinguish healthy pancreas samples and pancreas cancer samples (FIG. 19).

Example 14

CTA Signature for Detecting Circulating Tumor Cells (CTC) of the Lung in Blood CTAs expression in CTCs and lung cancer tissues, was compared. A unique gene expression signature specific to CTCs and metastatic cells were found. The sum increase in expression of: ACRBP and CCDC62, was found to significantly distinguish CTCs of lung from primary and metastatic cells (Table 38). The sum increase in expression of: CTCFL, PAGE5 and LDHC, was found to significantly distinguish metastatic lung cells from CTCs of lung (Table 39).

TABLE 38

CTA genes in primary lung tumors, metastatic lung lesions and CTCs of Lung

| Tissue type | Expression of ACRBP | Expression of CCDC62 |
|---|---|---|
| H1299 cell grown on 4D model - primary tumor on day 2, biological replicate #1 | 8.061 | 71.86535 |
| H1299 cell grown on 4D model - primary tumor on day 2, biological replicate #2 | 11.0735 | 79.46735 |
| H1299 cell grown on 4D model - primary tumor on day 2, biological replicate #3 | 7.3815 | 77.30655 |
| H1299 cell grown on 4D model - primary tumor on day 25, biological replicate #1 | 9.9579 | 110.2609 |
| H1299 cell grown on 4D model - primary tumor on day 25, biological replicate #2 | 7.8318 | 95.16655 |
| H1299 cell grown on 4D model - primary tumor on day 25, biological replicate #3 | 13.3207 | 106.5975 |
| Metastatic lesion from 4D model day 10, biological replicate #1 | 7.44 | 76.2417 |
| Metastatic lesion from 4D model day 10, biological replicate #2 | 6.7565 | 81.7954 |
| Metastatic lesion from 4D model day 10, biological replicate #3 | 8.2455 | 89.4704 |
| Metastatic lesion from 4D model day 25, biological replicate #1 | 8.8464 | 75.8103 |
| Metastatic lesion from 4D model day 25, biological replicate #2 | 7.2008 | 84.38555 |
| Metastatic lesion from 4D model day 25, biological replicate #3 | 10.9477 | 73.9162 |
| CTC from 4D model on day 10, biological replicate #1 | 17.7063 | 130.1034 |
| CTC from 4D model on day 10, biological replicate #2 | 16.1516 | 147.187 |
| CTC from 4D model on day 10, biological replicate #3 | 19.9542 | 155.2132 |
| CTC from 4D model on day 25, biological replicate #1 | 14.0161 | 125.9039 |
| CTC from 4D model on day 25, biological replicate #2 | 17.5819 | 125.456 |
| CTC from 4D model on day 25, biological replicate #3 | 14.7709 | 122.27 |
| T test | 1.11E-06 | 1.13E-06 |
| log | 0.904145 | 0.657295 |

TABLE 39

CTA genes in metastatic lung lesions and CTCs of Lung

| Tissue type | Expression of CTCFL | Expression of PAGE5 | Expression of LDHC |
|---|---|---|---|
| CTC from 4D model on day 10, biological replicate #1 | 2674.395 | 31.4346 | 99.6735 |
| CTC from 4D model on day 10, biological replicate #2 | 2173.16 | 37.9755 | 106.7972 |
| CTC from 4D model on day 10, biological replicate #3 | 3247.87 | 30.66735 | 117.4868 |
| CTC from 4D model on day 25, biological replicate #1 | 2478.264 | 36.82805 | 127.5319 |
| CTC from 4D model on day 25, biological replicate #2 | 2479.736 | 35.6774 | 112.8868 |
| CTC from 4D model on day 25, biological replicate #3 | 3142.107 | 48.5867 | 139.8645 |
| Metastatic lesion from 4D model day 10, biological replicate #1 | 5635.192 | 67.15365 | 272.7366 |
| Metastatic lesion from 4D model day 10, biological replicate #2 | 5139.034 | 59.8095 | 217.4457 |
| Metastatic lesion from 4D model day 10, biological replicate #3 | 5091.334 | 53.7723 | 191.6588 |
| Metastatic lesion from 4D model day 25, biological replicate #1 | 4381.029 | 74.43335 | 173.9219 |
| Metastatic lesion from 4D model day 25, biological replicate #2 | 4122.888 | 41.2146 | 131.3903 |
| Metastatic lesion from 4D model day 25, biological replicate #3 | 4119.673 | 64.90015 | 176.5741 |
| T test | 5.72E-05 | 0.00155 | 0.003714 |
| log | 0.814817 | 0.707978 | 0.724613 |

Example 15

A CTA Signature for Distinguishing Between Stages 1-4 of Ovarian Cancer

Figure 20A:
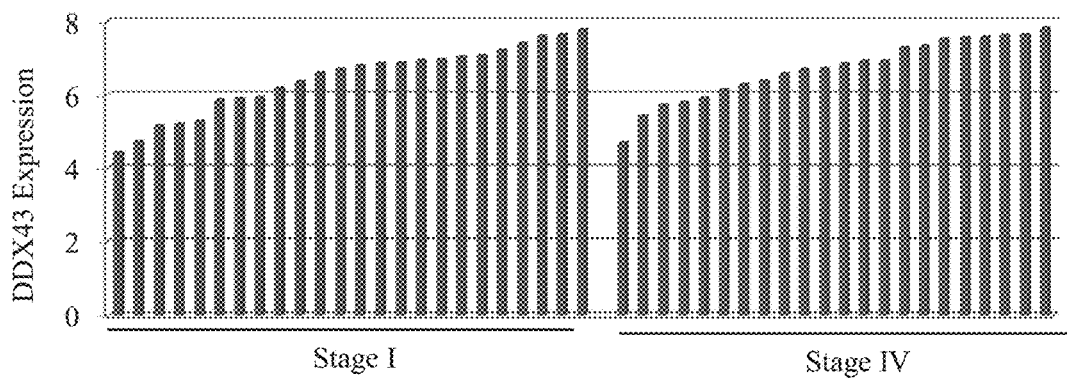
FIGS. 20A-D are bar graphs showing expression of DDX43 (20A), KIAA0100 (20B), MAGEA4 (20C), and the sum of the expression of all three (20D) in Stage I and Stage IV ovarian cancer.
Figure 20B:
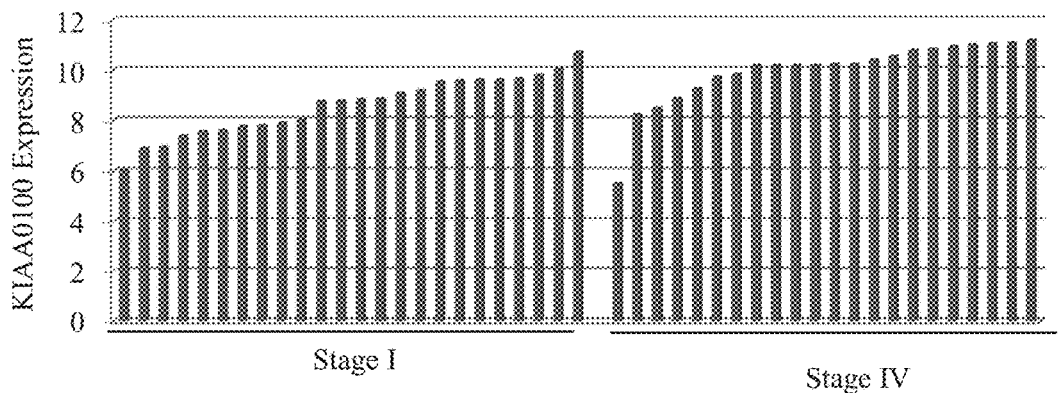
Figure 20C:
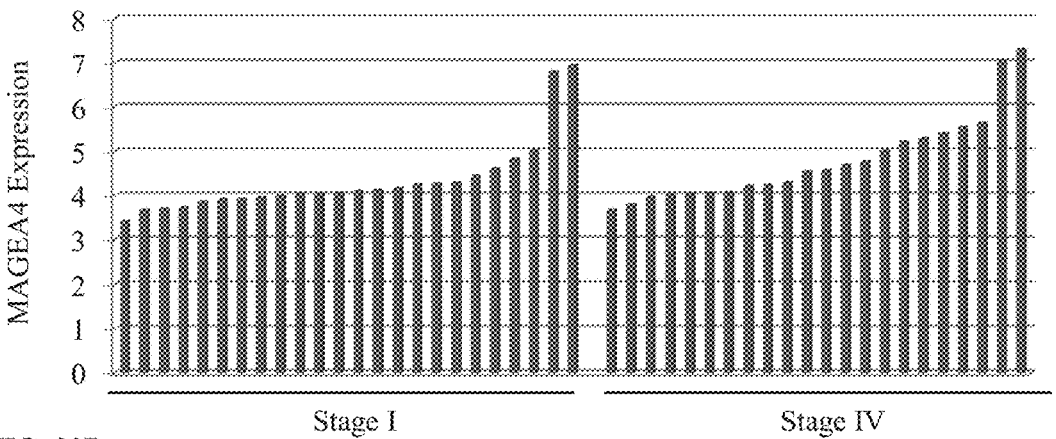
Figure 20D:
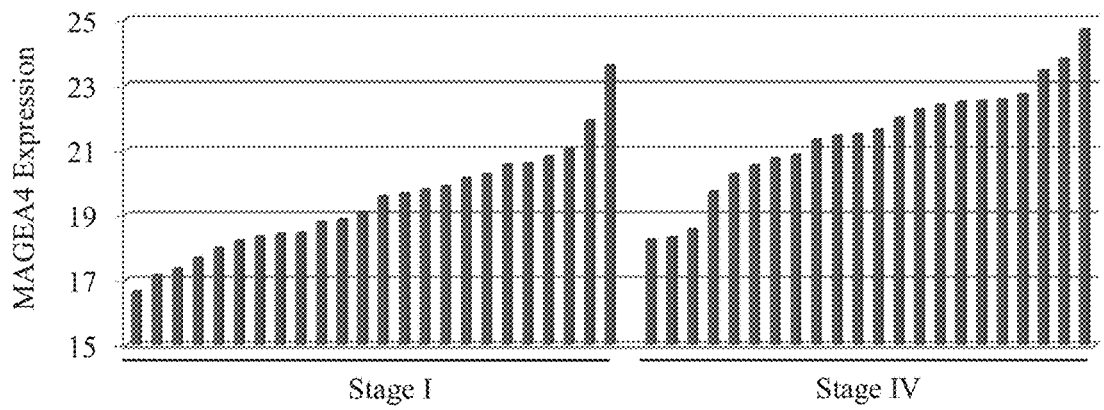
Figure 21:
FIG. 21 is a graph showing expression of KIAA0010 in different stages of ovarian cancer.

Expression of CTAs in different stages of ovarian cancer, was analyzed. The CTAs: DDX43, KIAA0100 and MAGEA4 were found to have increased expression in stage 4 ovarian cancer as compared to stage 1 (FIGS. 20A-C), and the sum of the expression of all three distinguished Stage 4 diagnostically (FIG. 20D). Further, the expression of KIAA0100 could statistically significantly distinguishing between different stages of ovarian cancer (FIG. 21).

Example 16

A CTA Signature in Pluripotent hESCs

CTAs expression in human embryonic stem cells (hESCs) which differentiate in the presence of nicotine amide was compared to that of human embryonic stem cells (hESCs) which differentiate in the absence of nicotine amide (lower potency). It was found that the higher the expression of the CTAs: CTNNA2, TMEFF1, SPA17 and PBK the more potent and undifferentiated was the state of the hESCs (Table 40).

TABLE 40

CTA genes expression in hESCs having different potency

|  | CTNNA2 | TMEFF1 | SPA17 | PBK |
| --- | --- | --- | --- | --- |
| hESCs differentiating without NIC | 22.3 | 91.9 | 70.6 | 215.6 |
| hESCs differentiating without NIC | 29.4 | 245.95 | 69.3 | 177.7 |
| hESCs differentiating without NIC | 23.5 | 250.25 | 53.1 | 168.4 |
| hESCs differentiating with NIC | 111.2 | 486.35 | 159.1 | 408.7 |
| hESCs differentiating with NIC | 243.2 | 628.85 | 177.4 | 354 |
| hESCs differentiating with NIC | 151.4 | 634.15 | 197.7 | 414.7 |
| T test |  | 0.021418 | 0.005529 | 0.000806 | 0.001045 |
| diff |  | 2.749762 | 1.572686 | 1.468779 | 1.067733 |

Example 17

A CTA Signature in Cancer Stem Cells (CSCs)

Two different normal primary human mammary epithelial cell populations (BPECs and HMECs) were isolated and immortalized by hTERT giving rise to BPE and HME cells. These hTERT immortalized cells (BPE and HME) were transformed by SV40-early region (LT+st) and H-Ras which gave rise to transformed tumorigenic derivatives BPLER and HMLER. CTA expression in these cells was analyzed. It was found that there was higher expression of CTAs: CEP55, PBK, TTK, OIP5, and ATAD2 in transformed cancer stem cells as compared to normal primary human mammary epithelial cells.

TABLE 41

CTA genes expression in transformed cells

| Gene symbol | BPEAVG | BPLERAVG | R-BASE BP | HMLE AVG | HMLER AVG | R-BASE HM |
| --- | --- | --- | --- | --- | --- | --- |
| IL13RA2 | 5.907172 | 5.40662 | −0.50055 | 6.436307 | 10.42036 | 3.984051 |
| GPAT2 | 2.028029 | 2.864418 | 0.83639 | 3.05768 | 6.935626 | 3.877946 |
| PBK | 9.432218 | 9.932898 | 0.50068 | 8.572198 | 11.66863 | 3.096436 |
| OIP5 | 7.42425 | 8.546694 | 1.122444 | 6.184963 | 8.990744 | 2.805781 |
| TTK | 7.711666 | 8.944823 | 1.233156 | 7.258332 | 9.9604 | 2.702068 |
| ATAD2 | 7.496898 | 9.471297 | 1.9744 | 7.352398 | 9.672311 | 2.319913 |
| CEP55 | 8.95763 | 10.25854 | 1.300913 | 8.821157 | 10.68188 | 1.860721 |

TABLE 41-continued

CTA genes expression in transformed cells

| Gene symbol | BPEAVG | BPLERAVG | R-BASE BP | HMLE AVG | HMLER AVG | R-BASE HM |
|---|---|---|---|---|---|---|
| SPAG4 | 3.482437 | 4.062687 | 0.580249 | 4.749619 | 6.543974 | 1.794354 |
| SPA17 | 8.038838 | 7.754513 | −0.28433 | 7.326577 | 8.950746 | 1.624169 |
| SPAG1 | 8.63498 | 10.12496 | 1.489981 | 5.920957 | 7.286058 | 1.365102 |

Figure 22A:
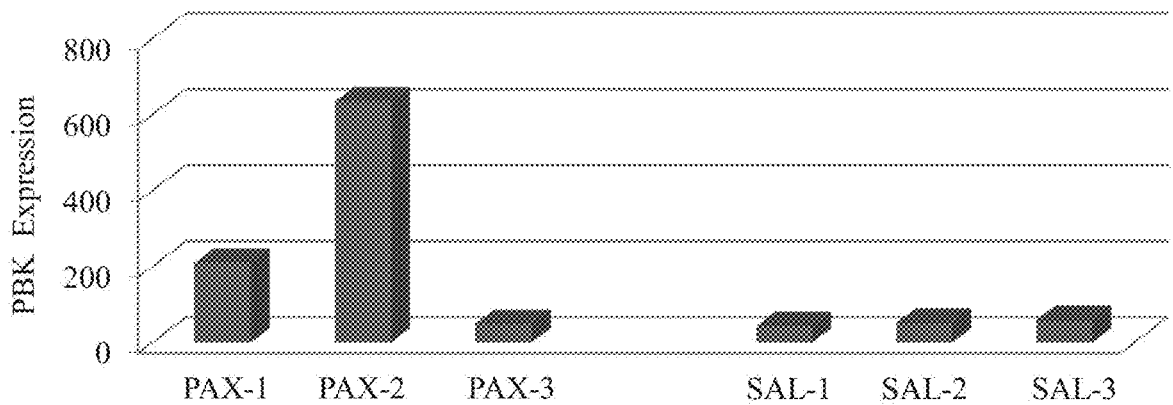
FIGS. 22A-C are bar graphs showing expression of PBK (22A), CEP55 (22B) and TTK (22C) in HMLER cells treated with either paclitaxel (three replicates, PAX-1,2,3) or salinomycin (three replicates, SAL-1,2,3).
Figure 22B:
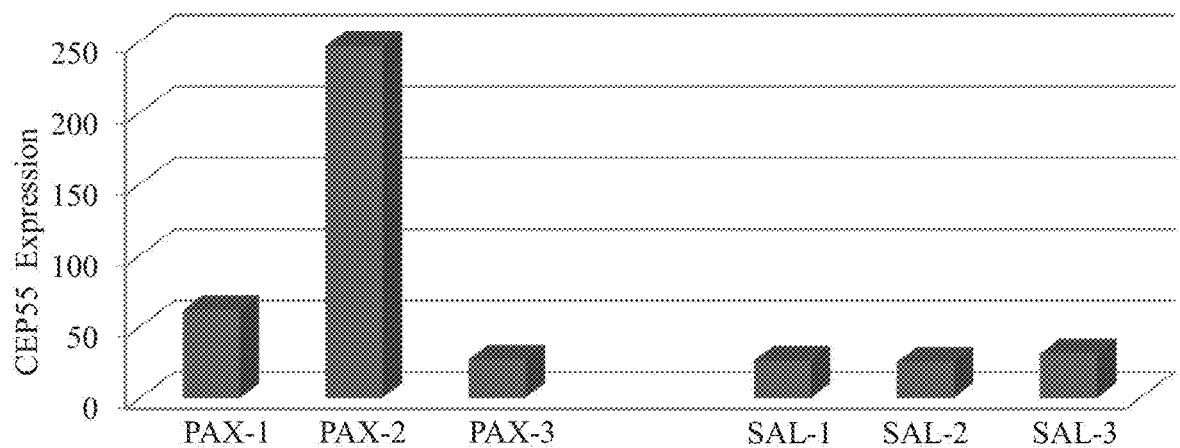
Figure 22C:
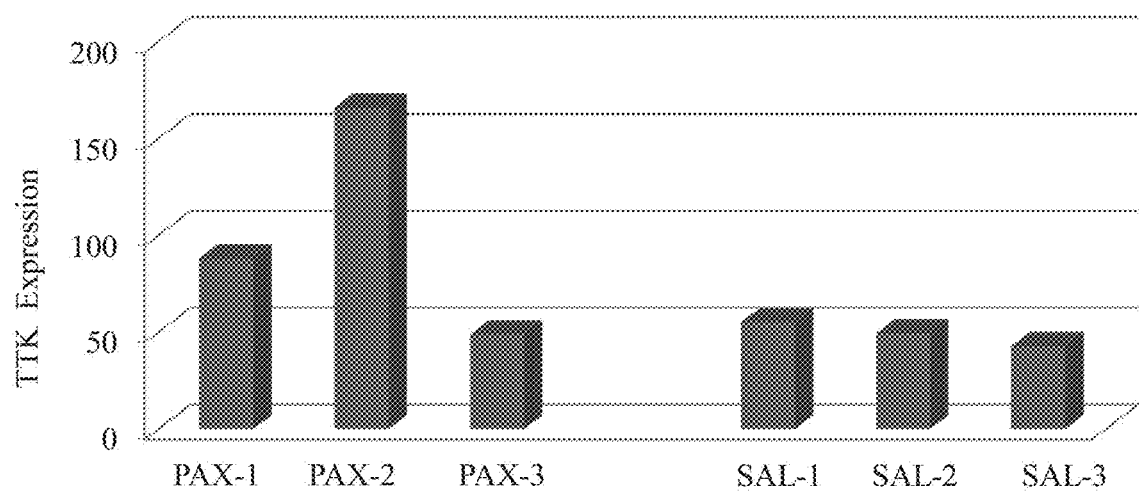

Further, transformed HMLER breast cancer cells were treated with salinomycin and paclitaxel. Salinomycin reduces the number of cancer stem cells by 100 folds relative to paclitaxel (results not shown). Expression of PBK, CEP55, and TTK in HMLER cells treated with salinomycin was substantially reduced (FIGS. 22A-C).

Example 18

A CTA Signature for Determining Lymphatic Metastasis

Oral cancer is one of the most common types of tumor in the head and neck. Oral squamous cell carcinoma is an invasive lesion with the presence of perineural growth. It has a significant recurrence rate and frequently metastasizes to cervical lymph nodes.

Samples derived from subjects having tongue squamous cell carcinoma were evaluated to determine whether a CTA signature may predict lymphatic metastasis as well as provide a prognostic value.

Figure 23:
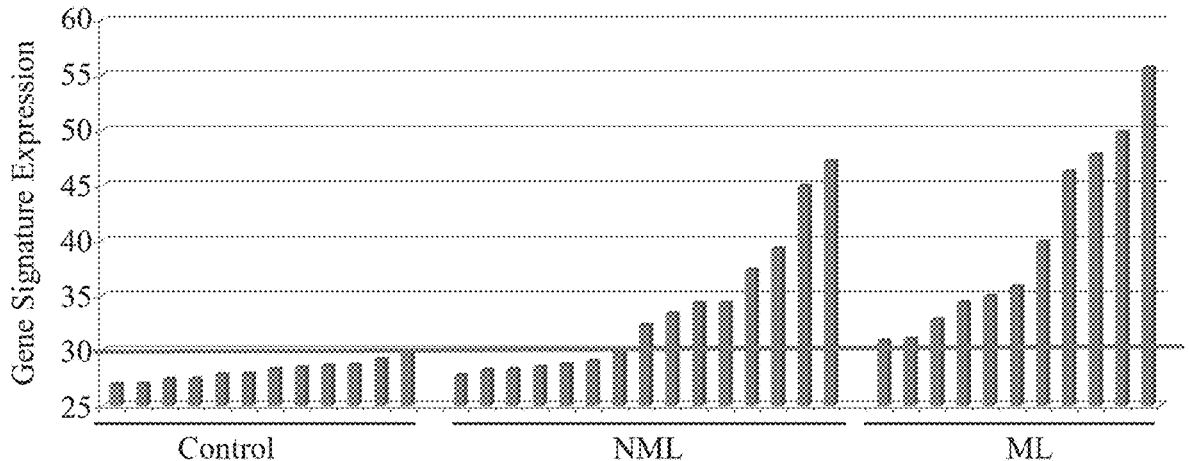
FIG. 23 is a bar graph showing sum expression of LY6K, MAGEA6, PLAC1, LEMD1, MAGEA1, MAGEA11, MAGEA4, MAGEA12, and CEP55 in normal oral samples (Control), oral squamous cell carcinoma samples that have not metastasized to the lymph (NML), and oral squamous cell carcinoma samples that have metastasized to the lymph (ML). Thick line represents ideal cut-off.
Figure 24A:
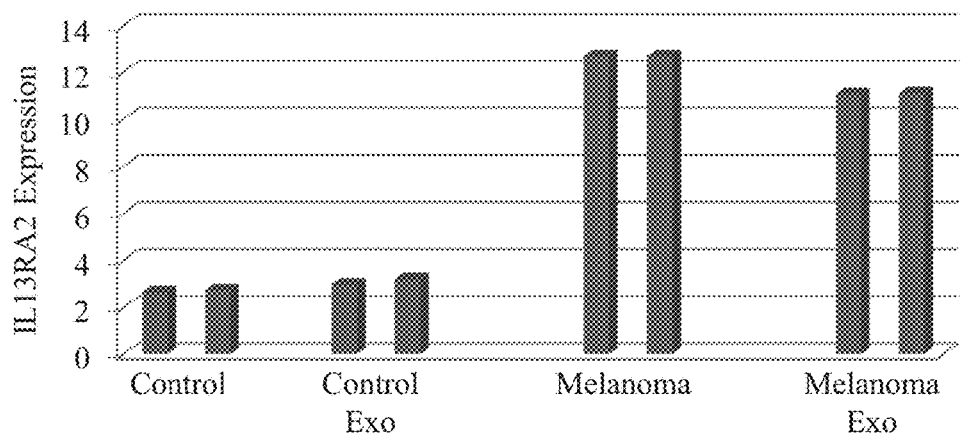
FIGS. 24A-D are bar graphs showing expression of IL13RA2 (24A), MAGEA4 (24B), CEP55 (24C) and PBK (24D) in control and cancer cells and their exosomes.
Figure 24B:
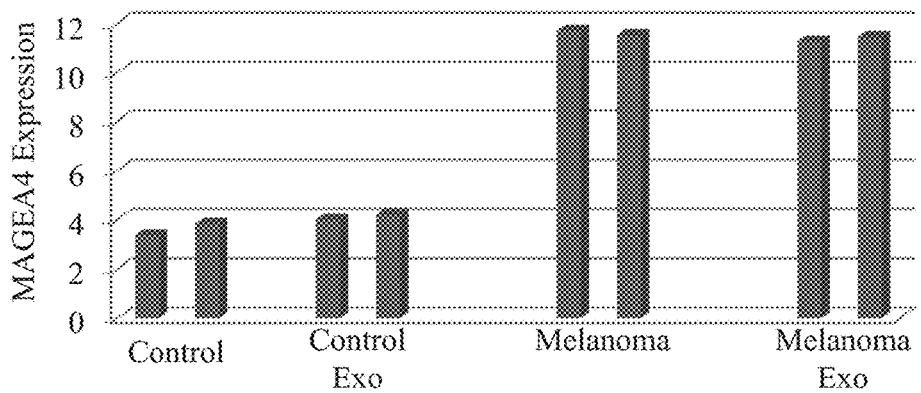
Figure 24C:
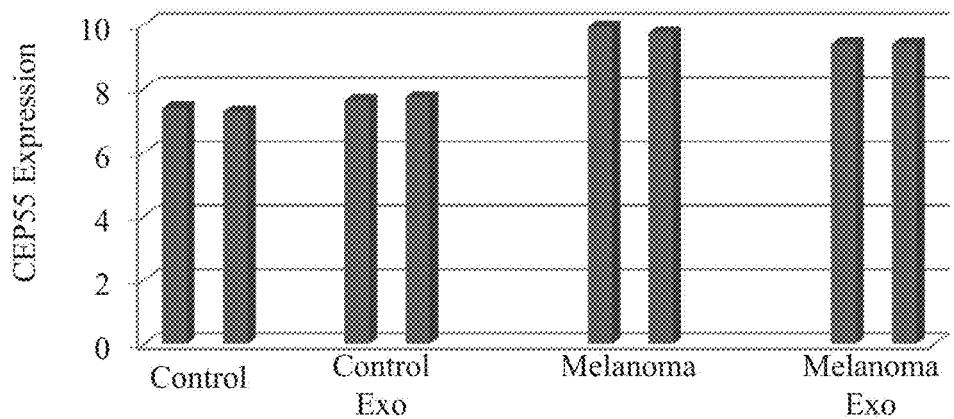
Figure 24D:
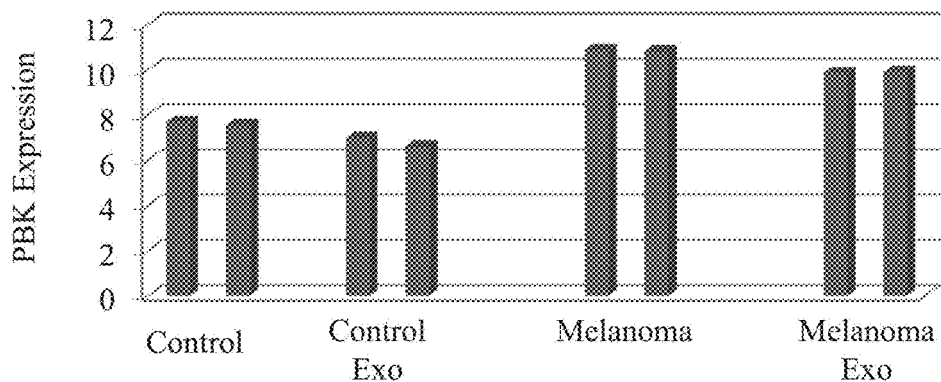

A specific CTA signature comprising LY6K, MAGEA6, PLAC1, LEMD1, MAGEA1, MAGEA11, MAGEA4, MAGEA12, and CEP55 was found to identify oral squamous cell carcinoma as well as predict lymphatic metastasis (FIG. 23).

Example 19

Detection of the CTA Signatures in Exosomes

The expression profile of exosomes was evaluated on order to determine whether the CTA signatures provided herein may be detected in exosomes.

Analyzing samples derived from subjects afflicted with melanoma revealed an exosome expression profile including IL13RA2, MAGEA4, CT45A1/CT45A2/CT45A3/CT45-A4/CT45A5/CT45A6/LOC101060211/LOC102723631/LOC102723680/LOC102723737, MAGEA3/MAGEA6, MAGEA6, MAGEA12, and MAGEA2/MAGEA2B. The expression profile also revealed the following non-CT antigens: HLA-DRA LINC01419, and GTSF1.

Interestingly, the exosomes derived from both the normal and cancer lines resemble the original source (FIGS. 24A-D). This indicates that monitoring exosome expression can provide an indication on the occurrence, severity and staging of various cancers including melanoma.

Figure 25A:
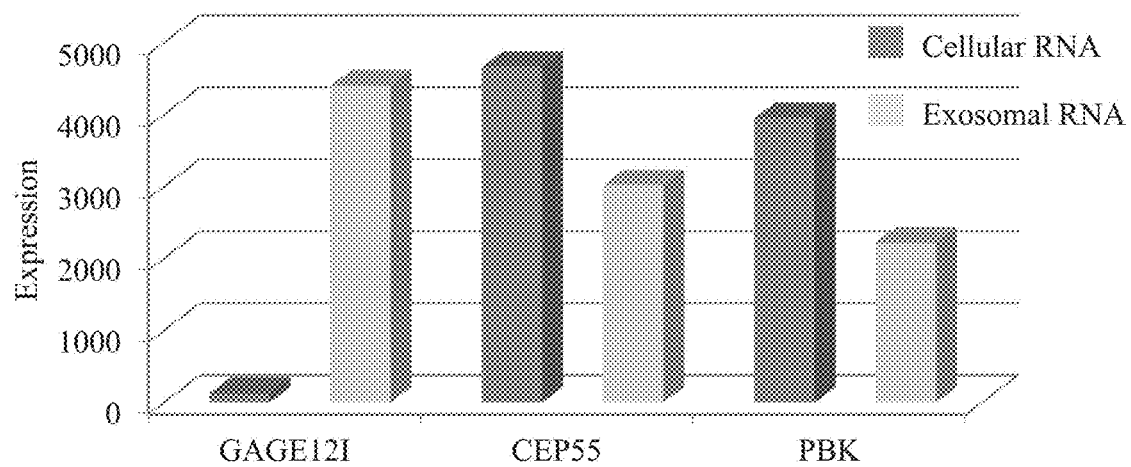
FIGS. 25A-B are bar graphs showing expression of a X chromosome gene (GAGE12I) and two mitotic genes (CEP55, PBK) in melanoma cells (25A) and glioblastoma cells (25B) and their exosomes.
Figure 25B:
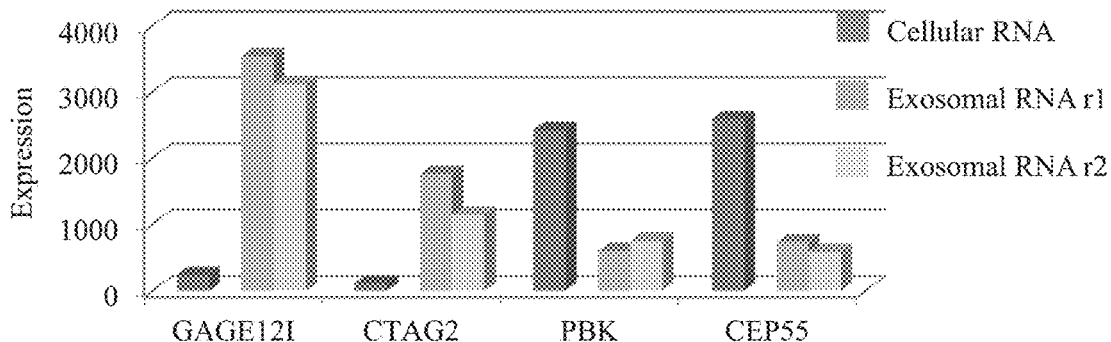
Figure 26A:
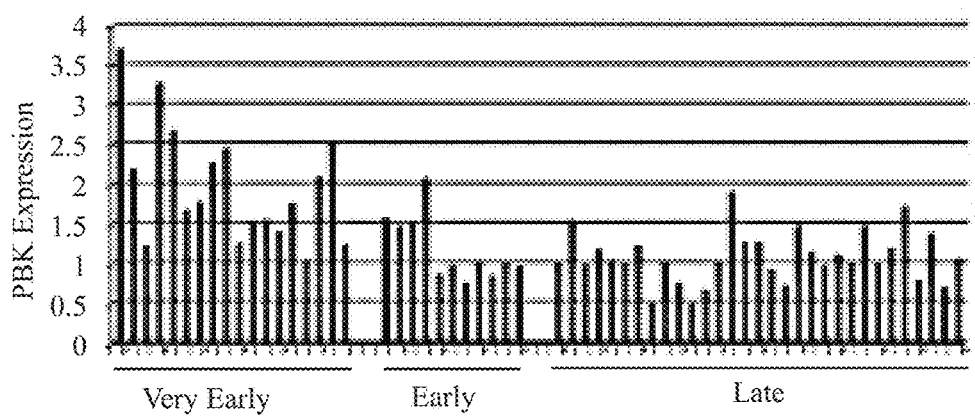
FIGS. 26A-F are bar graphs showing expression of PBK (26A), TTK (26B), OIP5 (26C), OIP5 (26D), ATAD2 (26E) and the combine gene signature (26F) in very early, early and late relapsing ALL. Thick line represents ideal cut-off.
Figure 26B:
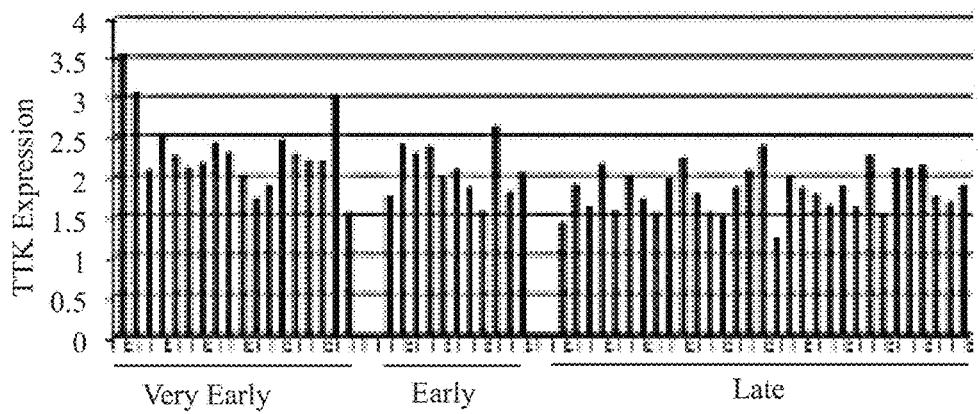
Figure 26C:
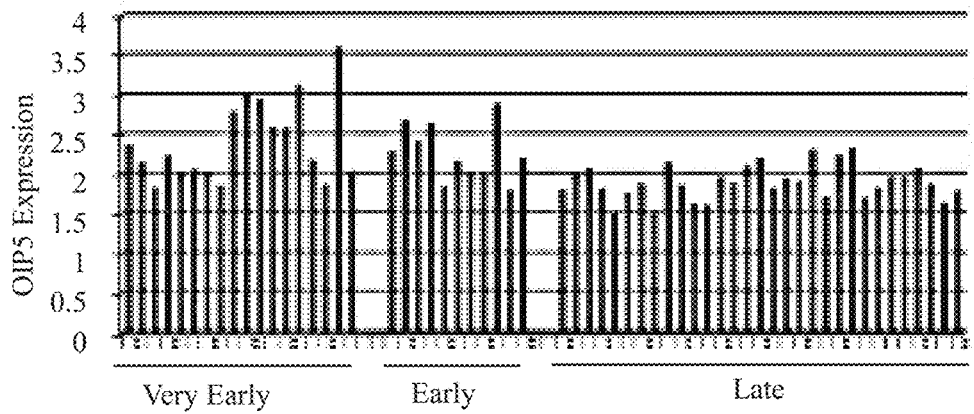
Figure 26D:
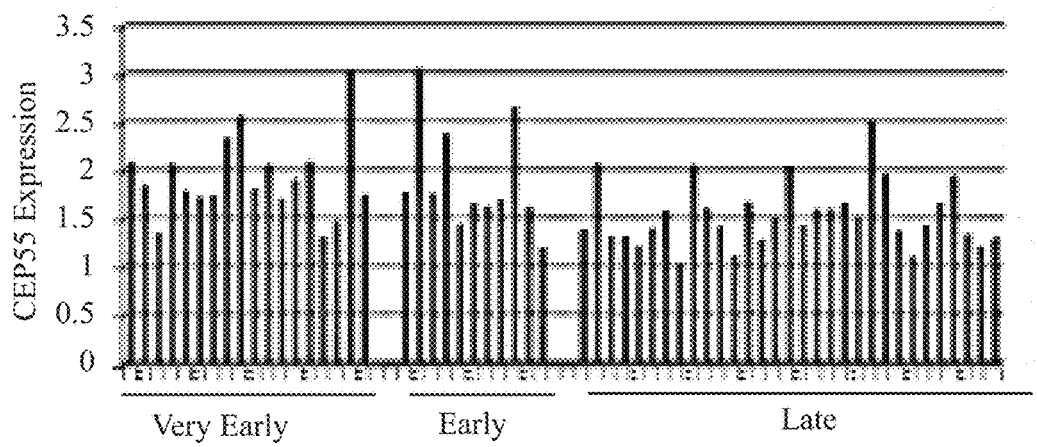
Figure 26E:
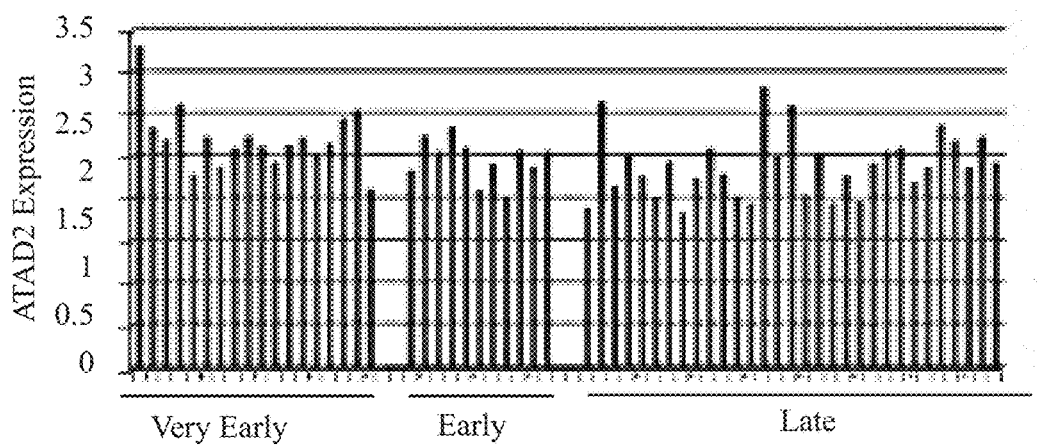
Figure 26F:
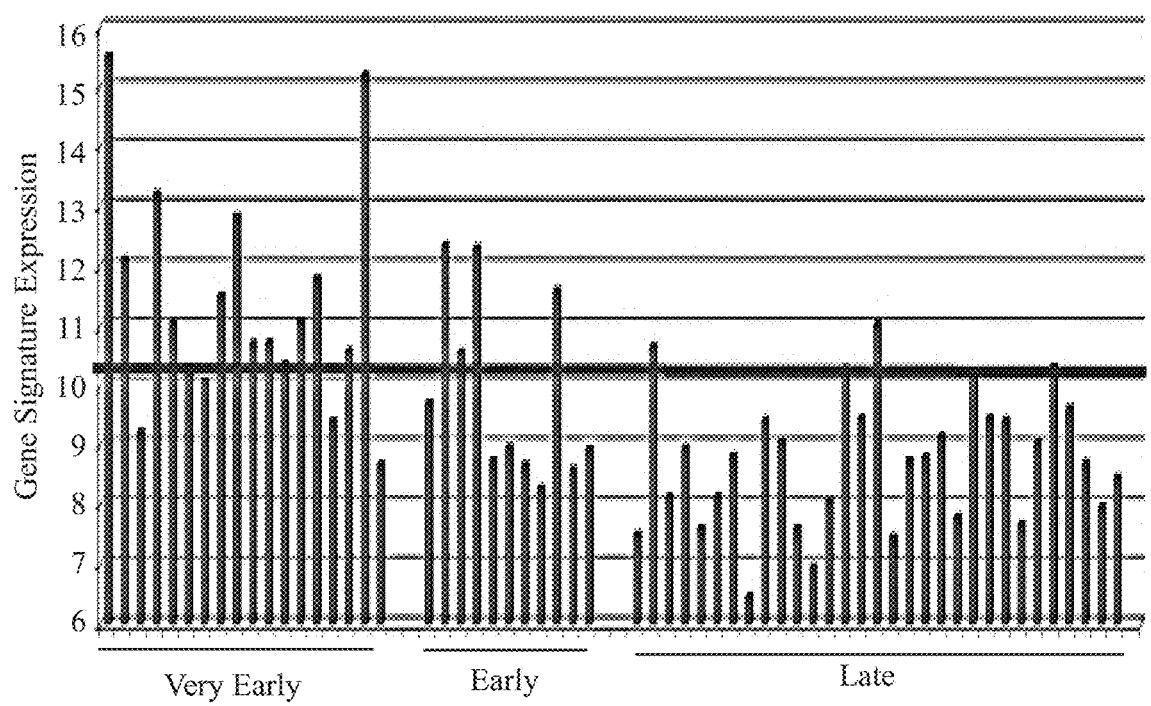

Further, comparing the gene expression profiles in exosomes/microvesicles of subjects afflicted with glioblastoma and melanoma compared to the cells that release them, it was found that the X components of the CTA (Random on X chromosome) is up regulated in the exosomes while the consistent mitotic component (CEP55, PBK, TTK) remain relatively unchanged (FIGS. 25A-B).

Example 20

A CTA Signature for Detecting Acute Lymphoblastic Leukemia (ALL)

Statistical analyses using the ranking method revealed that very early relapse of ALL can be identified by the high expression of the individual mitotic components of the CTA, including PBK, TTK, OIP5, CEP55, and ATAD2, or by the signature of all five (FIGS. 26A-F).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method for treating oral squamous cell carcinoma in a human subject, the method comprising:
    obtaining a biological sample from an oral tissue having or suspected of having oral squamous cell carcinoma in the human subject; wherein the biological sample is obtained from the subject prior to initiation of an anti-cancer treatment;
    obtaining mRNA from said biological sample and measuring mRNA levels corresponding to cancer testis antigens (CTAs);
    determining in the biological sample an expression profile of said CTAs, wherein said CTAs comprise lymphocyte antigen 6 family member K (LY6K), MAGE family member A6 (MAGEA6), placenta enriched 1 (PLAC1), LEM domain containing 1 (LEMD1), MAGE family member A1 (MAGEA1, MAGE family member A11 (MAGEA11), MAGE family member A4 (MAGEA4), MAGE family member A12 (MAGEA12), and centrosomal protein 55 (CEP55);
    determining an increase in a sum expression of said CTAs in said biological sample, as compared to a reference sum expression of said CTAs, and
    administering an anti-cancer treatment to the subject when there is an increase in the sum expression of said CTAs in said biological as compared to the reference sum expression of said CTA, thereby treating said oral squamous cell carcinoma in said subject.

2. The method of claim 1, further comprising reverse transcribing the mRNA molecule to obtain cDNA molecules, and amplifying said cDNA molecules by polymerization chain reaction (PCR) technique using forward and reverse primers corresponding to said CTAs and quantitatively assessing the amount of cDNA formed, thereby determining the expression of said CTAs.

3. The method of claim 1, further comprising reverse transcribing the mRNA molecules to obtain cDNA molecules, wherein said cDNA molecules are arrayed on a substrate and contacted with detectably labeled cDNA of said CTAs.

4. The method of claim 1, comprising hybridizing said mRNA or a cDNA thereof with a labeled nucleic acid hybridization probe corresponding to said CTAs.

5. The method of claim 1, further comprising determining oral squamous cell carcinoma in said subject having an increase in the sum expression of said CTAs as compared to the reference sum expression of said CTAs, wherein said reference sum expression is of a healthy oral tissue of a human subject.

6. The method of claim 1, wherein said reference sum expression is selected form the group consisting of: a sample from healthy neighboring tissue of said subject, a sample from previous test(s) of said subject, a sample from at least one healthy subject, a panel of samples from healthy subjects, and a stored set of data from the oral tissue of human subjects.

7. The method of claim 1, further comprising determining metastasis in the subject determined to have an increase in the sum expression of said CTAs as compared to the reference sum expression.

8. The method of claim 6, wherein said stored set of data from the oral tissue of human subjects is a predefined threshold obtained by a statistical analysis of expression profiles of subjects having oral squamous cell carcinoma samples that have metastasized to the lymph.

9. The method of claim 1, wherein said anti-cancer treatment is chemotherapy.

\* \* \* \* \*